United States Patent [19]
Debs et al.

[11] Patent Number: 6,001,644
[45] Date of Patent: Dec. 14, 1999

[54] MAMMALIAN TRANSFORMATION COMPLEX COMPRISING A LIPID CARRIER AND DNA ENCODING CFTR

[75] Inventors: Robert J. Debs, Mill Valley; Ning Zhu, El Cerrito, both of Calif.

[73] Assignee: The Regents of the University of California, Oakland, Calif.

[21] Appl. No.: 08/256,004

[22] PCT Filed: Dec. 17, 1992

[86] PCT No.: PCT/US92/11004

§ 371 Date: Aug. 22, 1994

§ 102(e) Date: Aug. 22, 1994

[87] PCT Pub. No.: WO93/12240

PCT Pub. Date: Jun. 24, 1993

Related U.S. Application Data

[63] Continuation-in-part of application No. 07/972,135, Nov. 5, 1992, Pat. No. 5,858,784, and application No. 07/927,200, Aug. 6, 1992, abandoned, said application No. 07/972,135, is a continuation-in-part of application No. 07/809,291, Dec. 17, 1991, abandoned, said application No. 07/927,200, is a continuation-in-part of application No. 07/894,498, Jun. 4, 1992, abandoned.

[51] Int. Cl.$^6$ ............................ C12N 15/00; C12N 15/63
[52] U.S. Cl. ....................... 435/320.1; 435/458; 514/44; 128/200; 128/14; 128/18; 128/23; 128/24; 424/450
[58] Field of Search ................................ 514/44; 935/62, 935/54, 55; 435/320.1, 172.1, 172.3, 458; 128/200, 14, 18, 23, 24; 424/450

[56] References Cited

U.S. PATENT DOCUMENTS

| | | | |
|---|---|---|---|
| 3,826,255 | 7/1974 | Havstad et al. | 128/194 |
| 4,046,146 | 9/1977 | Rosskamp et al. | 128/266 |
| 4,253,468 | 3/1981 | Lehmbeck | 128/726 |
| 4,268,460 | 5/1981 | Boiarski et al. | 261/1 |
| 4,510,929 | 4/1985 | Bordeni et al. | 128/200.14 |
| 4,649,911 | 3/1987 | Knight et al. | 128/200.21 |
| 4,804,678 | 2/1989 | Augstein et al. | 514/456 |
| 4,946,787 | 8/1990 | Eppstein et al. | 435/240.2 |
| 5,049,386 | 9/1991 | Eppstein et al. | 424/427 |
| 5,240,846 | 8/1993 | Collins et al. | 435/240.1 |
| 5,279,833 | 1/1994 | Rose | 424/450 |
| 5,459,127 | 10/1995 | Felgner et al. | 514/7 |
| 5,676,954 | 10/1997 | Brigham | 424/450 |

FOREIGN PATENT DOCUMENTS

| | | | |
|---|---|---|---|
| A0446017 | 9/1991 | European Pat. Off. | C12N 5/12 |
| WO 90/06997 | 6/1990 | WIPO | C12N 15/00 |
| WO 90/11092 | 10/1990 | WIPO | A61K 48/00 |
| WO 91/02796 | 3/1991 | WIPO | C12N 15/12 |
| WO 91/06309 | 5/1991 | WIPO | A61K 37/22 |
| WO 91/15501 | 10/1991 | WIPO | C07H 21/02 |
| WO 92/05252 | 4/1992 | WIPO | C12N 15/12 |
| WO 92/05273 | 4/1992 | WIPO | C12P 21/06 |
| WO 92/19749 | 11/1992 | WIPO | C12N 15/87 |

OTHER PUBLICATIONS

Chou et al., "Characterization of the Promoter Region of the Cystic Fibrosis Transmembrane Conductance Regulator Gene," *The Journal of Biological Chemistry*, vol. 266:24471–24476 (1991).

Schaefer–Ridder, et al., "Liposomes as Gene Carriers: Efficient Transformation of Mouse L Cells by Thymidine Kinase Gene," *Science*, vol. 215:166–168 (1981).

Knowles et al., "A Pilot Study of Aerosolized Amiloride for the Treatment of Lung Disease in Cystic Fibrosis," *The New England Journal of Medicine*, vol. 322:1189–1194 (1990).

Benvenisty, et al., "Direct Introduction of Genes into Rats and Expression of the Genes," *PNAS (USA)*, vol. 83:9551–9555 (1986).

Debs, et al., "Successful Treatment with Aerosolized Pentamidine of Pneumocystis Carinii Pneumonia in Rats," *Antimicrobial Agents and Chemotherapy*, vol. 31, No. 1:37–41 (1987).

Marino et al., "Localization of the Cystic Fibrosis Transmembrane Conductance Regulator in Pancreas," *The American Society for Clinical Investigation, Inc.*, vol. 88:712–716 (1991).

Felgner, et al., "Lipofection: A Highly Efficient, Lipid–Mediated DNA–Transfection Procedure," *PNAS (USA)*, vol. 84:7413–7417 (1987).

Mannino, et al., "Liposome Mediated Gene Transfer," *Biotechniques*, vol. 6 No. 7:682–690 (1988).

Stamatatos, et al., "Interactions for Cationic Lipid Vesicles with Negatively Charged Phospholipid Vesicles and Biological Membranes," *Biochemistry*, vol. 27:3917–3925 (1988).

Debs, et al., "Lung–Specific Delivery of Cytokines Induces Sustained Pulmonary and Systemic Immunomodulation in Rats," *J. Immunology*, vol. 140 No. 10:3482–3488 (1988).

Wu, et al., "Receptor–Mediated Gene Delivery and Expression In Vivo," *J. Biological Chemistry*, vol. 263, No. 29:14621–14624 (1988).

Hubbard, et al., "Fate of Aerosolized Recombinant DNA–Produced α1–Antitrypsin: Use of the Epithelial Surface of the Lower Respiratory Tract to Administer Proteins of Therapeutic Importance," *PNAS (USA)* vol. 86:680–684 (1989).

Malone, et al., "Cationic Liposome–Mediated RNA Transfection," *PNAS (USA)*, vol. 86:6077–6081 (1989).

Rommens, et al., "Identification of the Cystic Fibrosis Gene: Chromosome Walking and Jumping," *Science*, vol. 245:1059–1065 (1989).

Huang, et al., "Intervening Sequences Increase Efficiency of RNA 3' Processing and Accumulation of Cytoplasmic RNA," *Nucleic Acids Research*, vol. 18 No. 4:937–947 (1990).

(List continued on next page.)

Primary Examiner—Deborah Crouch
Assistant Examiner—Jill D. Martin
Attorney, Agent, or Firm—Townsend and Townsend and Crew, LLP

[57] ABSTRACT

Compositions comprising lipid carrier-CFTR nucleic acid complexes are disclosed.

13 Claims, 76 Drawing Sheets

OTHER PUBLICATIONS

Debs, et al., "Regulation of Gene Expression In Vivo by Liposome–Mediated Delivery of a Purified Transcription Factor," *J. Biological Chemistry*, vol. 265 No. 18:10189–10192 (1990).

Verma, "Gene Therapy: Treatment of Disease by Introducing Healthy Genes into the Body is Becoming Feasible. But the Therapy will not reach its full potential until the genes can be coaxed to work throughout life", *Scientific American*, pp. 68–84 (1990).

Hug, et al., "Liposomes for the Transformation of Eukaryotic Cells", *Biochemica et Biophysica Acta*, 1097:1–17 (1991).

Felgner, et al., "Gene Therapeutics", *Nature*, 349:351–352 (1991).

Collins, "Cystic Fibrosis: Molecular Biology and Therapeutic Implications", *Science*, 256:774–779 (1992).

Mercer, et al., "Operating Characteristics of Some Compressed–Air Nebulizers", *Am. Ind. Hyg. Assoc. J.*, 29:66–78 (1968).

Szoka, et al., "Procedure for preparation of liposomes with large internal aqueous space and high capture by reverse–phase evaporation", *PNAS (USA)*, 75(9):4194–4198 (1978).

Mercer, "Production of Therapeutic Aerosols, Principles and Techniques", *Chest*, 80(6):813–817 (1981).

Straubinger, et al., "Liposomes as Carriers for Intracellular Delivery of Nucleic Acids", *Methods in Enzymology*, 101:512–527 (1983).

Gregoriadis, "Liposomes for drugs and vaccines", *Trends in Biotechnology*, 3(9):235–241 (1985).

Debs, et al., "Selective enhancement of Pentamidine uptake in the lung by aerosolization and delivery in liposomes," *Amer. Rev. Respiratory Disease*, 135:731–737 (1987).

Stribling et al., "Aerosol Gene Delivery In Vivo" *Proceedings of the National Academy of Sciences of USA*, vol. 89:11277–11281 (1992).

Yoshimura et al., "Expression of the Human Cystic Fibrosis Transmembrane Conductance Regulator Gene in the Mouse Lung After In Vivo Intratracheal Plasmid–Mediated Gene Transfer" *Nucleic Acids Research*, vol. 20:3233–3240 (1992).

Nabel et al., "Site–Specific Gene Expression in Vivo by Direct Gene Transfer into the Arterial Wall," *Science*, vol. 249:1285–1288 (1990).

Rosenfeld et al., "In Vivo Tranfer of the Human Cystic Fibrosis Transmembrane Conductance Regulator Gene to the Airway Epithelium," *Cell*, vol. 68:143–155 (1992).

Trezise et al., "In Vivo Cell–Specific Expression of the Cystic Fibrosis Transmembrane Conductance Regulator," *Nature*, vol. 353:434–437 (1991).

Wang et al., "pH–Sensitive Immunoliposomes Mediate Target–Cell–Specific Delivery and Controlled Expression of a Foreign Gene in Mouse," *Proc. Natl. Acad. Sci. USA*, vol. 84:7851–7855 (1987).

Brigham et al., "Rapid Communication: In Vivo Transfection of Murine Lungs with a Functioning Prokaryotic Gene Using a Liposome Vehicle," *The American Journal of Medical Sciences*, vol. 298:278–281 (1989).

Brinster et al., "Introns Increase Transcriptional Efficiency in Transgenic Mice," *Proc. Natl. Acad. Sci. USA*, vol. 85:836–840 (1988).

Debs et al., "Prolonged Transgene Expression in Rodent Lung Cells," *Am. J. Respir. Cell Mol. Biol.*, vol. 7:406–413 (1992).

Rose et al., "A New Cationic Liposome Reagent Mediating Nearly Quantitative Transfection of Animal Cells," *BioTechniques*, vol. 10:520–525 (1991).

Drumm et al., "Correction of the Cystic Fibrosis Defect In Vitro by Retrovirus–Mediated Gene Transfer," *Cell*, vol. 62:1227–1233 (1990).

Gregory et al., "Expression and Characterization of the Cystic Fibrosis Transmembrane Conductance Regulator," *Nature*, vol. 347:382–386 (1990).

Miller, "Human Gene Therapy Comes of Age," *Nature*, vol. 357:455–460 (1992).

Nicolau et al., "In Vivo Expression of Rat Insulin After Intravenous Administration of the Liposome–Entrapped Gene for Rat Insulin I," *Proc. Natl. Acad. Sci. USA*, vol. 80:1068–1072 (1983).

Rich et al., "Expression of Cystic Fibrosis Transmembrane Conductance Regulator Corrects Defective Chloride Channel Regulation in Cystic Fibrosis Airway Epithelial Cells," *Nature*, vol. 347:358–363 (1990).

Riordan et al., "Identification of the Cystic Fibrosis Gene: Cloning and Characterization of Complementary DNA," *Science*, vol. 245:1066–1073 (1989).

Stribling et al., "The Mouse as a Model for Cationic Liposome–Based Aerosolized Gene Delivery," *Journal of Biopharmaceutical Sciences*, 3(1/2) 255–263 (1992).

Taylor et al., "Liposomes for Drug Delivery to the Respiratory Tract," *Drug Development and Industrial Pharmacy*, 19 (1/2), 123–142 (1993).

R. Crystal Science 270: 404–10 ('95).

S. Orkin NIH Gene Therapy Report Dec. 1995.

A. Goghland New Scientist Nov. 25, 1995 pp. 14–15.

D. Brown. Wash. Post Dec. 8, 1995 pp. A1 & A22.

R. Palmiter et al. PNAS 88 ('91) 478–82.

T. Maniatis et al. Science 236 ('87) 1237–44.

H. San et al., Human Gene Therapy 4 ('93) 781–788.

E. Wickstrom, J. Biochem. Biophys. Methods 13 ('86) 97–102.

J. Wolffe et al. Science 247 ('90) 1465–68.

D. Porteous et al. Tibtech II (May 1993) 173–81.

N. Dillon Tibetech II (May 1993) 167–73.

A. Miller Nature 357 (Jun. 11, 1992) 455–460.

J. Van Brunt Bio/Technology 6(10) (88) 1149–54.

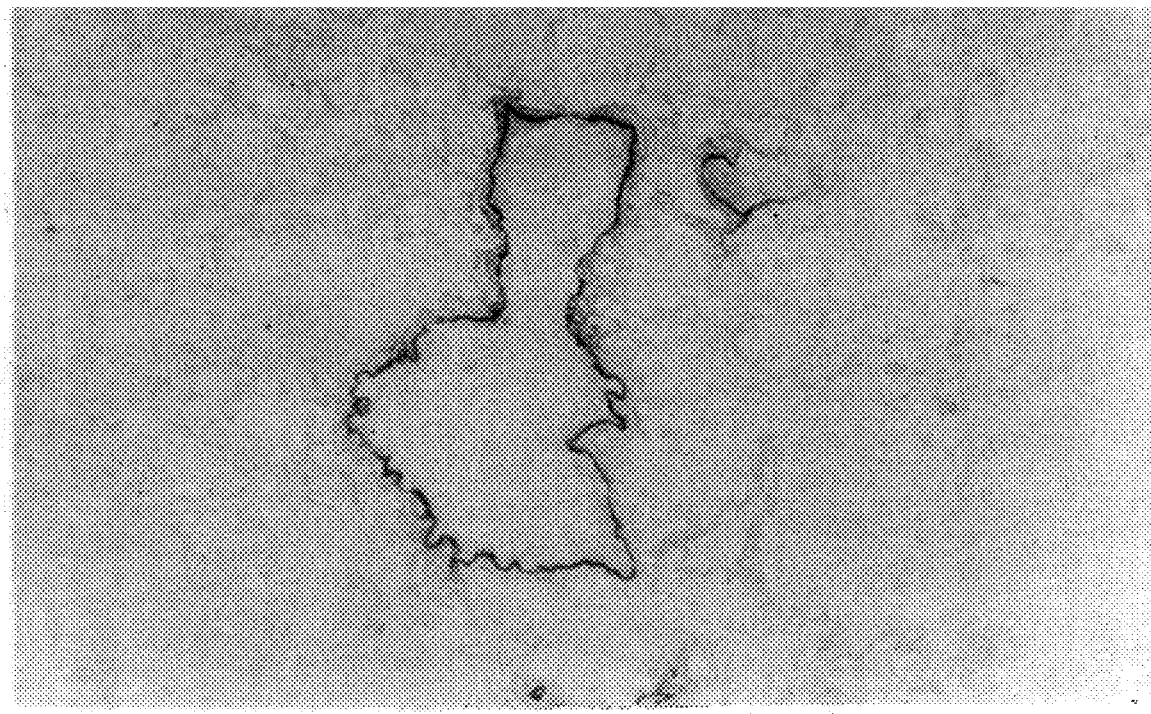
FIG. IC.
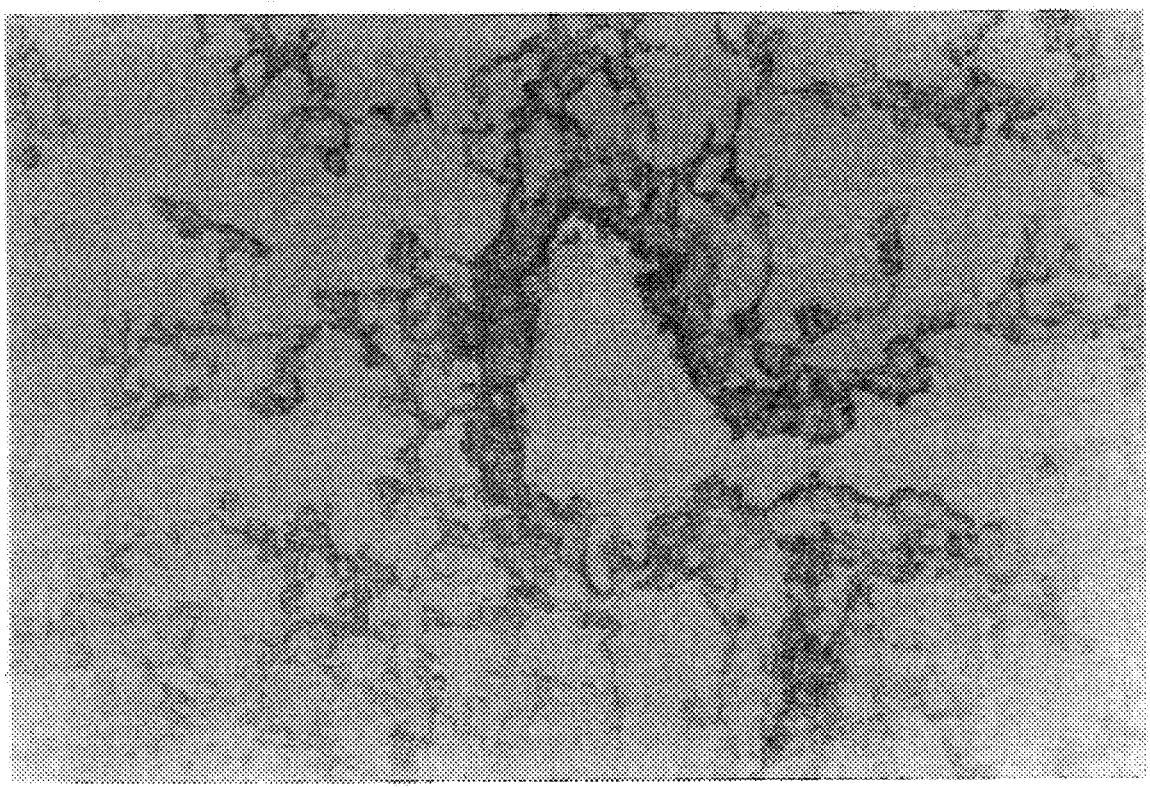
FIG. ID.

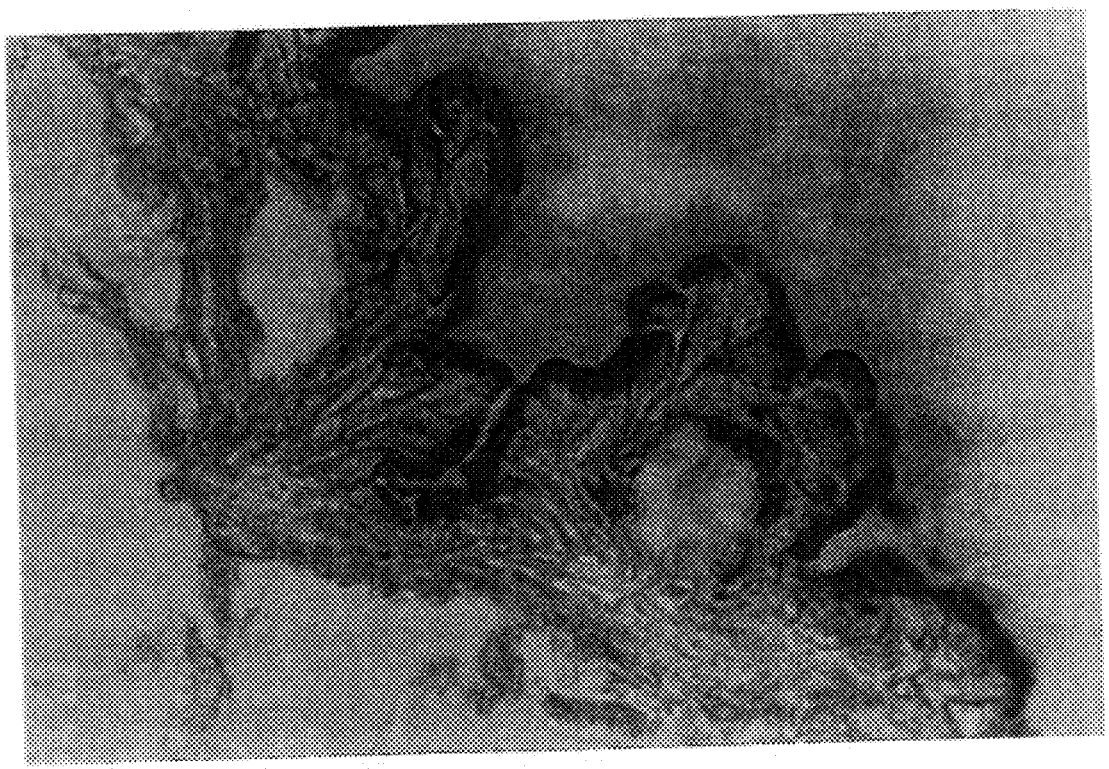
FIG. IE.

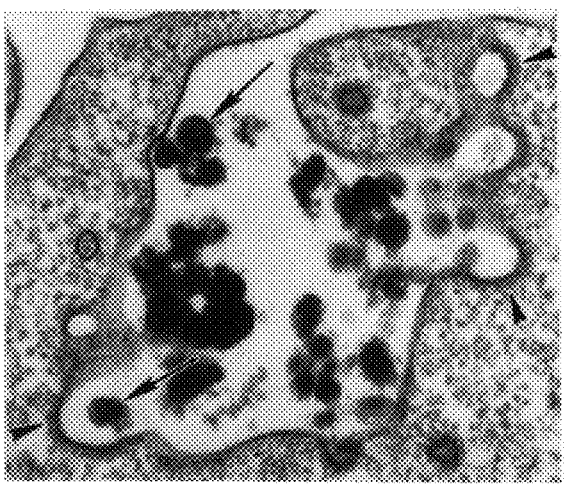
FIG. 4A.
FIG. 4B.
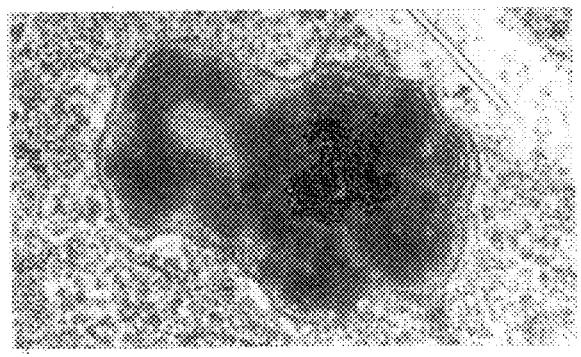
FIG. 4C.
FIG. 4D.
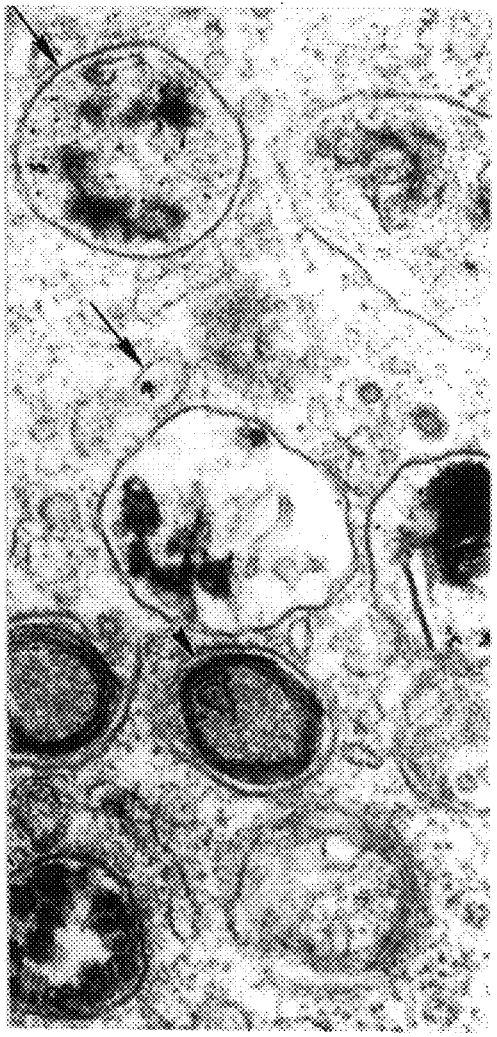
FIG. 4E.
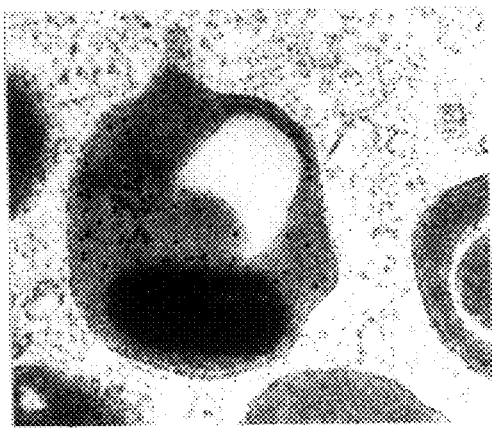
FIG. 4F.

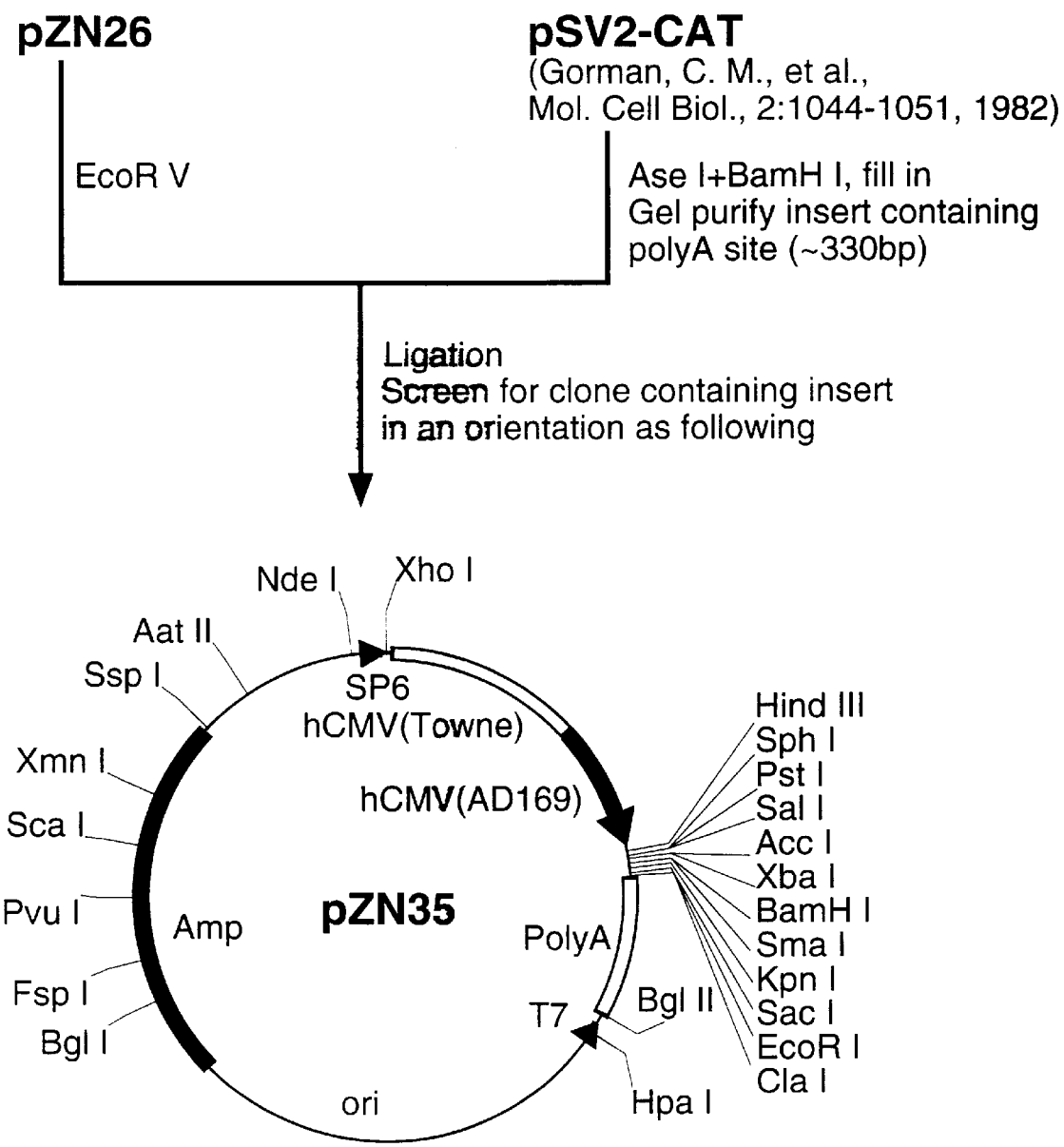
FIG. IIA.

Heart

Spleen

Lung

LN

Kidney

Liver

HCMV (Towne) -> Full Restriction Map

DNA sequence 616 b.p. ggcgaccgccca ... agtgacgtaagt linear

Positions of Restriction Endonucleases sites (unique sites underlined)

```
                    Mae II
                    Aha II
                    Aat II              Mae II                              Mae III
                    HinC II             Mae III
GGCGACCGCCCAGCGGACCCCCGCCGTTGACGTCAATAGTGACGTATGTTCCCATAGTAACGCCAATAGGGACTTTCCAT    80
CCGCTGGCGGGTCGCCTGGGGGCGGCAACTGCAGTTATCACTGCATACAAGGGTATCATTGCGGTTATCCCTGAAAGGTA
                    |  |  |           |  |                              |
                    26 29 29           29 39                             57
                          30             42

Bgl I           Rsa I        Nde I
TGGAGTATTTACGGTAAACTGCCCACTTGGCAGTACATCAAGTGTATCATATGCCAAGTCCGCCCCC   160
ACTGCAGTTACCCACCTCATAAATGCCATTTGACGGGTGAACCGTCATGTAGTTCACATAGTATACGGTTCAGGCGGGGG
                                                    |               |           |
                                                    114             126         141
Mae II
Aha II
Aat II
TGACGTCAATGGGTGGAGTATTTACGGTAAACTGCCCACTTGGCAGTACATCAAGTGTATCATATGCCAAGTCCGCCCCC
ACTGCAGTTACCCACCTCATAAATGCCATTTGACGGGTGAACCGTCATGTAGTTCACATAGTATACGGTTCAGGCGGGGG
|  |  |
82 82 83
```

```
ScrF I
Nci I
Msp I
Hpa II
Bcn I
  Hae III                                Hinf I              Mae II
Gdi II                          BstU I                 Mae III
Eag I                                                                              616
Eae I
Fnu4H I
|||     •                   •               •       •          •
GCGGCCGGGAACGGTGCATTGGAACGCGGATTCCCCGTGCCAAGAGTGACGTAAGT
CGCCGGCCCTTGCCACGTAACCTTGCGCCTAAGGGGCACGGTTCTCACTGCATTCA
|||     •                   •               •       •          •
561                         585            589      606       609
562
562
563
565
565
565
565
565
```

Restriction Endonucleases site usage

| | | | | | | |
|---|---|---|---|---|---|---|
| Aat II | 4 | BspH I | – | EcoR V | – | Mnl I | – | Rsr II | 3 |
| Acc I | – | BspM I | – | Esp I | – | Msc I | – | Sac I | – |
| Afl II | – | BspM II | – | Fnu4H I | 1 | Mse I | 1 | Sac II | 2 |
| Afl III | – | Bsr I | – | Fok I | 1 | Msp I | 1 | Sal I | – |
| Aha II | 5 | BssH II | – | Fsp I | – | Nae I | – | Sau3A I | – |
| Alu I | 1 | BstB I | – | Gdi II | – | Nar I | 1 | Sau96 I | – |

FIG. 19A-5.

| | | | | | | |
|---|---|---|---|---|---|---|
| Alw I | 1 | BstE II | | Gsu I | 1 | Nci I | 1 | Sca I | - |
| AlwN I | - | BstN I | 1 | Hae I | - | Nco I | - | ScrF I | 3 |
| Apa I | - | BstU I | 2 | Hae II | 1 | Nde I | 1 | Sec I | 2 |
| ApaL I | - | BstX I | - | Hae III | - | Nhe I | - | SfaN I | 1 |
| Ase I | - | BstY I | 1 | Hga I | 2 | Nla III | 2 | Sfi I | - |
| Asp718 | - | Bsu36 I | - | HgiA I | 2 | Nla IV | 2 | Sma I | - |
| Ava I | 1 | Cfr10 I | - | HgiE II | 1 | Not I | 1 | SnaB I | - |
| Ava II | - | Cla I | - | Hha I | - | Nru I | - | Spe I | - |
| Avr II | - | Dde I | - | HinC II | 2 | Nsi I | - | Sph I | 1 |
| BamH I | - | Dpn I | 2 | HinD III | - | Nsp7524 I | - | Spl I | 1 |
| Ban I | 1 | Dra I | - | Hinf I | - | NspB II | 2 | Ssp I | - |
| Ban II | - | Dra III | - | HinP I | 2 | NspH I | 1 | Stu I | - |
| Bbe I | - | Drd I | - | Hpa I | - | Pac I | 1 | Sty I | 1 |
| Bbv I | - | Dsa I | 2 | Hpa II | 2 | PaeR7 I | 2 | Taq I | - |
| Bbv II | - | Eae I | 1 | Hph I | 1 | PflM I | 1 | Tth111 I | 1 |
| Bcl I | - | Eag I | 1 | Kpn I | - | Ple I | 1 | Tth111 II | - |
| Bcn I | 2 | Ear I | - | Mae I | 1 | Pml I | - | Xba I | 1 |
| Bgl I | 2 | Eco47 III | - | Mae II | - | PpuM I | 7 | Xca I | - |
| Bgl II | - | Eco57 I | - | Mae III | - | Pst I | 3 | Xho I | - |
| BsaA I | 1 | EcoN I | - | Mbo I | - | Pvu I | 2 | Xcm I | - |
| Bsm I | - | EcoO109 I | - | Mbo II | - | Pvu II | 1 | Xma I | - |
| BsmA I | 2 | EcoR I | - | Mlu I | - | Rsa I | - | Xmn I | 5 |
| Bsp1286 I | 1 | EcoR II | - | Mme I | 1 | | | | |

| Enzyme | Site | Use | Site position | (Fragment length) | Fragment order |
|---|---|---|---|---|---|
| Alu I | ag/ct | 1 | 1( 471) | 472( 145) | 2 |
| Alw I | ggatc | 1 | 1( 548) | 549( 68) | 2 |
| Ava II | g/gwcc | 1 | 1( 543) | 544( 73) | 2 |
| Ban I | g/gyrcc | 1 4/5 | 1( 372) | 373( 244) | 2 |

FIG. 19A-6.

| Enzyme | Site | | | | | |
|---|---|---|---|---|---|---|
| Ban II | grgcy/c | | 1 | 1( | 470) | 1 | 1( | 146) | 2 | | |
| Bbv II | gaagac | | 1 | 1( | 533) | 1 | 1( | 83) | 2 | | |
| BsaA I | yac/gtr | 2/6 | 1 | 1( | 245) | 2 | 1( | 371) | 1 | | |
| Bsp1286 I | gdgch/c | | 1 | 1( | 470) | 1 | 1( | 146) | 2 | | |
| Bsr I | actgg | 1/-1 | 1 | 1( | 202) | 2 | 1( | 414) | 1 | | |
| BstN I | cc/wgg | | 1 | 1( | 497) | 1 | 1( | 119) | 2 | | |
| Eae I | y/ggccr | | 1 | 1( | 561) | 1 | 1( | 55) | 2 | | |
| Eag I | c/ggccg | | 1 | 1( | 561) | 1 | 1( | 55) | 2 | | |
| EcoR II | /ccwgg | | 1 | 1( | 497) | 1 | 1( | 119) | 2 | | |
| Fnu4H I | gc/ngc | | 1 | 1( | 560) | 1 | 1( | 56) | 2 | | |
| Fok I | ggatg | 9/13 | 1 | 1( | 508) | 1 | 1( | 108) | 2 | | |
| Gdi II | yggccg | -5/-1 | 1 | 1( | 561) | 1 | 1( | 55) | 2 | | |
| Gsu I | ctggag | 16/14 | 1 | 1( | 498) | 1 | 1( | 118) | 2 | | |
| HgiA I | gwgcw/c | | 1 | 1( | 470) | 1 | 1( | 146) | 1 | | |
| Hph I | ggtga | 8/7 | 1 | 1( | 271) | 2 | 1( | 345) | 1 | | |
| Mae I | c/tag | | 1 | 1( | 190) | 2 | 1( | 426) | 2 | | |
| Mbo I | gaaga | 8/7 | 1 | 1( | 533) | 1 | 1( | 83) | 1 | | |
| Nco I | c/catgg | | 1 | 1( | 267) | 2 | 1( | 349) | 2 | | |
| Nde I | ca/tatg | | 1 | 1( | 140) | 2 | 1( | 476) | 1 | | |
| NspB II | cmg/ckg | | 1 | 1( | 558) | 1 | 1( | 58) | 2 | | |
| Ple I | gagtc | 4/5 | 1 | 1( | 317) | 1 | 1( | 299) | 2 | | |
| Sac I | gagct/c | | 1 | 1( | 470) | 1 | 1( | 146) | 2 | | |
| Sac II | ccgc/gg | | 1 | 1( | 558) | 1 | 1( | 58) | 2 | | |
| SfaN I | gcatc | 5/9 | 1 | 1( | 274) | 2 | 1( | 342) | 2 | | |
| SnaB I | tac/gta | | 1 | 1( | 245) | 2 | 1( | 371) | 2 | | |
| Sty I | c/cwwgg | | 1 | 1( | 267) | 2 | 1( | 349) | 1 | | |
| Bcn I | ccs/gg | | 2 | 1( | 540) | 1 | 1( | 24) | 3 | 1( | 565) | 2 |
| Bgl I | gccnnnn/nggc | | 2 | 1( | 113) | 2 | 1( | 441) | 1 | 1( | 555) | 3 |
| BsmA I | gtctc | 1/5 | 2 | 1( | 336) | 1 | 1( | 165) | 2 | 1( | 502) | 3 |
| BstU I | cg/cg | | 2 | 1( | 559) | 1 | 1( | 25) | 3 | 1( | 585) | 2 |
| Dpn I | ga/tc | | 2 | 1( | 560) | 1 | 1( | 56) | 3 | 1( | 549) | 2 |
| Dsa I | c/crygg | | 2 | 1( | 492) | 1 | 1( | 291) | 1 | 1( | 559) | 3 |
| Hae III | gg/cc | | 2 | 1( | 267) | 2 | 1( | 379) | 1 | 1( | 563) | 3 |
| Hga I | gacgc | 5/10 | 2 | 1( | 424) | 1 | 1( | 79) | 3 | 1( | 504) | 2 |

FIG. 19A-7.

| Enzyme | Site | | | | | | | | |
|---|---|---|---|---|---|---|---|---|---|
| HinC II | gty/rac | 2 | 1( 25) 3 | 26( 396) 1 | 422( 195) 2 |
| Hinf I | g/antc | 2 | 1( 317) 1 | 318( 271) 2 | 589( 28) 3 |
| Hpa II | c/cgg | 2 | 1( 540) 1 | 541( 24) 3 | 565( 52) 2 |
| Mbo I | /gatc | 2 | 1( 492) 1 | 493( 56) 3 | 549( 68) 2 |
| Msp I | c/cgg | 2 | 1( 540) 1 | 541( 24) 3 | 565( 52) 2 |
| Nci I | cc/sgg | 2 | 1( 540) 1 | 541( 24) 3 | 565( 52) 2 |
| Nla III | catg/ | 2 | 1( 208) 2 | 209( 60) 3 | 269( 348) 1 |
| Nla IV | ggn/ncc | 2 | 1( 372) 1 | 373( 170) 2 | 543( 74) 3 |
| Sau3A I | /gatc | 2 | 1( 492) 2 | 493( 56) 3 | 549( 68) 2 |
| Sau96 I | g/gncc | 2 | 1( 183) 2 | 184( 360) 1 | 544( 73) 3 |
| Sec I | c/cnngg | 2 | 1( 267) 2 | 268( 291) 1 | 559( 58) 3 |
| Mae III | /gtnac | 3 | 1( 38) 2 | 39( 18) 3 | 57( 549) 1 |
| | | | 606( 11) 4 | | |
| Mnl I | cctc | 3 | 1( 455) 1 | 456( 70) 2 | 526( 30) 4 |
| | | 7/7 | 556( 61) 3 | | |
| ScrF I | cc/ngg | 3 | 1( 497) 1 | 498( 43) 3 | 541( 24) 4 |
| | | | 565( 52) 2 | | |
| Aat II | gacgt/c | 4 | 1( 28) 5 | 29( 53) 4 | 82( 83) 3 |
| | | | 165( 186) 2 | 351( 266) 1 | |
| Aha II | gr/cgyc | 5 | 1( 28) 6 | 29( 53) 5 | 82( 83) 4 |
| | | | 165( 186) 1 | 351( 153) 2 | 504( 113) 3 |
| Rsa I | gt/ac | 5 | 1( 125) 3 | 126( 80) 4 | 206( 33) 6 |
| | | | 239( 51) 5 | 290( 157) 2 | 447( 170) 1 |
| Mae II | a/cgt | 7 | 1( 29) 6 | 30( 12) 7 | 42( 41) 5 |
| | | | 83( 83) 3 | 166( 81) 4 | 247( 105) 2 |
| | | | 352( 257) 1 | 609( 8) 8 | |

98 sites found

No Sites found for the following Restriction Endonucleases

| Acc I | gt/mkac | Dra III | cacnnn/gtg | Nsp7524 I | r/catgy |

FIG. 19A-8.

| Enzyme | Site | Enzyme | Site | Enzyme | Site |
|---|---|---|---|---|---|
| Afl II | c/ttaag | Drd I | gacnnnn/nngtc 1/4 | NspH I | rcatg/y |
| Afl III | a/crygt | Ear I | ctcttc | Pac I | ttaat/taa |
| AlwN I | cagnnn/ctg | Eco47 III | agc/gct | PaeR7 I | c/tcgag |
| Apa I | gggcc/c | Eco57 I | ctgaag 16/14 | Pf1M I | ccannnn/ntgg |
| ApaL I | g/tgcac | EcoN I | cctnn/nnagg | Pml I | cac/gtg |
| Ase I | at/taat | EcoO109 I | rg/gnccy | PpuM I | rg/gwccy |
| Asp718 | g/gtacc | EcoR I | g/aattc | Pst I | ctgca/g |
| Ava I | c/ycgrg | EcoR V | gat/atc | Pvu I | cgat/cg |
| Avr II | c/ctagg | Esp I | gc/tnagc | Pvu II | cag/ctg |
| BamH I | g/gatcc | Fsp I | tgc/gca | Rsr II | cg/gwccg |
| Bbe I | ggcgc/c | Hae I | wgg/ccw | Sal I | g/tcgac |
| Bbv I | gcagc 8/12 | Hae II | rgcgc/y | Sca I | agt/act |
| Bcl I | t/gatca | HgiE II | accnnnnnnggt | Sfi I | ggccnnnn/nggcc |
| Bgl II | a/gatct | Hha I | gcg/c | Sma I | ccc/ggg |
| Bsm I | gaatgc 1/-1 | HinD III | a/agctt | Spe I | a/ctagt |
| BspH I | t/catga | HinP I | g/cgc | Sph I | gcatg/c |
| BspM I | acctgc 4/8 | Hpa I | gtt/aac | Spl I | c/gtacg |
| BspM II | t/ccgga | Kpn I | ggtac/c | Ssp I | aat/att |
| BssH II | g/cgcgc | Mlu I | a/cgcgt | Stu I | agg/cct |
| BstB I | tt/cgaa | Mme I | tccrac 20/18 | Taq I | t/cga |
| BstE II | g/gtnacc | Msc I | tgg/cca | Tth111 I | gacn/nngtc |
| BstX I | ccannnnn/ntgg | Mse I | t/taa | Tth111 II | caarca 11/9 |
| BstY I | r/gatcy | Nae I | gcc/ggc | Xba I | t/ctaga |
| Bsu36 I | cc/tnagg | Nar I | gg/cgcc | Xca I | gta/tac |
| Cfr10 I | r/ccggy | Nhe I | g/ctagc | Xho I | c/tcgag |
| Cla I | at/cgat | Not I | gc/ggccgc | Xcm I | ccannnnn/nnnntgg |
| Dde I | c/tnag | Nru I | tcg/cga | Xma I | c/ccggg |
| Dra I | ttt/aaa | Nsi I | atgca/t | Xmn I | gaann/nnttc |

FIG. 19A-9.

```
*** Aligned sequences:
C1 ( 1f):  |>u 1>+++++ ad169hcmv   (930 bases)+++++>u 930>|
C2 ( 1f):  |>u 1>+++++ townehcmv   (616 bases)+++++>u 616>|

*** Alignment of first sequence with all others displayed
*** Key:
    UPPER CASE = aligned non-identical bases
    lower case = unaligned bases
    ---------- = aligned identical bases
    .......... = gap ad169hcmv : AATCAATATATTGGCCATTAGCCATATATTATTCATTGGTTATATAGCATAAATCAATATTGGC
townehcmv : ................................................................

ad169hcmv : TATTGGCCATTGCATACGTTGTATCCATATCATAATATGTACATTTATATTGGCTCATGT
townehcmv : ............................................................

ad169hcmv : CCAACATTACCGCCATGTTGACATTGATTATTGACTAGTTATTAATAGTAATCAATTACG
townehcmv : ............................................................

ad169hcmv : GGGTCATTAGTTCATAGCCCATATATGGAGTTCCGCGTTACATAACTTACGGTAAATGGC
townehcmv : ............................................................

ad169hcmv : CCGCCTGGCTGACCGCCCAACGACCCCCGCCCATTGACGTCAATAATGACGTATGTTCCC
townehcmv : ..........................-------G--------G----------------- ad169hcmv : ATAGTAACGCCAATAGGGACTTTCCATTGACGTCAATGGGTGGAGTATTTACGGTAAACT
townehcmv : ------------------------------------------------------------

FIG. 19B-1.
```

```
ad169hcmv  : GCCCACTTGGCAGTACATCAAGTGTATCATATGCCAAGTACGCCCCCTATTGACGTCAAT
townehcmv  : -----------------------------------C------------------------ ad169hcmv  : GACGGTAAATGGCCCGCCTGGCATTATGCCCAGTACATGACCTTATGGGACTTTCCTACT
townehcmv  : -----------------A--------------------C--------------------- ad169hcmv  : TGGCAGTACATCTACGTATTAGTCATCGCTATTACCATGGTGATGCGGTTTTGGCAGTAC
townehcmv  : ------------------------*----------------------------------- ad169hcmv  : ATCAATGGGCGTGGATAGCGGTTTGACTCACGGGGATTTCCAAGTCTCCACCCCATTGAC
townehcmv  : --C--------------------------------------------------------- ad169hcmv  : GTCAATGGGAGTTTGTTTTGGCACCAAAATCAACGGGACTTTCCAAAATGTCGTAACAAC
townehcmv  : ----------------------------------------------------T------- ad169hcmv  : TCCGCCCCATTGACGCAAATGGGCGGTAGGCGTGTACGGTGGGAGGTCTATATAAGCAGA
townehcmv  : C------G---------------------------------------------------- ad169hcmv  : GCTCGTTTAGTGAACCGTCAGATCGCCTGGAGACGCCATCCACGCTGTTTTGACCTCCAT
townehcmv  : ------------------------------------------------------------ ad169hcmv  : AGAAGACACCGGGACCGATCCAGCCTCCGCGGCCGGGAACGGTGCATTGGAACGCGGATT
townehcmv  : ------------------------------------------------------------ ad169hcmv  : CCCCGTGCCAAGAGTGACGTAAGTACCGCCTATAGAGTCTATAGGCCCACCCCCTTGGCT
townehcmv  : ....................................................

ad169hcmv  : TCTTATGCATGCTATACTGTTTTTGGCTTG
townehcmv  : ..............................
```

FIG. 19B-2.

```
LOCUS       HS5IEE        930 bp ds-DNA            VRL       15-SEP-1989
DEFINITION  Human cytomegalovirus major immediate-early gene, enhancer.
ACCESSION   K03104
KEYWORDS    major immediate-early gene.
SOURCE      HCMV strain AD169.
  ORGANISM  Human cytomegalovirus
            Viridae; ds-DNA enveloped viruses; Herpesviridae;
            Betaherpesvirinae.
REFERENCE   1 (bases 1 to 930)
  AUTHORS   Boshart,M., Weber,F., Jahn,G., Dorsch-Haesler,K.,
            Fleckenstein,B. and Schaffner,W.
  TITLE     A very strong enhancer is located upstream of an immediate
            early gene of human cytomegalovirus
  JOURNAL   Cell 41, 521-530 (1985)
  STANDARD  full automatic
REFERENCE   2 (sites)
  AUTHORS   Zhang,X.-Y., Inamdar,N.M., Supakar,P.C., Wu,K., Ehrlich,M.
            and Ehrlich,K.C.
  TITLE     three MDBP sites in the immediate-early enhancer-promoter
            region of human cytomegalovirus
  JOURNAL   Virology 182, 865-869 (1991)
  STANDARD  full automatic
COMMENT     Draft entry and printed copy of sequence in [1] were kindly
            provided by M.Boshart, 24-OCT-1985.
            The sequence shown is a 930 bp segment of the PstI m-fragment
            from HCMV strain AD169.  The enhancer region of the HCMV gene
```

FIG. 19B-3.

was defined by selecting for fragments of HCMV DNA that would
restore efficient growth of enhancerless SV40.

FEATURES          Location/Qualifiers
    misc_signal   214..620
                  /note="HCMV IE enhancer region"
    mRNA          738..>930
                  /note="HCMV IE mRNA"

BASE COUNT    233 A    228 C    211 G    258 T

ORIGIN    12 bp upstream of BalI site; .750 mu.
  1 AATCAATATT GGCCATTAGC CATATTATTC ATTGGTTATA TAGCATAAAT CAATATTGGC
 61 TATTGGCCAT TGCATACGTT GTATCCATAT CATAATATGT ACATTTATAT TGGCTCATGT
121 CCAACATTAC CGCCATGTTG ACATTGATTA TTGACTAGTT ATTAATAGTA ATCAATTACG
181 GGGTCATTAG TTCATAGCCC ATATATGGAG TTCCGCGTTA CATAACTTAC GGTAAATGGC
241 CCGCCTGGCT GACCGCCCAA CGACCCCCGC CCATTGACGT CAATAATGAC GTATGTTCCC
301 ATAGTAACGC CAATAGGGAC TTTCCATTGA CGTCAATGGG TGGAGTATTT ACGGTAAACT
361 GCCCACTTGG CAGTACATCA AGTGTATCAT ATGCCAAGTA CGCCCCCTAT TGACGTCAAT
421 GACGGTAAAT GGCCCGCCTG GCATTATGCC CAGTACATGA CCTTATGGGA CTTTCCTACT
481 TGGCAGTACA TCTACGTATT AGTCATCGCT ATTACCATGG TGATGCGGTT TTGGCAGTAC
541 ATCAATGGGC GTGGATAGCG GTTTGACTCA CGGGGATTTC CAAGTCTCCA CCCCATTGAC
601 GTCAATGGGA GTTTGTTTTG GCACCAAAAT CAACGGGACT TTCCAAAATG TCGTAACAAC
661 TCCGCCCCAT TGACGCAAAT GGGCGGTAGG CGTGTACGGT GGGAGGTCTA TATAAGCAGA
721 GCTCGTTTAG TGAACCGTCA GATCGCCTGG AGACGCCATC CACGCTGTTT TGACCTCCAT
781 AGAAGACACC GGGACCGATC CAGCCTCCGC GGCCGGGAAC GGTGCATTGG AACGCGGATT
841 CCCCGTGCCA AGAGTGACGT AAGTACCGCC TATAGAGTCT ATAGGCCCAC CCCCTTGGCT
901 TCTTATGCAT GCTATACTGT TTTTGGCTTG

FIG. 19B-4.

```
LOCUS       HS5MIE1       616 bp ds-DNA       VRL       15-SEP-1989
DEFINITION  Human cytomegalovirus (Towne) major immediate-early (IE)
            gene, exon 1.
ACCESSION   K01484 K01090
KEYWORDS    major immediate-early gene.
SEGMENT     1 of 4
SOURCE      Human cytomegalovirus (strain Towne) passed in primary human
            foreskin fibroblasts, DNA [1], clone pXEP22 [2].
ORGANISM    Human cytomegalovirus
            Viridae; ds-DNA enveloped viruses; Herpesviridae;
            Betaherpesvirinae.
REFERENCE   1  (bases 460 to 616)
AUTHORS     Stenberg,R.M., Thomsen,D.R. and Stinski,M.F.
TITLE       Structural analysis of the major immediate early gene of
            human cytomegalovirus
JOURNAL     J. Virol. 49, 190-199 (1984)
STANDARD    full automatic
REFERENCE   2  (bases 1 to 490)
AUTHORS     Thomsen,D.R., Stenberg,R.M., Goins,W.F. and Stinski,M.F.
TITLE       Promoter-regulatory region of the major immediate early gene
            of human cytomegalovirus
JOURNAL     Proc. Natl. Acad. Sci. U.S.A. 81, 659-663 (1984)
STANDARD    full automatic
```

FIG. 19B-5.

COMMENT    IE region 1 gene is also known as the major IE gene.
Cytomegalovirus immediate-early gene expression is dominated
in vivo by the expression of a single gene. At least three
promoters influence transcription of the virus after
infection. When a complete set of promoter-regulatory
regions were present (IE regions 1, 2 and 3 or IE region 1
and an adenovirus major late promoter), transcription was
qualitatively higher from IE region 1.

Based on these data, [1] proposes that the upstream sequence
of the IE region 1 gene competes more efficiently for RNA
polymerase II or other host cell proteins necessary for in
vitro transcription.

Consensus CAAT and TATA boxes were found at positions 429-433
and 462-467, a polyadenylation signal was found at positions
2198-2203.

Fourteen direct repeats were found in the promoter-regulatory
region (four 16-bp repeats, four 18-bp repeats, four 19-bp
repeats and two 21-bp repeats).

Draft entry and clean copy sequences [1], [2] kindly provided
by P.R. Witte and M.F. Stinski (10-FEB-1986].

FIG. 19B-6.

```
FEATURES             Location/Qualifiers
     prim_transcript 490..>616
                     /note="major IE mRNA"
     intron          611..>616
                     /note="major IE mRNA intron A"
BASE COUNT    144 A    165 C    162 G    145 T
ORIGIN      28 bp upstream of HincII site; 0.752 map units.
    1 GGGGACCGCC CAGGGACCCC CGCCCGTTGA CGTCAATAGT GACGTATGTT CCCATAGTAA
   61 CGCCAATAGG GACTTTCCAT TGACGTCAAT GGGTGGAGTA TTTACGGTAA ACTGCCCACT
  121 TGGCAGTACA TCAAGTGTAT CATATGCCAA GTCCGCCCCC TATTGACGTC AATGACGGTA
  181 AATGGCCCGC CTAGCATTAT GCCCAGTACA TGACCTTACG GGAGTTTCCT ACTTGGCAGT
  241 ACATCTACGT ATTAGTCATC GCTATTACCA TGGTGATGCG GTTTTGGCAG TACACCAATG
  301 GGCGTGGATA GCGGTTTGAC TCACGGGGAT TTCCAAGTCT CCACCCCATT GACGTCAATG
  361 GGAGTTTGTT TTGGCACCAA AATCAACGGG ACTTTCCAAA ATGTCGTAAT AACCCCGCCC
  421 CGTTGACGCA AATGGGCGGT AGGCGTGTAC GGTGGGAGGT CTATATAGCA GAGCTCGTTT
  481 AGTGAACCGT CAGATCGCCT GGAGACGCCA TCCACGCTGT TTTGACCTCC ATAGAAGACA
  541 CCGGGACCGA TCCAGCCTCC GCGGCCGGGA ACGGTGCATT GGAACGCGGA TTCCCCGTGC
  601 CAAGAGTGAC GTAAGT
```

FIG. 19B-7.

HCMV (AD169) -> Full Restriction Map

DNA sequence    930 b.p.    aatcaatattgg ... gtttttggcttg    linear

Positions of Restriction Endonucleases sites (unique sites underlined)

```
         Hae III                                                Hae III
         Msc I                                                  Msc I
         Hae I                                                  Hae I
         Eae I                                                  Eae I         Mae II
Ssp I    | |                                          Ssp I    | |           |
 |       | |                                           |       | |           |
AATCAATATATTGGCCATTAGCCATATATTCATTGGTTATATAGCATAAATCAATATTGGCTATTGGCCATTGCATACGTT
TTAGTTATATAACCGGTAATCGGTATATAAGTAACCAATATATCGTATTAGTTATAACCGATAACCGGTAACGTATGCAA
 |        | | |                                                              |
 5        1 1 1                                                              7
          0 0 0                                                              6
            1                                                                
                                                                 6
                                                                 4
                                                                 6
                                                                 4
                                                                 6
                                                                 5
```

```
                                    Mme I                               Mae I
                                    Nla III                HinC II      Spe I
                       Rsa I        | |            Nla III | |          | |
                       |            | |            |       | |          | |
GTATCCATATCATAATATGTACATTTATATTGGCTCATGTCCAACATTACCGCCATGTTGACATTGATTATTGACTAGTT
CATAGGTATAGTATTATACATGTAAATATAACCGAGTACAGGTTGTAATGGCGGTACAACTGTAACTAATAACTGATCAA
                       |            | |            |       | |          | |
                       9            1 1            1       1 1          1 1
                       9            1 2            3       3 3          5 5
                                    6 0            4       7 4          4 5
```

FIG. 19C-1.

```
                                                                Bgl I
                                      Mae III                   Sau96 I
                                      BstU I                    Hae III
                                       |                         |
ATTAATAGTAATCAATTACGGGGTCATTAGTTCATAGCCCATATATGGAGTTCCGCGTTACATAACTTACGGTAAATGGC  240
TAATTATCATTAGTTAATGCCCCAGTAATCAAGTATCGGGTATATACCTCAAGGCGCAATGTATTGAATGCCATTTACCG
      |                                                 |      |
      161                                                214    238
      162                                                217    238
                                                                239

ScrF I                                       Mae II
EcoR II                                      Aha II                        Mae III
BstN I                                       Aat II                         |
 |                                            |
CCGCCTGCTGACCGCCCAACGACCCCCGCCCATTGACGTCAATAATGACGTATGTTCCCATAGTAACGCCAATAGGGAC  320
GGCGGACGACTGGCGGGTTGCTGGGGGCGGGTAACTGCAGTTATTACTGCATACAAGGGTATCATTGCGGTTATCCCTG
 |                                            |                   |
 244                                           276                 304
 244                                           276
 244                                           277

Mae II
   Aha II                          Bgl I              Rsa I              Nde I              Rsa I
   Aat II                           |                  |                  |                  |
TTTCCATTGACGTCAATGGGGTGGAGTATTTACGGTAAACTGCCCACTTGGCAGTACATCAAGTGTATCATATGCCAAGTA  400
AAAGGTAACTGCAGTTACCCCACCTCATAAATGCCATTTGACGGGTGAACCGTCATGTAGTTCACATAGTATACGGTTCAT
 |                                  |                  |                  |
 329                                361                373                388        398
 329
 330
```

```
                                                                                        Alu I
                                                                                        Sac I
                        Mae II                                                          HgiA I
             BsmA I     Aha II                                   Nla IV                 Bsp1286 I
Ple I                   Aat II                                   Ban I                  Ban II
Hinf I      |           | |                                      |                      ||
|           |           | |                                      |                      ||
GTTTGACTCAACGGGGATTTCCAAGTCTCCACCCCATTGACGTCAAATGGGAGTTTGTTTTTGGCACCAAAATCAACGGGACT 640
CAAACTGAGTTGCCCCTAAAGGTTCAGAGGTGGGGTAACTGCAGTTTACCCTCAAACAAAACCGTGGTTTTAGTTGCCCTGA
565         584                             598                 620
565                                         598                 620
                                            599
```

```
                                                 Rsa I     Mnl I
           Mae III              Hga I            |         |
           |                    |                |         |
TTCCAAAATGTCGTAACAACTCCGCCCCATTGACGCAAATGGGCGGTAGGCGTGTACGGTGGGAGGTCTATATATAAGCAGA
AAGGTTTTACAGCATTGTTGAGGCGGGGTAACTGCGTTTACCCGCCATCCGCACATGCCACCCTCCAGATATATATTCGTCT
653                             672              694       703                    719
                                                                                   719
                                                                                   719
                                                                                   719
                                                                                   720
                                                                                   720
```

```
              BstX I                          Nla III
     Sau96 I  Sty I                           Sph I
     Hae III  Sec I                           NspH I
       |        |                             Nsp7524 I
       |        |                              Nsi I
       |        |                              | | |
ATAGGCCCACCCCCTTGGCTTCTTATGCATGCTATACTGTTTTTGGCTTG  930
TATCCGGGTGGGGGGAACCGAAGAATACGTACGATATGACAAAAACCGAAC
    ·       ·       ·       ·       ·
   884     893     905                        
   884     893     907
   887             907
                   908
```

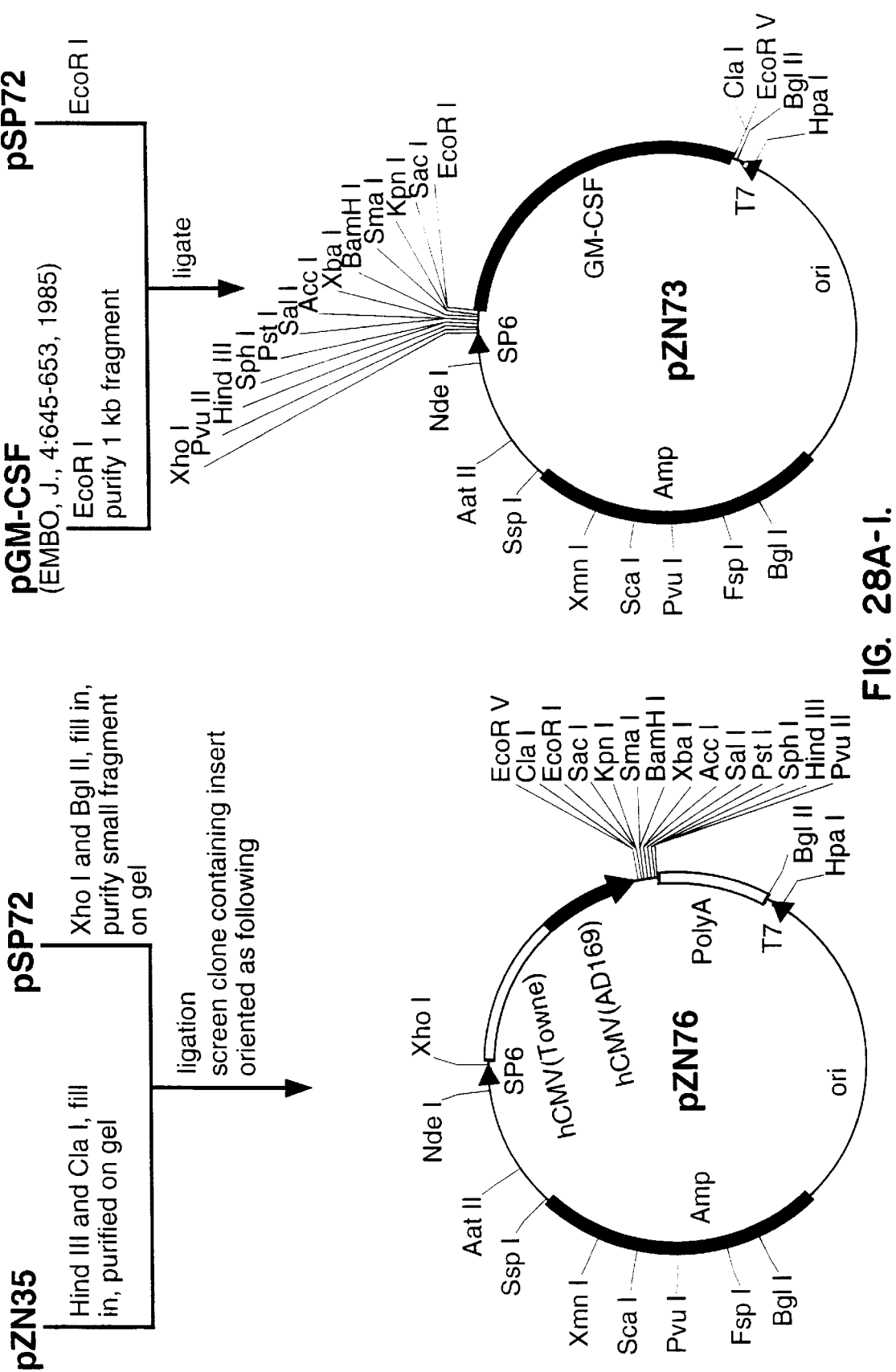
FIG. 28A-I.

MAMMALIAN TRANSFORMATION COMPLEX COMPRISING A LIPID CARRIER AND DNA ENCODING CFTR

This 371 application claims the benefit of PCT/US92/11004, filed Dec. 17, 1992, which is a CIP of application U.S. Ser. No. 07/972,135, filed Nov. 5, 1992, now U.S. Pat. No. 5,858,784, which is a CIP of application U.S. Ser. No. 07/809,291, filed Dec. 17, 1991, now abandoned. PCT/US92/11004, filed Dec. 17, 1992, is also a CIP of application U.S. Ser. No. 07/927,200, filed Aug. 6, 1992, now abandoned, which is a CIP of application U.S. Ser. No. 07/894,498, filed Jun. 4, 1992, now abandoned.

TECHNICAL FIELD

The present invention relates to methods and compositions for producing a transgenic mammal which comprises exogenously supplied nucleic acid coding for a molecule having cystic fibrosis transmembrane conductance regulator activity. The nucleic acid is supplied by aerosolized delivery, particularly to the airways and alveoli of the lung, or by systemic delivery.

BACKGROUND

Many genetic diseases are caused by the absence or mutation of the appropriate protein, for example as a result of deletions within the corresponding gene. One of the most common fatal genetic diseases in humans is cystic fibrosis (CF). Cystic fibrosis (CF), a spectrum of exocrine tissue dysfunction, which eventually leads to respiratory failure and death results from a mutation of the cystic fibrosis transmembrane conductance regulator (CFTR) gene. The CFTR gene has now been to chromosome 7q31, and cloned. A 3 bp deletion, resulting in the loss of a phenylalanine residue at amino acid position 508, is present in approximately 70% of CF chromosomes, but is not seen on normal chromosomes. The other 30% of CF mutations are heterogeneous and include deletion, missense, and splice-site mutations. Transfection of even a single normal copy of the CFTR gene abolishes the CF secretory defect in CF cell lines, an observation which supports the feasibility of gene therapy for CF. These results demonstrate that expression of a wild-type CFTR transgene can exert a dominant positive effect in CF cells which concurrently express an endogenous mutant CFTR gene. Thus, expression of the wild-type CFTR transgene in the lungs of CF patients can correct the CF phenotype. However, to date, the inability to produce high level expression of transgenes in the lung by either aerosol or intravenous (iv) administration has precluded the use of gene therapy for the treatment of CF. Expression of a wild-type CFTR transgene in cells from CF patients corrects the chloride secretory defect, the primary biochemical lesion of CF. Chloride secretion is normalized in cells of CF patients despite the presence of the mutant CFTR protein, indicating that when wild-type and mutant CFTR proteins are coexpressed in cells, the wild-type CFTR is dominant.

To date, attempts to replace absent or mutated genes in human patients have relied on ex vivo techniques. Ex vivo techniques include, but are not limited to, transformation of cells in vitro with either naked DNA or DNA encapsulated in liposomes, followed by introduction into a suitable host organ ("ex vivo" gene therapy). The criteria for a suitable organ include that the target organ for implantation is the site of the relevant disease, the disease is easily accessible, that it can be manipulated in vitro, that it is susceptible to genetic modification methods and ideally, it should contain either non-replicating cells or cycling stem cells to perpetuate a genetic correction. It also should be possible to reimplant the genetically modified cells into the organism in a functional and stable form. A further requirement for ex vivo gene therapy, if for example a retroviral vector is used, is that the cells be pre-mitotic; post-mitotic cells are refractory to infection with retroviral vectors. There are several drawbacks to ex vivo therapy. For example, if only differentiated, replicating cells are infected, the newly introduced gene function will be lost as those cells mature and die. Ex vivo approaches also can be used to transfect only a limited number of cells and cannot be used to transfect cells which are not first removed from the body. Exemplary of a target organ which meets the criteria of in vivo gene transfer is mammalian bone marrow; mammalian lung is not a good candidate for ex vivo therapy.

Retroviruses, adenoviruses and liposomes have been used in animal model studies in attempts to increase the efficiency of gene transfer. Liposomes have been used effectively to introduce drugs, radiotherapeutic agents, enzymes, uses, transcription factors and other cellular effect into a variety of cultured cell lines and animals. In addition, successful clinical trials examining the effectiveness of liposome-mediated drug delivery have been completed. Several strategies have been devised to increase the effectiveness of liposome-mediated drug delivery by targeting liposomes to specific tissues and specific cell types. However, while the basic methodology for using liposome-mediated vectors is well developed, the technique has not been perfected for liposome-based transfection vectors for in vivo gene therapy. In the studies published to date, injection of the vectors either intravenously, intratracheally or into specific tissues has resulted in low but demonstrable expression, but the expression has generally been limited to one tissue, typically either the tissue that was injected (for example muscle); liver or lung where iv injection has been used; or lung where intratracheal injection has been used, and less than 1% of all cells within these tissues were transfected.

In vivo expression of transgenes has been restricted to injection of transgenes directly into a specific tissue, such as direct intratracheal, intramuscular or intraarterial injection of naked DNA or of DNA-cationic liposome complexes, or to ex vivo transfection of host cells, with subsequent reinfusion. Currently available gene delivery strategies consistently have failed to produce a high level and/or generalized transgene expression in vivo. Expression of introduced genes, either complexed to cationic vectors or packaged in adenoviral vectors has been demonstrated in the lungs of rodents after intratracheal (IT) instillation. However, IT injection is invasive and produces a non-uniform distribution of the instilled material; it also is too invasive to be performed repeatedly in humans. For CF patients wherein the defect is a primary life-threatening defect in the lung, it would be of interest to develop a non-invasive delivery technique which also results in deeper penetration of exogenous nucleic acid constructs into the lung than do other methods, and can be used to deposit the CFTR gene constructs throughout the distal airways, as well as transfecting both airway epithelial cell and airway sub-mucosal cell types. Where other organs in the CF patient are affected due to the presence of mutant CFTR gene, techniques for transformation of a wide variety of tissues would be of interest, in order to alleviate extrapulmonary organ dysfunction in CF patients.

Relevant Literature

EP 91301819.8 (publication number 0 446 017 A1) discloses full length isolated DNAs encoding cystic fibrosis transmembrance conductance regulator (CFTR) protein and a variety of mutants thereof. Transient expression of CFTR in transformed cultured COS-7 cells is also disclosed. Rich et al., *Nature* (1990) 347:358–363 and Gregory et al., *Nature* (1990) 347:382–386 disclosed expression of the cystic fibrosis transmembrane conductance regulator in cultured HeLa cells using a vaccinia virus vector. Yoshimura et al. disclose expression of the CFTR gene in mouse lung after intracheal administration of a plasmid containing the gene, either as naked DNA or complexed to lipofectin.

Brigham et al., *Am. J. Med. Sci.* (1989) 22:278–281, describes the in vivo transfection of murine lungs with the CAT gene using a liposome vehicle. Transfection was accomplished by intravenous, intracheal or intraperitoneal injection. Both intravenous and intratracheal administration resulted in the expression of the CAT gene in the lungs. However, intraperitoneal administration did not. See, also Werthers, *Clinical Research* (1991) 39:(Abstract).

Canonico et al., *Clin. Res.* (1991) 39:219A describes the expression of the human $\alpha$-1 antitrypsin gene, driven by the CMV promoter, in cultured bovine lung epithelial cells. The gene was added to cells in culture using cationic liposomes. The experimenters also detected the presence of $\alpha$-1 antitrypsin in histological sections of the lung of New Zealand white rabbits following the intravenous delivery of gene constructs complexed to liposomes. Yoshimura et al. disclose expression of the human cystic fibrosis transmembrane conductance regulator gene in mouse lung after intratracheal plasmid-mediated gene transfer.

Multiple approaches for introducing functional new genetic material into cells, both in vitro and in vivo have been attempted (Friedmann (1989) *Science*, 244:1275–1280). These approaches include integration of the gene to be expressed into modified retroviruses (Friedmann (1989) supra; Rosenberg (1991) *Cancer Research* 51(18), suppl.: 5074S–5079S); integration into non-virus vectors (Rosenfeld, et al. (1992) *Cell*, 68:143–155; Rosenfeld, et al. (1991) *Science*, 252:431–434); or delivery of a transgene linked to a heterologous promoter-enhancer element via liposomes (Friedmann (1989), supra; Brigham, et al. (1989) *Am. J. Med. Sci.*, 298:278–281; Nabel, et al. (1990) *Science*, 249:1285–1288; Hazinski, et al. (1991) *Am. J. Resp. Cell Molec. Biol.*, 4:206–209; and Wang and Huang (1987) *Proc. Natl. Acad. Sci. (USA)*, 84:7851–7855); coupled to ligand-specific, cation-based transport systems (Wu and Wu (1988) *J. Biol. Chem.*, 263:14621–14624) or the use of naked DNA expression vectors (Nabel et al. (1990), supra); Wolff et al. (1990) *Science*, 247:1465–1468). Direct injection of transgenes into tissue produces only localized expression (Rosenfeld (1992) supra); Rosenfeld et al. (1991) supra; Brigham et al. (1989) supra; Nabel (1990) supra; and Hazinski et al. (1991) supra). The Brigham et al. group (*Am. J. Med. Sci.* (1989) 298:278–281 and *Clinical Research* (1991) 39 (abstract)) have reported in vivo transfection only of lungs of mice following either intravenous or intratracheal administration of a DNA liposome complex. An example of a review article of human gene therapy procedures is: Anderson, *Science* (1992) 256:808–813.

PCT/US90/01515 (Felgner et al.) is directed to methods for delivering a gene coding for a pharmaceutical or immunogenic polypeptide to the interior of a cell of a vertebrate in vivo. Expression of the transgenes is limited to the tissue of injection. PCT/US90/05993 (Brigham) is directed to a method for obtaining expression of a transgene in mammalian lung cells following either iv or intratracheal injection of an expression construct. PCT 89/02469 and PCT 90/06997 are directed to ex vivo gene therapy, which is limited to expressing a transgene in cells that can be taken out of the body such as lymphocytes. PCT 89/12109 is likewise directed to ex vivo gene therapy. PCT 90/12878 is directed to an enhancer which provides a high level of expression both in transformed cell lines and in transgenic mice using ex vivo transformation.

Debs et al. disclose pentamidine uptake in the lung by aerosolization and delivery in liposomes. *Am Rev Respir Dis* (1987) 135: 731–737. For a review of the use of liposomes as carriers for delivery of nucleic acids, see, Hug and Sleight, *Biochim. Biophys. Acta.* (1991) 1097:1–17; Straubinger et al., in *Methods of Enzymology* (1983), Vol. 101, pp. 512–527.

SUMMARY

Methods and compositions are provided for producing a mammal which comprises exogenously supplied nucleic acid encoding a molecule having the biological activity of wild type cystic fibrosis transmembrane conductance regulator (CFTR) in its lung cells. The nucleic acid may be either a sense or an antisense strand of DNA. Also provided is a transgenic mammal comprising the CFTR nucleic acid. The method includes the steps of contacting host cells in vivo with a construct comprising said nucleic acid in an amount sufficient to transform cells contacted by the construct. The exogenously supplied nucleic acid generally is provided in a transcription cassette or an expression cassette and includes the coding sequence for a CFTR molecule operably joined to regulatory sequences functional in the mammal. The methods and compositions find use particularly for in vivo gene therapy of cystic fibrosis.

BRIEF DESCRIPTION OF THE FIGURES

FIGS. 1A–1E shows photomicrograph of frozen sections from lungs of control mice (FIGS. 1B and 1D) and mice treated with a plasmid containing the human CFTR gene (pZN32) complexed to DDAB:cholesterol (1:1) liposomes (FIGS. 1A, 1C, and 1E). FIGS. 1A, 1C, and 1E are lung sections from treated mice at 50×, 100×, and 250× magnification, respectively. FIGS. 1B and 1D are lung sections from untreated (control) mice at 50× and 100× magnification. Lipid carriers were 1 to 1 molar DDAB:Chol (SUV). Lipid carrier-DNA complexes were 5 nanomoles cationic lipid to 1 µg DNA.

FIGS. 4A–D shows an electron micrograph which demonstrates that cationic lipid carrier: DNA complexes (DOTMA:DOPE:pRSV-CAT) are internalized by cells via classical receptor-mediated endocytosis following binding to cell sue receptors. Lipid carriers were 1:1 DOTMA:DOPE. 20 µg DNA was complexed with 20 nmoles cation lipid.

FIG. 6A shows analysis of lung, spleen, liver and heart two days following iv injection with either lipid carrier alone (lanes 1–4) or lipid carrier plus DNA (lanes 5–8); FIG. 6B shows the results at six days in mouse lung, spleen, liver and heart (lanes as in 6A. Lipid carriers were DOTMA:DOPE 1 to 1 molar. Cationic lipid to DNA ratio was 4 nanomoles to 1 µg. 100 µg DNA was injected per mouse. In both figures the chromatograph runs from bottom to top.

FIGS. 8(A–B) shows CAT gene expression in the indicated tissues following intravenous injection with pZN27 alone or pZN27:DDAB:Chol SUV complexes. In FIG. 8A lanes 1–20 the chromatograph runs from bottom to top; in FIG. 8A lanes 21–40 the chromatograph runs from top to bottom.

FIGS. 12(A–C). FIG. 12B shows the construction of intermediate plasmids pZN52, pZN54, pZN56 and pZN58.

FIGS. 19(A–C) shows a full restriction map for HCMV (Towne) of the immediate early enhancer and promoter region of HCMV (Towne) in FIG. 19A SEQ ID NO: 1 and HCMV(AD169) in FIG. 19C SEQ ID NO: 2. FIG. 19B SEQ ID NOS.: 2 and 3 shows a sequence comparison of the two HCMV promoters. The sequence of the Towne strain is designated as hs5miel on this comparison. The position of the NcoI site is indicated by an asterisk.

FIGS. 27(A–B).

FIGS. 28(A–B).

DESCRIPTION OF THE SPECIFIC EMBODIMENTS

Figure 1A:
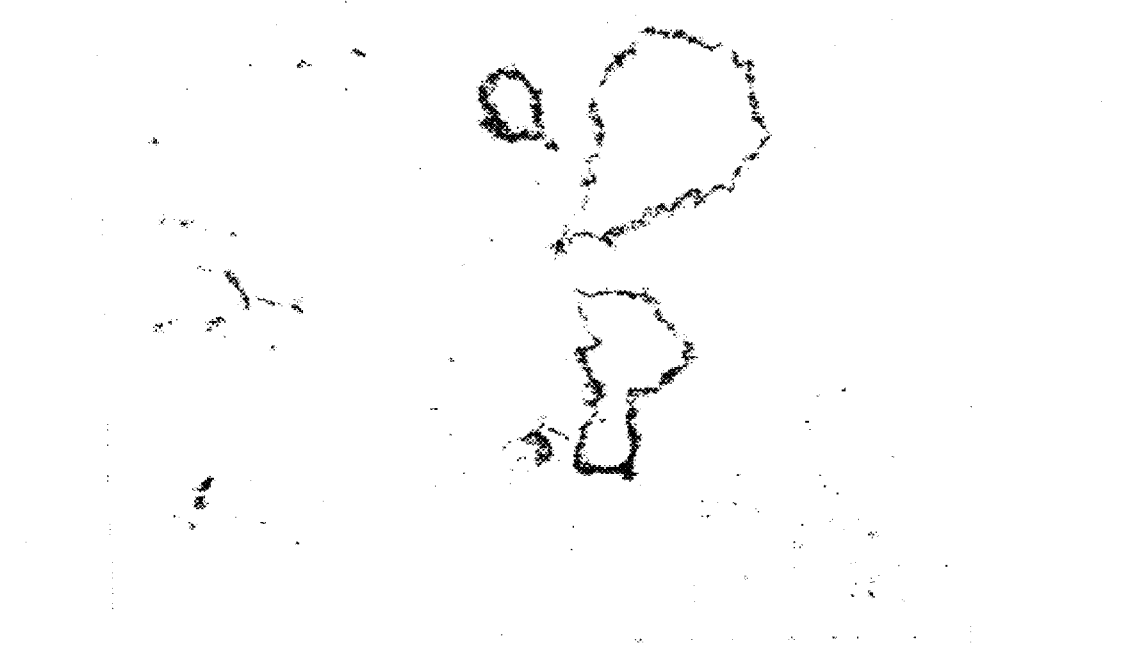
Figure 1B:
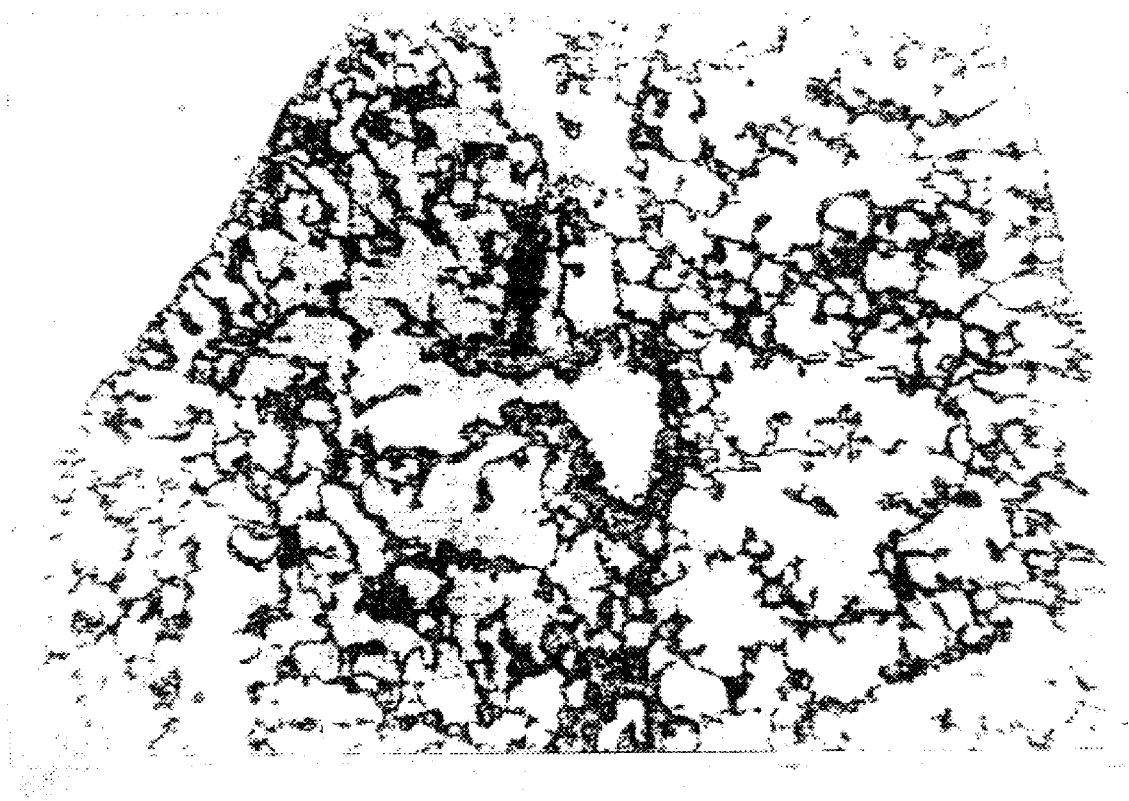

In accordance with the subject invention, nucleic acid constructs together with methods of preparation and use are provided which allow for in vivo modulation of phenotype and/or genotype of cells in the respiratory tract of a mammalian host following delivery of a sufficient dose of a lipid carrier-nucleic acid aerosol to the host mammal or systemic delivery of a sufficient dose of nucleic acid, either naked or complexed with a lipid carrier. The nucleic acid is a nucleotide sequence which codes for a molecule having the biological activity of wild-type CFTR or it is a sequence which when transcribed provides an mRNA sequence complementary to the normal transcription product of an amount and/or of a size sufficient to block express of an endogenous CFTR gene, particularly a mutant CFTR gene. Of particular interest is expression of wild-type CFTR in lung airway cells as well as extrapulmonary cells which are dysfunctional in CF patients. Accordingly, the term "nucleic acid" as used herein refers to either the sense or the antisense strand coding for a molecule having CFTR activity. The lipid carrier-nucleic acid aerosol is obtained by nebulization of a lipid carrier-nucleic acid sample mixture prepared in a biologically compatible fluid that minimizes aggregation of the lipid carrier-nucleic acid complexes. The methods and compositions can be used to produce a mammal comprising an exogenously supplied nucleic acid coding for a molecule having CFTR activity in lung tissue, particularly airway passage cells, as well as submucosal cells, and appropriate exocrine cell types in non-pulmonary tissues.

Central to the present invention is the discovery that lung cells can be transfected via aerosol administration or systemic administration. The instant invention takes advantage of the use of lipid carriers as a delivery mechanism, although high doses of naked nucleic acid can also be used. Lipid carriers are able to stably bind nucleic acid through charge interactions so that resulting complexes may be nebulized and delivered to specific pulmonary tissues may be injected or using a nebulization device. Lipid carriers include but are not limited to liposomes and micelles, as well as biodegradable cationic compounds comprising modified phosphoglycerides, particularly alkylphosphaglycerides.

Lipid carriers, particularly liposomes, have been used effectively to introduce drugs, radiotherapeutic agents, enzymes, viruses, transcription factors and other cellular effectors into a variety of cultured cell lines and animals. In addition, successful clinical trials examining the effectiveness of liposome-mediated delivery of small drug molecules and peptides which act extracellularly have been reported. However, while the basic methodology for using liposome-mediated vectors is well developed and has been shown to be safe, the technique previously has not been developed for delivery of nucleic acid to pulmonary tissue and appropriate extra-pulmonary tissues for in vivo gene therapy of genetic disorders related to mutant CFTR genes. By in vivo gene therapy is meant transcription and/or translation of exogenously supplied nucleic acid to prevent, palliate and/or cure a disease or diseases related to mutant or absent CFTR genes and gene products.

Several factors have been identified that can affect the relative ability of lipid carrier-nucleic acid constructs to provide transfection of lung cells following aerosolized or systemic delivery of lipid carrier-nucleic acid constructs and to achieve a high level of expression. For aerosolized delivery, these factors include (1) preparation of a solution that prior to or during nebulization will not form macroaggregates and wherein the nucleic acid is not sheared into fragments and (2) preparation of both lipid carriers and expression constructs that provide for predictable transformation of host lung cells following aerosolization of the lipid carrier-nucleic acid complex and administration to the host animal. Other factors include the diluent used to prepare the solution and for either aerosolized or systemic delivery the lipidic vector:nucleic acid ratio solution for nebulization.

Aerosol delivery of nucleic acid-lipid carrier complexes provides a number of advantages over other modes of administration. For example, aerosol administration can serve to reduce host toxicity. Such an effect has been observed with the delivery of substances such as pentamidine and cytokines, which can be highly toxic when delivered systematically, but are well tolerated when aerosolized. See, for example, Debs et al., *Antimicrob. Agents Chemother.* (1987) 31:37–41; Debs et al., *Amer. Rev. Respir. Dis.* (1987) 135:731–737; Debs et al., *J. Immunol.* (1988) 140:3482–3488; Montgomery et al., *Lancet* (1987) 11:480–483; Montgomery et al., *Chest* (1989) 95:747–751;

Leoung et al., *N. Eng. J. Med.* (1990) 323:769–775. Additionally, rapid clearance of circulating lipid carriers by the liver and spleen reticuloendothelial system is avoided, thereby allowing the sustained presence of the administered substance at the site of interest, the lung. Serum induced inactivation of the therapeutic agent is also reduced. This method of transfecting lung cells also avoids exposure of the host mammal's gonads, thus avoiding transfection of germ line cells.

Other advantages of the subject invention include ease of administration i.e., the host mammal simply inhales the aerosolized lipid carrier-nucleic acid solution into the intended tissue, the lung. Further, by varying the size of the nebulized particles some control may also be exercised over where in the lung the aerosol is delivered. Delivery may be extended over a long time period. Thus, there is a significant increase in the time period that target cells are exposed to the nucleic acid constructs. Distribution of the aerosol is even throughout areas of the lung accessible to the spray. These advantages are significant, particularly when compared to other routes of administration such as intratracheal delivery which is invasive, the nucleic acid expression constructs are delivered in a bolus, which may disrupt the mucous barrier and additionally may result in pooling of the introduced fluid in areas of the lung at lower elevation. Damage from insertion of the intratracheal tube may alter the ability of cells coming into contact with the nucleic acid constructs to be transfected.

The type of vector used in the subject application also is an advantage over other available systems. For example, most gene therapy strategies have relied on transgene insertion into retroviral or DNA virus vectors. Potential disadvantages of retrovirus vectors, as compared to the use of lipid carriers, include the limited ability of retroviruses mediate in vivo (as opposed to ex vivo) transgene expression; the inability of retrovirus vectors to transfect non-dividing cells; possible recombination events in replication-defect of retrovirus vectors, resulting an infectious retroviruses; possible activation of oncogenes or inhibition of tumor suppressor genes due to the random insertion of the transgene into host cell genomic DNA; size limitations (less than 15 kb of DNA can be packaged in a retrovirus vector, whereas lipid carriers can be used to deliver sequences of DNA of ≧250 kb to mammalian cells) and potential immunogenicity of the traditional vector leading to a host immune response against the vector. In addition, all ex vivo approaches require that the cells removed from the body be maintained in culture for a period of time. While in culture, cells may undergo deleterious or potentially dangerous phenotypic and/or genotypic changes. Adenovirus and other DNA viral vectors share several of the above potential limitations. Particularly for human use, but also for repeated veterinary use, biodegradable lipid carriers, which are noninfectious, nonimmunogenic, and nonmutogenic may be used which are either metabolized or excreted by the host mammal to naturally occurring compounds that are non-toxic to the host and/or are readily excreted.

The constructs for use in the invention include several forms, depending upon the intended use of the construct. Thus, the constructs include vector, transcriptioned cassettes, expression cassettes and plasmids. The transcriptional and translational initiation region (also sometimes referred to as a "promoter,"), preferably comprises a transcriptional initiation regulatory region and a translational initiation regulatory region of untranslated 5' sequences, "ribosome binding sites," responsible for binding mRNA to ribosomes and translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable " is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

The nucleic acid constructs generally will be provided as transcriptional cassettes. An intron optionally may be included in the construct, preferably ≧100 bp and placed 5' to the coding sequence. Generally it is preferred that the construct not become integrated into the host cell genome and the construct is introduced into the host as part of a non-integrating expression cassette. A coding sequence is "operably linked to" or "under the control of " transcriptional regulatory regions in a cell when DNA polymerase will bind the promoter sequence and transcribe the coding sequence into mRNA, either a sense strand or an antisense strand. Thus, the nucleic acid sequence includes DNA sequences which encode polypeptides have the biological activity of CFTR which are directly or indirectly responsible for a therapeutic effect, as well as nucleotide sequences coding for nucleotide sequences such as antisense sequences and ribozymes.

In some cases, it may be desirable to use constructs that produce long-term effects in vivo, either by integration into host cell genomic DNA at high levels or by persistence of the transcription cassette in the nucleus of cells in vivo in stable, episomal form. Integration of the transcription cassette into genomic DNA of host cells in vivo may be facilitated by administering the transgene in a linearized form (either in the coding region alone, or the coding region together with 5' and 3' regulatory sequences, but without any plasmid sequences present). Additionally, in some instances, it may be desirable to delete or inactivate a mutant CFTR gene and replace it with a coding sequence for a biologically functional CFTR molecule.

The constructs for use in the invention include several forms, depending upon the intended use of the construct. Thus, the constructs include vectors, transcriptional cassettes, expression cassettes and plasmids. The transcriptional and translational initiation region (also sometimes referred to as a "promoter, "), preferably comprise a transcriptional initiation regulatory region and a translational initiation regulatory region of untranslated 5' sequences, "ribosome binding sites," responsible for binding mRNA to ribosomes and translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

For the transcriptional initiation region, or promoter element, any region may be used with the proviso that it provides the desired level of transcription of the DNA sequence of interest. The transcriptional initiation region may be native to or homologous to the host cell, and/or to the DNA sequence to be transcribed, or foreign or heterologous to the host cell and/or the DNA sequence to be transcribed. By foreign to the host cell is intended that the transcriptional initiation region is not found in the host into which the construct comprising the transcriptional initiation region is to be inserted. By foreign to the DNA sequence is intended a transcriptional initiation region that is not normally associated with the DNA sequence of interest. Efficient promoter elements for transcription initiation include the SV40 (simian virus 40) early promoter, the RSV (Rous sarcoma virus) promoter, the Adenovirus major late promoter, and the human CMV (cytomegalovirus) immediate early 1 promoter.

Inducible promoters also find use with the subject invention where it is desired to control the timing of transcription. Examples of promoters include those obtained from a β-interferon gene, a heat shock gene, a metallothionein gene or those obtained from steroid hormone-responsive genes, including insect genes such as that encoding the ecdysone receptor. Such inducible promoters can be used to regulate transcription of the transgene by the use of external stimuli such as interferon or glucocorticoids. Since the arrangement of eukaryotic promoter elements is highly flexible, combinations of constitutive and inducible elements also can be used. Tandem arrays of two or more inducible promoter elements may increase the level of induction above baseline levels of transcription which can be achieved when compared to the level of induction above baseline which can be achieved with a single inducible element.

Generally, the regulatory sequence comprises DNA up to about 1.5 Kb 5' of the transcriptional start of a gene, but can be significantly smaller. This regulatory sequence may be modified at the position corresponding to the first codon of the desired protein by site-directed mutagenesis (Kunkel TA, 1985, *Proc. Natl. Acad. Sci. (USA)*, 82:488–492) or by introduction of a convenient linker oligonucleotide by ligation, if a suitable restriction site is found near the N-terminal codon. In the ideal embodiment, a coding sequence with a compatible restriction site may be ligated at the position corresponding to codon #1 of the gene. This substitution may be inserted in such a way that it completely replaces the native coding sequence and thus the substituted sequence is flanked at its 3' end by the gene terminator and polyadenylation signal.

Transcriptional enhancer elements optionally may be included in the expression cassette. By transcriptional enhancer elements is intended DNA sequences which are primary regulators of transcriptional activity and which can act to increase transcription from a promoter element, and generally do not have to be in the 5' orientation with respect to the promoter in order to enhance transcriptional activity. The combination of promoter and enhancer element(s) used in a particular expression cassette can be selected by one skilled in the art to maximize specific effects. Different enhancer elements can be used to produce a desired level of transgene expression in a wide variety of tissue and cell types. For example, the human CMV immediate early promoter-enhancer element can be used to produce high level transgene expression in many different tissues in vivo.

Examples of other enhancer elements which confer a high level of transcription on linked genes in a number of different cell types from many species include enhancers from SV40 and RSV-LTR. The SV40 and RSV-LTR are essentially constitutive. They may be combined with other enhancers which have specific effects, or the specific enhancers may be used alone. Thus, where specific control of transcription is desired, efficient enhancer elements that are active only in a tissue-, developmental-, or cell-specific fashion include immunoglobulin, interleukin-2 (IL-2) and β-globin enhancers are of interest. Tissue-, developmental-, or cell-specific enhancers can be used to obtain transgene expression in particular cell types, such as B-lymphocytes and T-lymphocytes, as well as myeloid, or erythroid progenitor cells. Alternatively, a tissue-specific promoter such as that derived from the human cystic fibrosis transmembrane conductance regulator (CFTR) gene can be fused to a very active, heterologous enhancer element, such as the SV40 enhancer, in order to confer both a high level of transcription and tissue-specific transgene transcription. In addition, the use of tissue-specific promoters, such as LCK, may allow targeting of transgene transcription to T lymphocytes. Tissue specific transcription of the transgene may be important, particularly in cases where the results of transcription of the transgene in tissues other than the target tissue would be deleterious.

Tandem repeats of two or more enhancer elements or combinations of enhancer elements may significantly increase transgene expression when compared to the use of a single copy of an enhancer element; hence enhancer elements find use in the expression cassette. The use of two different enhancer elements from the same or different sources flanking or within a single promoter can in some cases produce transgene expression in each tissue in which each individual enhancer acting alone would have an effect, thereby increasing the number of tissues in which transcription is obtained. In other cases, the presence of two different enhancer elements results in silencing of the enhancer effects. Evaluation of particular combinations of enhancer elements for a particular desired effect or tissue of expression is within the level of skill in the art.

Although generally it is not necessary to include an intron in the expression cassette, an intron comprising a 5' spice site (donor site) and a 3' spice site (acceptor site) separated by a sufficient intervening sequence to produce high level, extended in vivo expression of a transgene administered iv or ip can optionally be included. Generally, an intervening sequence of about 100 bp produces the desired expression pattern and/or level, but the size of the sequence can be varied as need to achieve a desired result. The optional intron placed 5' to the coding sequence results in high level extended in vivo expression of a transgene administered iv or ip but generally is not necessary to obtain expression. Optimally, the 5' intron specifically lacks cryptic splice sites which result in aberrantly spliced mRNA sequences. If used, the intron splice donor and splice acceptor sites, arranged from 5' to 3' respectively, are placed between the transcription initiation site and the translational start codon as diagrammed in (1), below.

Consensus sequences SEQ ID NO:4 for the 5' and 3' splice sites used in RNA splicing (1)

```
5' exon                    intron                              3' exon¹
      C        A         U U U U U U U U U U    C              G
5'---or A G ▓ or A G U---- ----or or or or or or or or or or N or ▓  or---3'
      A        G         C C C C C C C C C C    U              A consensus sequence for              consensus sequence for 3' splice site
5' splice site ("donor site")       ("acceptor site")
```

¹The sequence given is that for the RNA chain; the nearly invariant GU and AG dinucleotides at either end of the intron are shaded.

Alternatively, the intervening sequence may be placed 3' to the translational stop codon and the transcriptional terminator or inside the coding region. The intron can be a hybrid intron with an intervening sequence or an intron taken from a genomic coding sequence. An intron 3' to the coding region, a 5' intron which is of less than 100 bp, or an intron which contains cryptic splice sites may under certain condition substantially reduce the level of transgene expression produced in vivo. However, unexpectedly, a high level of in vivo expression of a transgene can be achieved using a vector that lacks an intron. Such vectors therefore are of particular interest for in vivo transfection.

Downstream from and under control of the transcriptional initiation regulatory regions is a multiple cloning site for insertion of a nucleic acid sequence of interest which will provide for one or more alterations of host genotype and modulation of host phenotype. Conveniently, the multiple cloning site may be employed for a variety of nucleic acid sequences in an efficient manner. The nucleic acid sequence inserted in the cloning site may have any open reading frame encoding a polypeptide of interest, for example, an enzyme, with the proviso that where the coding sequence encodes a polypeptide of interest, it should lack cryptic splice sites which can block production of appropriate mRNA molecules and/or produce aberrantly spliced or abnormal mRNA molecule. The nucleic acid sequence may be DNA; it also may be a sequence complementary to a genomic sequence, where the genomic sequence may be one or more of an open reading frame, an intron, a non-coding leader sequence, or any other sequence where the complementary sequence will inhibit transcription, messenger RNA processing, for example splicing, or translation.

The incidence of integration of the transcription cassette into genomic DNA may be increased by incorporating a purified retroviral enzyme, such as the HIV-1 integrase enzyme, into the lipid carrier-DNA complex. Appropriate flanking sequences are placed at the 5' and 3' ends of the nucleic acid. These flanking sequences have been shown to mediate integration of the HIV-1 DNA into host cell genomic DNA in the presence of HIV-1 integrase. Alternatively, the duration of the expression of the exogenous nucleic acid in vivo can be prolonged by the use of constructs that contain non-transforming sequences of a virus such as Epstein-Barr virus, and sequences such as oriP and EBNA-1 which appear to be sufficient to allow heterologous DNA to be replicated as an episome in mammalian cells (Buhans et al., Cell (1986) 52:955).

The termination region which is employed primarily will be one of convenience, since termination regions appear to be relatively interchangeable. The termination region may be native to the intended nucleic acid sequence of interest, or may be derived from another source. Convenient termination regions are available and include the 3' end of a gene terminator and polyadenylation signal from the same gene from which the 5' regulatory region is obtained. Adenylation residues, preferably more than 32 and up to 200 or more as necessary may be included in order to stabilize the mRNA. Alternatively, a terminator and polyadenylation signal from different gene/genes may be employed with similar results. Specific sequences which regulate post-transcriptional mRNA stability may optionally be included. For example, certain polyA sequences (Volloch et al. Cell (1981) 23:509) and β-globin mRNA elements can increase mRNA stability, whereas certain AU-rich sequences in mRNA can decrease mRNA stability (Shyu et al., Genes and Devel. (1989) 3:60). In addition, AU regions in 3' non-coding regions may be used to destabilize mRNA if a short half-life mRNA is desirable for the gene of interest.

Isolation of Genes and Construction of Vectors

Nucleic acid sequences for use in the preset invention, can be derived from known sources, for example by isolating the nucleic acid from cells containing the desired gene, using standard techniques. Similarly, the gene sequence can be generated synthetically, using standard modes of polynucleotide synthesis, well known in the art. See, e.g. Edge, M. D., Nature (1981) 292:756; Nambair, et al., Science (1984) 223:1299; Jay, Ernest, J Biol Chem (1984) 259:6311. Generally, synthetic oligonucleotides are prepared by either the phosphotriester method as described by Edge et al., Nature (supra) and Duckworth et al., Nucleic Acids Res (1981)9:1691, or the phosphoramidite method as described by Beaucage, S. L., and Caruthers, M. H., Tet. Letts. (1981) 22:1859, and Matteucci, M. D., and Caruthers, M. H.,J. Am. Chem. Soc. (1981) 103:3185, and can be prepared using commercially available automated oligonucleotide synthesizers. The gene sequence can be designed with the appropriate codons for the particular amino acid sequence. In general, one will select preferred codons for expression in the intended host. The complete sequence is assembled from overlapping oligonucleotides prepared by standard methods and assembled into a complete coding sequence. See, e.g., Edge (1981) Nature 292:756; Nambair et al., (1984) Science 223:1299; Jay et al., (1984) J. Biol. Chem. 259:6311. Partial CFTR cDNA clones T11 T16-1 T16-4.5 and C1-⅕ (Riordan et al., Science (1989) 245:1066–1073) are available from the American Type Culture Collection (Rockland, Md.). Full length isolated DNAs encoding CFTR protein and a variety of mutants thereof are disclosed in EP Application 91301819.8. See also, Goodfellow, P., Nature (1989) 341:102–103; Rommens, et al., Science (1989) 245:1059–1054; Beardsley, et al., Sci. Am. (1989) 261:28–30. It may be desirable to produce mutants or analogs of the proteins of interest. Mutants or analogs may be prepared by the deletion of a portion of the sequence encoding the protein, by insertion of a sequence, and/or by substitution of one or more nucleotides within the sequence. The mutation can be one that affects secretion of a normally secreted protein, so as to eliminate or decrease systemic side effects of the protein. Techniques for modifying nucleotide sequences, such as site-directed mutagenesis, are well known to those skilled in the art. See, e.g., Sambrook et al., infra; DNA *Cloning*, Vols. I and II, supra; *Nucleic Acid Hybridization*, infra.

A particularly convenient method for obtaining nucleic acid for use in the lipid carrier-nucleic acid preparations, is by recombinant means. Thus, the CFTR gene can be excised from a plasmid carrying the desired gene, using restriction enzymes and procedures. Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. If desired, size separation of the cleaved fragments may be performed by polyacrylamide gel or agarose gel electrophoresis using standard techniques. A general description of size separations is found in *Methods in Enzymology* (1950) 65:499–560.

Restriction cleaved fragments may be blunt ended by treating with the large fragment of *E. coli* DNA polymerase I (Klenow) in the presence of the four deoxynucleotide triphosphates (dNTPs) using standard techniques. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture can be extracted with e.g. phenol/chloroform, and ethanol precipitated. Treatment under appropriate conditions with S1 nuclease or BAL-31 results in hydrolysis of any single-stranded portion.

Once coding sequences for the desired proteins have been prepared or isolated, they can be cloned into any suitable vector or replicon. Numerous cloning vectors are known to those of skill in the art; the selection of an appropriate cloning vector is known to those of skill in the art, and the selection of an appropriate cloning vector is a matter of choice. Ligation to other sequences is performed using standard procedures, known in the art. For example, ligations can be accomplished in 20 mM Tris-Cl pH 7.5, 10 mM MgCl$_2$, 10 mM DTT, 33 μg/ml BSA, 10 mM-50 mM NaCl, and either 40 uM ATP, 0.01–0.02 (Weiss) units T4 DNA ligase at 0° C. (for "sticky end"ligation) or 1 mM ATP, 0.3–0.6 (Weiss) units T4 DNA ligase at 14° C. (for "blunt ends" ligation). Intermolecular "sticky end" ligations are usually performed at 30–100 μg/ml total DNA concentration (5–100 nM total end concentration).

The nucleic sequence is placed under the control of a promoter, ribosome binding site and, optionally, an operator (collectively referred to herein as "control" elements), so that the coding sequence is transcribed into RNA in the host tissue transformed by the lipid carrier-nucleic acid. The coding sequence may or may not contain a signal peptide or leader sequence. A "promoter sequence" is a DNA regulatory region capable of binding RNA polymerase in a cell and initiating transcription of a downstream (3' direction) coding sequence. For purpose of defining the present invention, the promoter sequence is bound at the 3' terminus by the transcription start codon (ATG) of a coding sequence and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase. Nucleic acid "control sequences" or "regulatory regions" refer collectively to promoter sequences, ribosome binding sites, polyadenylation signals, transcription termination sequences, upstream regulatory domains, enhances, and the like, which collectively provide for the transcription and translation of a coding sequence in a host cell.

The choice of regulatory elements will depend on the host cell which is to be transformed and the type of nucleic acid preparation used. Thus, if the host cells' endogenous transcription and translation machinery will be used to express a CFTR molecule, control elements functional in the particular host and which provide for expression are used. Several promoters for use in mammalian cells are known in the art and include, but are not limited to, a SV40 (Simian Virus 40) early promoter, a RSV (Rous Sarcoma Virus) promoter, an Adenovirus major late promoter, and a human CMV (Cytomegalovirus) immediate early one promoter. Other promoters which may be used include those derived from mouse mammary tumor virus (MMTV, T7, T3, and the like). Particularly useful in the present invention are the RSV promoter and the CMV promoter, particularly the immediate early promoter from the AD169 strain of CMV SEQ ID NO: 2. In addition to the above sequences, it may be desirable to add to the nucleic acid construct regulatory sequences which allow for regulation of the expression of the CFTR molecule. Regulatory sequences are known to those of skill in the art, and examples include those which cause the expression of a gene to be turned on or off in response to a chemical or physical stimulus, including the presence of a regulatory compound. Such promoters can be used to regulate expression of the transgene by the use of external stimuli such as interferon or glucocorticoids.

Other types of regulatory elements may also be present in the plasmid, for example, enhancer sequences. Such regulatory elements include those obtainable from β-interferon, heat shock, metallothionein or steroid hormone responsive genes, including insect genes such as the ecdysone receptor gene. Since the arrangement of eukaryotic promoter elements is highly flexible, combinations of constitutive and inducible elements can be used. Tandem arrays of two or more inducible promoter elements may increase the level of induction above baseline levels of transcription which can be achieved with a single inducible element. By transcription enhancer elements are intended DNA sequences which are primary regulators of transcriptional activity which can act to increase transcription from a promoter element, and generally do not have to be in the 5' orientation with respect to the promoter in order to enhance transcriptional activity.

The combination of promoter and enhancer elements used in a particular nucleic acid construct can be selected by one skilled in the art to maximize specific effects; different enhancer elements can be used to produce a desired level of transcription. For example, a tissue specific promoter such as that derived from the human cystic fibrosis transmembrane conductance regulator (CFTR) gene can be used flanking a very active, heterologous enhancer element, such as the SV40 enhancer, in order to obtain both a high level of expression and expression of the nucleic acid primarily in lung. Tandem repeats of two or more enhancer elements or combinations of enhancer elements may significantly increase transcription when compared to the use of a single copy of an enhancer element. The use of two different enhancer elements from the same or different sources, flanking or within a single promoter may be used. Evaluation of particular combinations of enhancer elements for a particular desired effect or expression level is within the knowledge of one skilled in the art. Promoter-enhancer elements which are least partially derived from CMV Townes and/or AD169 strains are of particular interest for providing a high level of expression of exogenous nucleic acid.

The termination region which is employed primarily will be one of convenience, since termination regions appear to be relatively interchangeable. The termination region may be native to the CFTR gene, or may be derived from another source. Convenient termination regions are available and include the 3' end of a gene terminator and polyadenylation signal from the same gene from which the 5' regulatory region is obtained. Adenylation residues, preferably more than 32 kb and up to 200 kb or more if necessary may be included in order to stabilize the mRNA. Alternatively, terminator and polyadenylation signals from a gene/genes other than the CFTR gene may be employed with similar results. Specific sequences which regulate post-transcriptional mRNA stability may optionally be included. For example, certain polyA sequences (Volloch et al., Cell (1981) 23:509) and β-globin mRNA elements can increase mRNA stability, whereas certain AU-rich sequences in mRNA can decease mRNA stability (Shyu et al., Genes and Development (1989) 3:60). In addition, AU regions in 3' non-coding regions may be used to destabilize mRNA if a short half life mRNA is desirable. A 3'-intron should be avoided, particularly a SV40 3'-intron. If used, the 3'-intron should be greater than about 70 bp.

The nucleic acid construct may include sequences for selection, such as a neomycin resistance gene, dihydrofolate reductase gene, and/or signal sequences to generate recombinant proteins that are targeted to different cellular compartment, more particularly to provide for secretion of the nucleic acid expression product. Any of a variety of signal sequences may be used which are well known to those skilled in the art, for example, a basic sequence of amino acids may be encoded which results in nucleic localization ? of the protein.

A transcription vector is constructed so that the particular coding sequence is located in the vector with the appropriate regulatory sequences, the positioning and orientation of the coding sequence with respect to the control sequences being such that the coding sequence is transcribed under the "control" of the control sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

Preparation of Lipid carriers

Lipid carriers for use in the instant invention include cationic (positively charged), anionic (negatively charged) and neutral preparations. However, cationic lipid carriers are particularly preferred because a tight charge complex can be formed between the cationic lipid carrier and the polyanionic nucleic acid. For example, this results in a lipid carrier-nucleic acid complex which will withstand both the forces of nebulization and the environment within the lung airways and be capable of transfecting lung cells after the aerosolized DNA:lipid carrier complex has been deposited in the lung. Cationic lipid carriers have been shown to mediate intracellular delivery of plasmid DNA (Felgner, et al., *Proc. Natl. Acad. Sci.* U.S.A. (1987) 84:7413–7416); mRNA (Malone, et al., *Proc. Natl. Acad. Sci.* U.S.A. (1989) 86:6077–6081); and purified transcription factors (Debs, et al., *J. Biol. Chem.* (1990) 265:10189–10192), in functional form.

Particular cells within the lung and extrapulmonary organs may be targeted by modifying the lipid carriers to direct them to particular types of cells using site-directing molecules. Thus antibodies or ligands for particular receptors may be employed, to target a cell associated with a particular surface protein. A particular ligand or antibody may be conjugated to the lipid carrier in accordance with conventional ways, either by conjugating the site directing molecule to a lipid for incorporation into the lipid bilayer or by providing for a linking group on a lipid present in the bilayer for linking to a functionality of the site-directing compound. Such techniques are well know to those skilled in the art. Precise intrapulmonary targeting also may be achieved by a) altering aerosol particle size to preferentially direct the aerosol to alveoli or proximal versus distal airways or (b) to covalently couple monoclonal antibodies to the lipid carrier surface, thereby targeting lung cells expressing the corresponding cell surface antigen.

The various lipid carrier-nucleic acid complexes wherein the lipid carrier is a liposome are prepared using methods well known in the art. See, e.g., Straubinger et al., in *Methods of Immunology* (1983), Vol. 101, pp. 512–527. By "lipid carrier-nucleic acid complex" is meant a nucleic acid sequence as described above, generally bound to the surface of a lipid carrier preparation, as discussed below. The lipid carrier preparation can also contain other substances, such as enzymes necessary for integration, transcription and translation, cofactors, etc. Furthermore, the lipid carrier-nucleic acid complex can include targeting agents to deliver the complex to particular cell or tissue types. Where it is desired to entrap the nucleic acid, MLVs containing nucleic acid can be prepared by depositing a thin firm of phospholipid on the walls of a glass tube and subsequently hydrating with a solution of the material to be encapsulated and vortexing.

The nucleic acid material is added to a suspension of preformed MLVs or SLVs only after the lipid carriers have been prepared and then vortexed. When using lipid carriers containing cationic lipids, the dried lipid film is suspended in an appropriate mixing solution such as sterile water or an isotonic buffer solution such as 10 mM Tris/NaCl, or 5% dextrose in sterile water, sonicated, and then the preformed lipid carriers are mixed directly with the DNA. The lipid carrier and DNA form a very stable complex due to binding of the negatively charged DNA to the cationic lipid carriers. SUVs find use with small nucleic acid fragments as well as large regions of DNA (≧250 kb).

In preparing the lipid carrier-nucleic acid complex, care should be taken to exclude any compounds from the mixing solution which may promote the formation of aggregates of the lipid carrier-nucleic acid complexes. For school administration, large particles generally will not be aerosolized by the nebulizer and even if aerosolized would be too large to penetrate beyond the large airways. Aggregation of the lipid carrier-nucleic acid complex is prevented by controlling the ratio of DNA to lipid carrier, minimizing the overall concentration of DNA:lipid carrier complex in solution, usually less than 5 mg DNA/8 ml solution, and the avoiding chelating agents as EDTA, and significant amounts of salt which tend to promote macroaggregation. The preferred excipient is water, dextrose/water or another solution having low or no ionic strength. Further, the volume must be adjusted to the minimum for deposition in the lung of the host mammal, but taking care not to make the solution too concentrated so that aggregates form.

The choice of lipid carriers and the concentration of lipid carrier-nucleic acid complexes thus involves a two step process. The first step is to identify lipid carriers and concentration of lipid carrier-nucleic acid complexes that do not aggregate when the components are combined or during the significant agitation of the mixture that occurs during the nebulization step. The second step is to identify among those that are identified as of interest at the first step (i.e. do not aggregate) those complexes that provide for a high level of transfection and expression of a gene of interest in target cells in the lung. The level of expression and the cell type in which expression of the recombinant gene is obtained may be determined at the mRNA level and/or at the level of polypeptide or protein. Gene product may be quantitated by measuring its biological activity in tissues. For example, enzymatic activity can be measured by biological assay or by identifying the gene product in transfected cells by immunostaining techniques such as probing with an antibody which specifically recognizes the gene product or a reported gene product present in the expression cassette.

As an example, a reporter gene CAT (which encodes chloramphenicol acetyl transferase) can be inserted in the expression cassette and used to evaluate each lipid carrier composition of interest. The DNA:lipid carrier complexes must be mixed in solutions which do not themselves induce aggregation of the DNA:lipid carrier complexes such as sterile water. The expression cassette (DNA) is mixed together with the lipid carriers to be tested in multiple different ratios, ranging as an example from 4:1 to 1:10 (micrograms DNA to nanomoles cationic lipid). The results provide information concerning which ratios result in aggregation of the DNA:lipid carrier complexes and are therefore not useful for use in vivo, and which complexes remain in a form suitable for aerosolization. The ratios which do not result in aggregation are tested in animal models to determine which of the DNA:lipid carrier ratios confer the highest level of transgene expression in vivo. For example, the optimal DNA:lipid carrier ratios for SUV for DOTMA/DOPE DDAB:Chol, are 1:1 or 1:2 and ethylphosphatidylcholine (E-PC and ethyl-dimyristylphosphatidylcholine (E-DMPC).

Aerosol Administration

The mammalian host may be any mammal having symptoms of a genetically-based disorder. Thus, the subject application finds use in domestic animals, feed stock, such as bovine, ovine, and porcine, as well as primates, particularly humans. In the method of the invention, transformation in vivo is obtained by introducing a non-integrating therapeutic plasmid into the mammalian host complexed to a lipid carrier, particularly a cationic lipid carrier more particularly, for human use or for repeated applications a biodegradable lipid carrier. For introduction into the mammalian host any physiologically acceptable medium may be employed for administering the DNA or lipid carriers, such as deionized water, 5% dextrose in water, and the like. Other components may be included in the formulation such as stabilizers, biocides, etc, providing that they meet the criteria outlined above, i.e. do not cause aggregation of the complexes. The various components listed above find extensive exemplification in the literature and need not be described in particular here.

For aerosol delivery in humans or other primates, the aerosol is generated by a medical nebulizer system which delivers the aerosol through a mouthpiece, facemask, etc. from which the mammalian host can draw the aerosol into the lungs. Various nebulizers are known in the art and can be used in the method of the present invention. See, for example, Boiarski, et al., U.S. Pat. No. 4,268,460; Lehmbeck, et al., U.S. Pat. No. 4,253,468; U.S. Pat. No. 4,046,146; Havstad, et al., U.S. Pat. No. 3,826,255; Knight, et al., U.S. Pat. No. 4,649,911; Bordoni, et al., U.S. Pat. No. 4,510,829. The selection of a nebulizer system depends on whether alveolar or airway delivery (i.e., trachea, primary, secondary or tertiary bronchi, etc.), is desired.

A convenient way to insure effective delivery of the nucleic acid to the alveoli is to select a nebulizer which produces sufficiently small part for example, particles with a mean particle diameter of less than 5.0 microns ($\mu$m). More preferably the particles have a mean particle diameter of about 0.2 to about 4.0 $\mu$m, and most preferably the particles have mean diameter of about 0.2 to about 2 $\mu$m, since larger particles ($\geq$5 $\mu$m) are generally deposited in the proximal airways or nasopharynx. As an alternative to selecting small mean particle diameters to achieve substantial alveoli deposition, a very high dosage of the lipid carrier-nucleic acid preparation can be administered, with a larger mean particle diameter. A proviso to such an approach is that the particular lipid carrier-nucleic acid complex is chosen that is not too irritating at the required dosage and that there be a sufficient number of particles in the total particle population having a diameter in the 0.5 to about 5 $\mu$m range to allow for deposition in the alveoli. For proximal airway delivery, the mean particle size will be larger. For example, suitable mean particle diameter will generally be less than about 15 $\mu$m, more preferably from about 4 $\mu$m, and most preferably from about 5 $\mu$m to about 10 $\mu$m.

Examples of nebulizers useful for alveolar delivery include the Acorn 1 nebulizer, and the Respirgard II® Nebulizer System, both available commercially from Marquest Medical Products, Inc., Inglewood, Colo. Other commercially available nebulizers for use with the instant invention include the Ultra Vent® nebulizer available from Mallinckrodt, Inc. (Maryland Heights, Mo.); the Wright nebulizer (Wright, B. M., *Lancet* (1958) 3:24–25); and the DeVilbiss nebulizer (Mercer et al., *Am. Ind. Hyg. Assoc. J.* (1968) 29:66–78; T. T. Mercer, *Chest* (1981) 80:6 (Sup) 813–817). Nebulizers useful for airway delivery include those typically used in the treatment of asthma. Such nebulizers are also commercially available. One of skill in the art can determine the usefulness of a particular nebulizer by measuring the mean particle size generated thereby with for example, a 7 stage Mercer cascade impactor (Intox Products, Albuquerque, N.M.ex.). Concentrations of the lipid carrier-nucleic acid complex from the impactor plates can be determined by eluting the complex therefrom and assessing the optical density at an appropriate wavelength and comparing the standard curves. Results are generally expressed as mass median aerodynamic diameter±geometric standard deviation (Raabe, *J. Aerosol Sci.* (1971) 2:289–303).

The amount of lipid carriers used will be an amount sufficient to provide for adequate transfection of cells after entry of the DNA or complexes into the lung and to provide for a therapeutic level of transcription and/or translation in transfected cells. A therapeutic level of transcription and/or translation is a sufficient amount to prevent, treat, or palliate a disease of the host mammal following administration of the lipid carrier-nucleic acid complex to the host mammal's lung, particularly the alveoli or airway. Thus, an "effective amounts" of the aerosolized lipid carrier-nucleic acid preparation, is a dose sufficient to effect treatment, that is, to cause alleviation or reduction of symptoms, to inhibit the worsening of symptoms, to prevent the onset of symptoms, and the like. The dosages of the preset compositions which constitute an effective amount can be determined in view of this disclosure by one of ordinary skill in the art by running routine trials with appropriate controls. Comparison of the appropriate treatment groups to the controls will indicate whether a particular dosage is effective in preventing or reducing particular symptoms. Appropriate doses are discussed further below. While there is no direct method of measuring the actual amount of lipid carrier-nucleic acid complex delivered to the alveoli, bronchoalveolar lavage (BAL) can be used to indirectly measure alveolar concentrations of any expressed and secreted protein, usually 18–24 hrs after inhalation to allow clearance of the protein deposited in the larger airways and bronchi.

The total amount of nucleic acid delivered to a mammalian host will depend upon many factors, including the total amount aerosolized, the type of nebulizer, the particle size, breathing patterns of the mammalian host, severity of lung disease, concentration and mean diameter of the lipid carrier-nucleic acid complex in the aerosolized solution, and length of inhalation therapy. Thus, the amount of expressed protein measured in the airways may be substantially less than what would be expected to be expressed from the amount of nucleic acid present in the aerosol, since a large portion of the complex may be exhaled by the subject or trapped on the interior surfaces of the nebulizer apparatus. For example, approximately one third of the lipid carrier-nucleic acid dose that is placed into the nebulizer remains in the nebulizer and associated tubing after inhalation is completed. This is true regardless of the dose size, duration of inhalation, and type of nebulizer used. Moreover, resuspension of the residue and readministration does not significantly increase the dose delivered to the subject; about one third remains in the nebulizer. Additionally, efficiency of expression of the encoded protein will vary widely with the expression system used.

Despite the interacting factors described above, one of ordinary skill in the art will be able readily to design effective protocols, particularly if the particle size of the aerosol is optimized. Based on estimates of nebulizer efficiency, an effective dose delivered usually lies in the range of about 1 mg/treatment to about 500 mg/treatment, although more or less may be found to be effective depending on the subject and desired result. It is generally desirable to administer higher doses when treating more severe conditions. Generally, the nucleic acid is not integrated into the host cell genome, thus if necessary, the treatment can be repeated on an ad hoc basis depending upon the results achieved. If the treatment is repeated, the mammalian host is monitored to ensure that there is no adverse immune response to the treatment. The frequency of treatments depends upon a number of factors, such as the amount of lipid carrier-nucleic acid complex administered per dose, as well as the health and history of the subject. As used herein, with reference to dosages, "lipid carrier-nucleic acid aerosol" refers to the amount of lipid carrier-nucleic acid complex that is placed in the nebulizer and subjected to aerosolization. The "amount nebulized" or "amount aerosolized" of the complex means the amount that actually leaves the apparatus as an aerosol, i.e., the amount placed into the apparatus less the amount retained in the reservoir and on the inner surfaces of the apparatus at the conclusion of a treatment session.

To treat pulmonary infections such as bronchitis and pneumonia, it will usually be necessary to administer at least one dose per day over a period of about 4 to about 21 consecutive days or longer. The treatment is usually carried out on consecutive days because new areas of the lungs open up to penetration and deposition of the nucleic acid with increasing resolution of the infection. The success of the treatment can be monitored and the administration regimen altered by assessing conventional clinical criteria; e.g., clearing of radiographic infiltrate, improved arterial $PO_2$ (e.g., >70 mmHg), reduction in dyspnea, respiratory rate and/or fever. For the treatment of genetic disorders, such as cystic fibrosis, the lipid carrier-nucleic acid complex will be administered at regular intervals, from once a week to once every one to several months, in order to replace the normal CFTR protein in critical host airway cells, since these cells continue to turn over. It may also be possible to stably transfect the CFRT gene into appropriate lung stem cells, which would then provide a continuous source of normal airway cells without requiring lifelong treatment. Potential therapeutic effects of the gene product can be measured, by determining the effects of gene expression on survival of transgenic host mammals in which the transgene is expressed. Production of significant amounts of a transgene product will substantially prolong the survival and improve the quality of life of the afflicted host.

Where expression of the polypeptide/protein or even the mRNA itself confers a changed biochemical phenotype upon the host, the presence of a new phenotype or absence of an old phenotype may be evaluated; for example, as a result of transformation of the host cells, there may be enhanced production of pre-existing desirable products formerly produced in insufficient quantities or there may be reduction or even suppression of an undesirable gene product using antisense, ribozyme or co-suppression technologies; in the case of reduction or suppression, a reduction or elimination of the gene product may be determined.

The potential toxicity of the treatment may be evaluated by behavioral manifestations, and where appropriate, by analysis of biopsy specimens. Thus, behavioral activity which evidences distress, such as changes in activity level, changes in eating and drinking patterns and the like, can be monitored, as well as evidence of necrosis, edema or inflammation in biopsy.

The subject compositions can be provided for use in one or more procedures. Kits will usually include the DNA either as naked DNA or complexed to lipid carriers. Additionally, lipid carriers may be provided in a separate container for complexing with the provided DNA. The DNA or the lipid carrier/DNA complexes may be present as concentrates which may be further diluted prior to use or they may be provided at the concentration of use, where the vials may include one at more dosages. Conveniently, single dosages may be provided in sterilized containers suitable for use with a nebulizer, so that the physician or veterinarian may employ the containers directly with a nebulizer, where the containers will have the desired amount and concentration of agents. Thus, the kit may have a plurality of containers containing the DNA or the DNA/lipid carrier complexes in appropriate proportional amounts, and optionally, diluent and mixing solutions. When the containers contain the formulation for direct use, usually there will be no need for other reagents for use with the method.

Systemic administration

The recombinant coding-sequence flanked at its 5' end by the promoter and regulatory sequences and at its 3' end by a terminator and regulatory sequences may be introduced into a suitable cloning plasmid (e.g., pUC18, pSP72) for use in direct DNA uptake in host cells following introduction of the expression plasmid alone into the host. The nucleic acid construct also may be complexed with a carrier such as lipid carriers, particularly cationic lipid carriers. Lipid carriers can be prepared from a variety of cationic lipids, including DOTAP, DOTMA, DDAB, L-PE, and the like. Lipid carriers containing a cationic lipid, such as {N(1-(2,3-dioleyloxy) propyl}-N,N,N-trimethylammonium} chloride (DOTMA) also known as "lipofectin", dimethyl dioctadecyl ammonium bromide (DDAB), 1,2-dioleoyloxy-3-(trimethylammonio) propane (DOTAP) or lysinyl-phosphatidylethanolamine (L-PE) and a second lipid, such as distearoylphosphatidylethanolamine (DOPE) or cholesterol (Chol), are of particular interest. DOTMA synthesis is described in Felgner, et al., Proc. Nat. Acad. Sciences, (U.S.A.) (1987) 84:7413–7417. DOTAP synthesis is described in Stamatatos, et al., *Biochemistry* (1988) 27:3917. DOTMA:DOPE lipid carriers can be purchased from, for example, BRL. DOTAP:DOPE lipid carriers can be purchased from Boehringer Mannheim. Cholesterol and DDAB are commercially available from Sigma Corporation. DOPE is commercially available from Avanti Polar Lipids. DDAB:DOPE can be purchased from Promega. Biodegradable cationic amphiphiles also have been shown to form stable complexes with polyanionic DNA.

Cationic liposomes have been shown to be capable of mediating high level cellular expression of transgenes or mRNA by delivering the nucleic acid into a wide variety of cells in culture. The use of specific cationic lipids can confer specific advantages for in vivo delivery. For example iv injection of DOTAP-containing liposomes can target transgene expression primarily to the lung. Furthermore, DOTAP, E-DC, and E-DPMC, as well as L-PE and CEBA, are fully metabolized or excreted by cells, whereas DOTMA cannot be fully metabolized by cells. Therefore, DOTAP, E-PC, E-DPMC, and L-PE, but not DOTMA, are suitable for repeated injection into mammalian hosts. Additionally, complexing the cationic lipid with a second lipid, primarily either cholesterol or DOPE can maximize transgene expression in vivo. For example, mixing a steroid, such as cholesterol, instead of DOPE with DOTAP, E-DC, E-DPMC, DOTMA, or DDAB, substantially increases transgene expression in vivo.

Particular cells and tissues may be targeted, depending upon the route of administration and the site of administration. For example, transfection of a tissue which is closest to the site of injection in the direction of blood flow may be transfected in the absence of any specific targeting. Specific cationic lipid can target cationic lipid carriers to specific cell types in vivo after systemic injection. Additionally, if desired, the lipid carriers may be modified to direct the lipid carriers to particular types of cells using site-directing molecules. Thus antibodies or ligands for particular receptors may be employed, with a target cell associated with a particular surface protein. For example, with the AIDS virus, the AIDS virus is primarily directed to cells having the CD4 surface protein. By having anti-CD4 antibody bound to the surface of the lipid carrier, the lipid carrier may be directed primarily to T-helper cells. A particular ligand or antibody may be conjugated to the lipid carrier in accordance with conventional ways, either by conjugating the site-directing molecule to a lipid for incorporation into the lipid bilayer or by providing for a linking group on a lipid present in the bilayer for linking to a functionality of the site-directing compound. Such techniques are well known to those skilled in the art. Ligand-directed DNA-polycation complexes have been shown to transfect to hepatocytes in the liver after iv injection; the ability to transfect other cell types or tissue types by this approach has not been demonstrated. Non-cationic lipid carriers, particularly pH sensitive liposomes, offer another potentially attractive approach to in vivo gene therapy. However, as compared to cationic liposomes, pH sensitive liposomes are less efficient in capturing DNA and delivering DNA intracellularly and may be inactivated in the presence of serum, thus limiting their iv use.

Unexpectedly, either the liposomal lipid composition or the mean diameter of the lipid carriers (when in particle form such as a liposome) injected can dramatically affect the level of transgene expression produced in vivo. Thus, the liposomal lipid compositions generally have a composition of 50% molar ratio of cationic lipid to non-cationic lipid, but may range from 5% to 100%. The diameter of the lipid carriers should generally be within the range of 100 mm to 10 micron. Cationic lipid carrier-DNA complexes wherein the lipid carriers range from 100 nanometers to several microns in diameter can produce significant levels of transgene expression after systemic introduction into a mammalian host.

The use of lipid carriers of greater than 500 nanometers (in other words multilamellar vesicles (MLV) or large unilamellar vesicles (LUV)) can in certain cases significantly increase the level of transgene expression achieved in a mammalian host when compared to small unilamellar vesicles (SUV). MLV and LUV are prepared by vortexing rather than sonicating after addition of the aqueous material to the dry lipid film. If desired, the resulting lipid carriers can be extruded under high pressure through sized polycarbonate membranes to achieve more uniform size distributions.

Also unexpectedly, the use of particular nucleic acid to lipid carrier ratio also is essential; the ratios used determine whether and to what level transgenes are expressed in vivo and needs to be optimized, depending upon various factors including the nature of the construct, the size and lipid composition of the lipid carrier and whether it is MLV or SUV, the route of administration and the host mammal. As an example, using a reporter gene CAT (chloramphenicol acetyl transferase), an approximately 1:1 (range 0.5:1 to 2:1) DNA to lipid carrier ratio ($\mu$g DNA to nmoles of the cationic lipid) produces the highest levels of gene expression in a mouse in all organs after ip administration, and an approximately 1:4 ratio, (range 2:1 to 1:7) produces the highest levels of gene expression in all organs after iv administration. In addition to achieving a high level of transgene expression in a wide variety of tissues using optimal conditions, the majority of all cells present in the lung, spleen, lymph nodes and bone marrow are transfected in vivo, as well as the majority of all endothelial cells present in the heart.

The DNA:lipid carrier ratio determines whether or not, and at what level, transgenes are expressed in mammalian hosts after systemic injection of the complexes. Several factors are important in order optimize the DNA:lipid carrier ratio. Thus, specific DNA:lipid carrier ratios are required for each type of cationic lipid used as well as for each different lipid carrier size used. To optimize, for each lipid carrier composition used, DNA must be mixed together with the lipid carriers in multiple different ratios, ranging from 4:1 to 1:10 (micrograms DNA to nanomoles cationic lipid), in order to determine which ratios result in aggregation of the DNA:lipid carrier complexes. Ratios which result in aggregation cannot be used in vivo. The ratios which do not result in aggregation are tested in animal models to determine which of the DNA:lipid carrier ratios confers the highest level of transgene expression in vivo. For example, the optimal DNA:lipid carrier ratios for SUV for DOTMA/ DOPE, DDAB/DOPE, DOTAP/DOPE, DOTAP/Chol, LPE:CEBA, DDAB:Chol, L-PE:DOPE, and E-PC/chol are 1:4, 1:3, (very low activity at all ratios), 1:6, 1:1, 1:5, 2:1, and 2:1, respectively. DNA:lipid carrier complexes must be made in appropriate physiologic solutions. The DNA:lipid carrier complexes must be mixed in physiologic solutions (approximately 290 milliosmoles) which do not themselves induce aggregation of the DNA:lipid carrier complexes. The solutions include 5% dextrose in water or normal saline.

The construction of the vector itself is also critical for producing high level in vivo expression of the transgene after aerosol or systemic administration. Optimally, the vector either lacks an intron or contains an expanded 5" intron which does not result in aberrant splicing. In addition, a strong promoter-enhancer element, such as the AD169 stain of HCMV or the addition of a strong heterologous enhancer from for example an SV.40 or HCMVIEI gene to a weak promoter, such as that from a CFTR gene confers high level in vivo expression of the transgene. Using appropriately constructed vectors, high level in vivo expression may be obtained after systemic injection of the vector alone, or more efficiently, when completed to a cationic lipid carrier. Furthermore, use of the CFTR promoter together with a heterologous enhancer can be used to produce significant transgene expression in a tissue and cell-type specific fashion which approximates the endogenous pattern of CFTR gene expression.

Cell surface receptors for cationic lipid carriers can be used to both regulate and confer target cell specificity on transgene expression in mammalian hosts. Cationic lipid carrier:DNA complexes are internalized by cells by a classical receptor-mediated endocytosis (see FIG. 7) using cell surface receptors which contain specific binding sites for, and are able to internalize, cationic molecules. Using agents such sa cytokines, growth factors, other soluble proteins and certain drugs, it is thus possible to selectively up or down regulate these cation-binding receptors. The rate of up or down regulation of these receptors by the appropriate agent will allow selection of specific cells for enhanced or reduced levels of transfection in vivo. Furthermore, surprisingly cell surface receptors for naked DNA can be used both to regulate and to confer target cells specificity on transgenic expression in mammalian host.

The most frequent interaction between DOTMA lipid carriers, either the uni- or multilamellar lipid carriers, complexed to plasmid DNA and the various cell types (for example, CV-1 monkey kidney cells, U937 human myelomonocytic leukemia cells, K562, MEL (murine eythroblastic leukemia cells), rat alveolar macrophages, and alveolar type II cells), is that of lipid carrier adhesion and internalization. This interaction is common to well-defined examples of receptor-mediated endocytosis. All cells which appear to have contacted cationic lipid carrier:DNA complexes ingest the complexes after binding to the plasma membrane. All these cell types demonstrate the same classical receptor-mediated endocytic pathway of internalization.

The mammalian host may be any mammal, particularly a mammal having symptoms of a genetically-based disorder. Thus, the subject application finds use in domestic animals, feed stock, such as bovine, ovine, and porcine, as well as primates, particularly humans. The mammalian host may be pregnant, and the intended recipient of the gene-based therapy may be either the gravid female or the fetus or both.

In the method of the invention, transfection in vivo is obtained by introducing a therapeutic transcription or expression vector into the mammalian host, ether as naked DNA or complexed to lipid carriers, particularly cationic lipid carriers. The constructs may provide for integration into the host cell genome for stable maintenance of the transgene or for episomal expression of the transgene. The introduction into the mammalian host may be by any of several routes, including intravenous or intraperitoneal injection, intratracheally, intrathecally, parenterally, intraarticularly, intramuscularly, etc. Of particular interest is the introduction of a therapeutic expression vector into a circulating bodily fluid. Thus, iv administration and intrathecal administration are of particular interest since the vector may be widely disseminated following such a route of administration. Any physiologically acceptable medium may be employed for administering the DNA or lipid carriers, such as deionized water, saline, phosphate-buffered saline, 5% dextrose in water, and the like, depending upon the route of administration. Other components may be included in the formulation such as buffers, stabilizers, biocides, etc. These components have found extensive exemplification in the literature and need not be described in particular here.

The amount of lipid carriers used will be sufficient to provide for adequate dissemination to a variety of tissues after entry of the DNA or complexes into the bloodstream and to provide for a therapeutic level of expression in transfected tissues. A therapeutic level of expression is a sufficient amount of expression to treat or palliate a disease of the host mammal. In addition, the dose of the plasmid DNA expression vector used must be sufficient to produce significant level of transgene expression in multiple tissues in vivo for example, $\geq 1$ mg of an expression plasmid alone is injected into a mouse to achieve high level expression of the CAT gene in multiple tissues. Other DNA sequences, such as adenovirus VA genes can be included in the administration medium and be co-transfected with the gene of interest. The presence of genes coding for the adenovirus VA gene product may significantly enhance the translation of mRNA transcribed from the plasmid.

The level and tissues of expression of the recombinant gene may be determined at the mRNA level and/or at the level of polypeptide or protein. Gene product may be quantitated by measuring its biological activity in tissues. For example, enzymatic activity can be measured by biological assay or by identifying the gene product in transfected cells by immunostaining techniques such as probing with an antibody which specifically recognizes the gene product or a reporter gene product present in the expression cassette. Alternatively, potential therapeutic effects of the gene product can measured, for example where the DNA sequence of interest encodes GM-CSF, by determining the effects of gene expression on survival of lethally irradiated animals in which the GM-CSF transgene is expressed. Production of significant amounts of a transgene product will substantially prolong the survival of these mice.

Where expression of the polypeptide/protein or even the mRNA itself confers a changed biochemical phenotype upon the host, the presence of a new phenotype or absence of an old phenotype may be evaluated; for example, as a result of transfection of the host cells, there may be enhanced production of pre-existing desirable products formerly produced in insufficient quantities or there may be reduction or even suppression of an undesirable gene product using antisense, ribozyme or co-suppression technologies; in the case of suppression, a reduction of the gene product may be determined. Typically, the therapeutic cassette is not integrated into the host cell genome. If necessary, the treatment can be repeated on an ad hoc basis depending upon the results achieved. If the treatment is repeated, the mammalian host can be monitored to ensure that there is no adverse immune response to the treatment.

The subject compositions can be provided for use in one or more procedures. Kits will usually include the DNA either as naked DNA or complexed to lipid carriers. Additionally, lipid carriers may be provided in a separate container for complexing with the provided DNA. The DNA either for direct injection or for complexing with lipid carriers, or the lipid carrier/DNA complexes may be present as concentrates which may be further diluted prior to use or they may be provided at the concentration of use, where the vials may include one or more dosages. Conveniently, single dosages may be provided in syringes, contained in sterilized containers, so that the physicians or veterinarian may employ the syringes directly, where the syringes will have the desired amount and concentration of agents. Thus, the kit may have a plurality of syringes containing the DNA or the DNA/lipid carrier complexes in appropriate proportional amounts. When the syringes contain the formulation for direct use, usually there will be no need for other reagents for use with the method.

The invention finds use in in vivo treatment and/or palliation of a number of diseases. In vivo replacement of a gene can be accomplished by techniques such as homologous recombination or initial knockout of the aberrant gene and subsequent replacement with the desired transgene.

Uses

Uses of the subject invention include but are not limited to the following. The present invention is particularly useful for the delivery of substances into the lung and appropriate extrapulmonary tissues for the prevention and/or treatment of the multi-organ system manifestations of CF. Specifically, it is useful for the prevention, treatment, and cure of the disease manifestations of CF in tissues, including the lung, liver, pancreas, and colon.

For the treat of cystic fibrosis a functional CFTR gene, or a nucleic acid sequence encoding a molecule having wild-type CFTR activity is administered. The gene can be administered prophylactically, as well as in response to clinical manifestations of the disease, for both the prevention and/or treatment of this disorder. The invention also finds use for the delivery of substances into the systematic circulation via the lung. The amount of CFTR produced can be controlled by modifying the dose administered, the frequency and duration of dosing, the strength of the promoter and enhancer elements used to direct transcription of the transgenes and the efficiency and target specificity of the lipid carrier user.

The instant means also find use in antisense therapy, for the delivery of oligonucleotides able to hybridize to specific complementary sequences of a defective or mutant CFTR gene, thereby inhibiting the transcription and/or translation of these sequences. Thus, DNA or RNA coding for proteins necessary for the progress of a particular disease, can be targeted, thereby disrupting the disease process. For a review of antisense therapy and oligonucleotides useful in the same, see, Uhlmann, E. Peyman, A., Chem. Rev. (1990) 90:543–584.

The following examples are provided for illustrative purposes only and are not intended to limit the scope of the present invention.

EXAMPLES

The practice of the present invention employs unless otherwise indicated, conventional techniques of cell culture, molecular biology, microbiology, recombinant DNA, and immunology, which are within the skill of the art. Such techniques are explained fully in the literature. See, e.g., Sambrook, et al., Molecular Cloning: A Laboratory Manual, Second Edition (1989) Vols. 1–3; DNA Cloning (1985) Vols. I and II, D. N. Glover (ed.); Nucleic Acid Hybridization (1984), B. D. Hames, et al., (eds.); Perbal, B., A Practical Guide to Molecular Cloning (1984); Methods in Enzymology (the series), Academic Press, Inc.; Vectors: A Survey of Molecular Cloning Vectors and Their Uses (1987), R. L. Rodriguez, et al., (eds.), Butterworths; and Miller, J. H., et al., Experiments in Molecular Genetics (1972) Cold Spring Harbor Laboratory.

We have not modified the INTOX chamber, Up to 48 mice can be exposed simultaneously to an aerosol dose. Approximately 0.02% of the total volume of DNA:liposome complex solution placed in the nebulizer is actually deposited in the lungs of each individual mouse.

Example 1

Preparation of Plasmids for in vivo Gene Therapy

Details regarding the plasmids that have been used for transfection of mammalian cells are as follows.

pRSVCAT

Construction of this plasmid described in Gorman et al., *Proc. Nat. Acad. Sciences (USA)* (1982), 79:6777–6781. In the pRSVCAT plasmid, the 3'-RSVLTR is juxtaposed as a promoter upstream from CAT encoding sequences. The distance between the LTR transcriptional start site and the CAT initiation codon (the first AUG downstream from the start site) is about 70 bp.

p5'PRL3CAT

Construction of this plasmid is described in Sakai et al., *Genes and Development* (1988) 2:1144–1154.

pSIS-CAt

Construction of this plasmid is described in Huang and Gorman, *Nucleic Acids Research* (1990) 18:937–948.

pZN20

Figures 2, 19A:
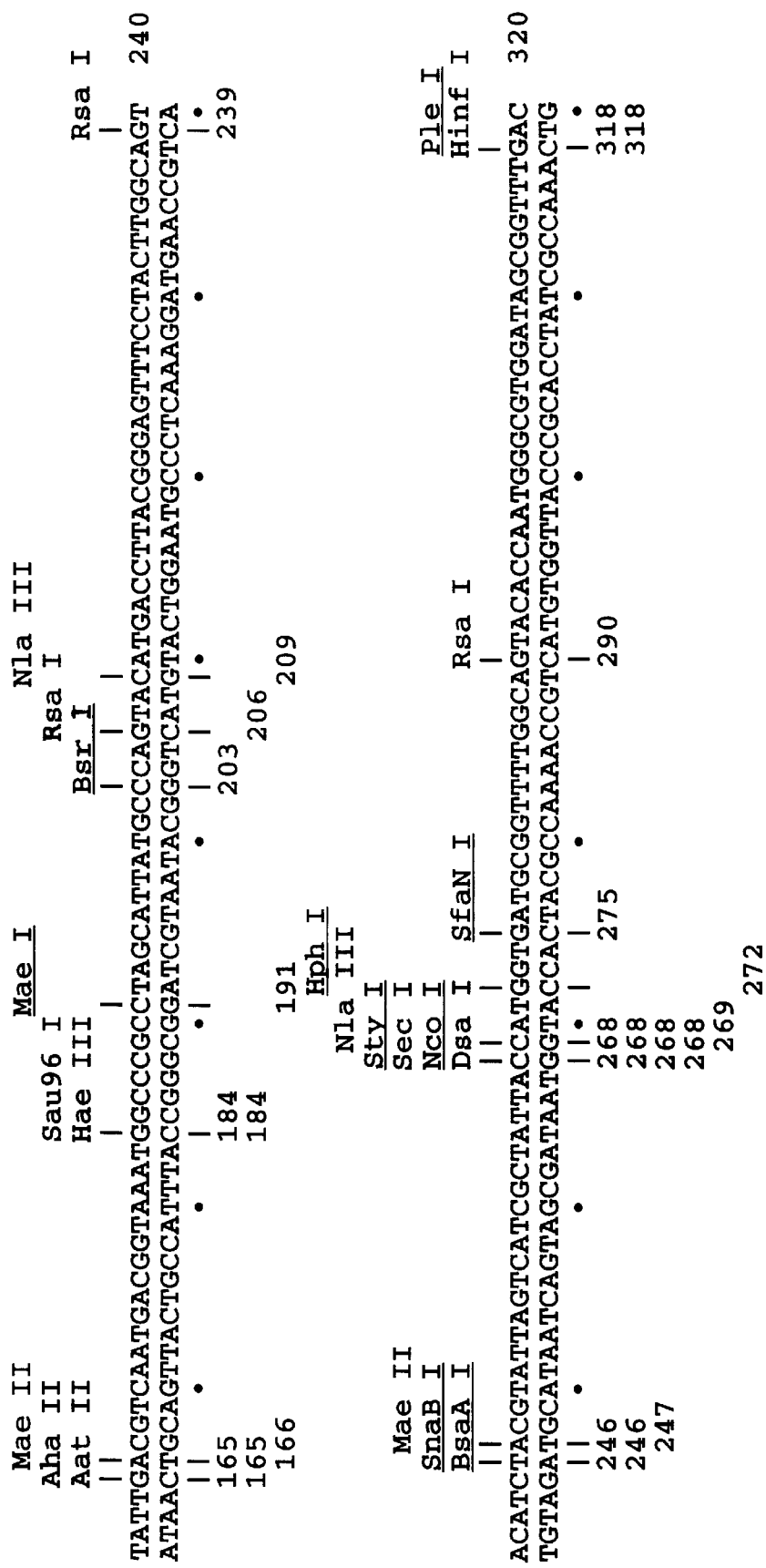
Figures 3, 19A:
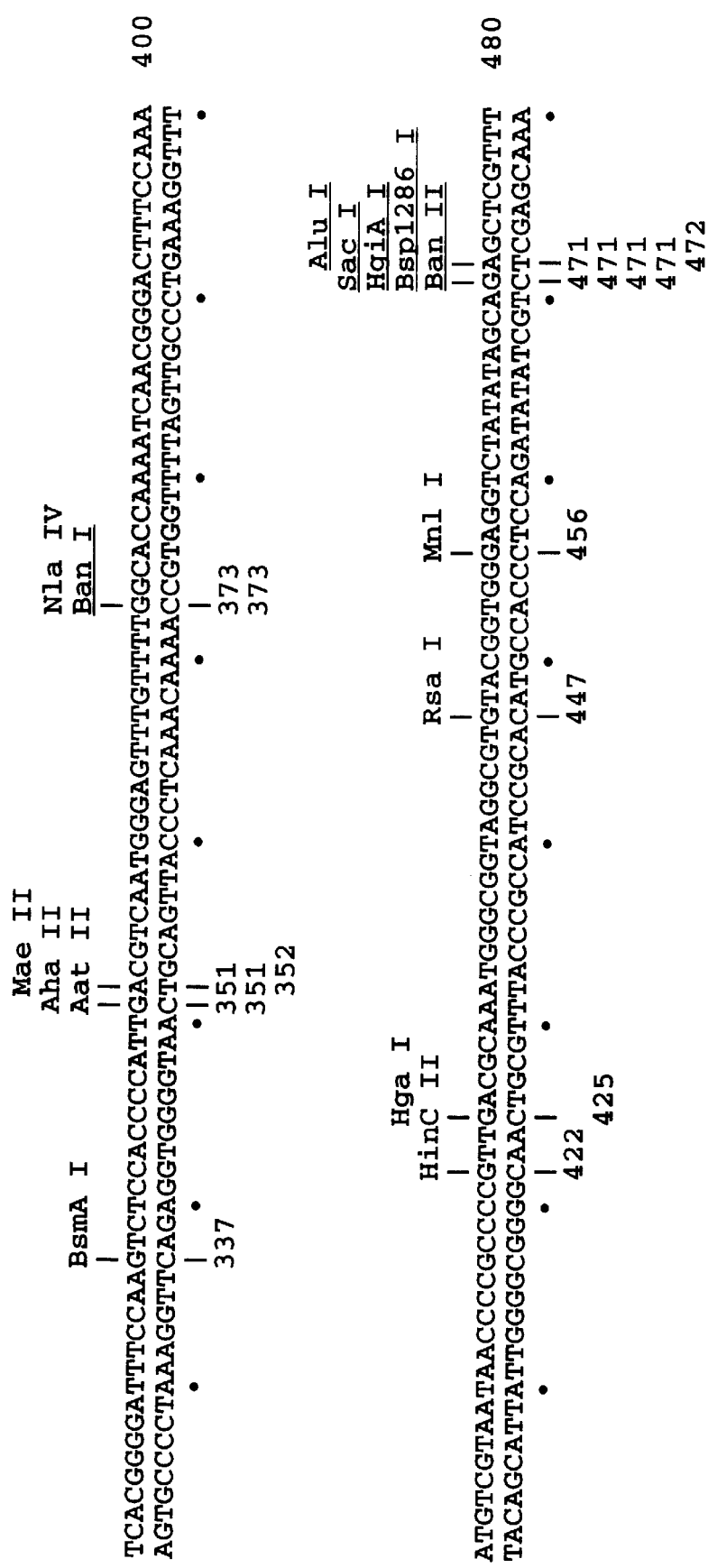
Figure 19C-3:
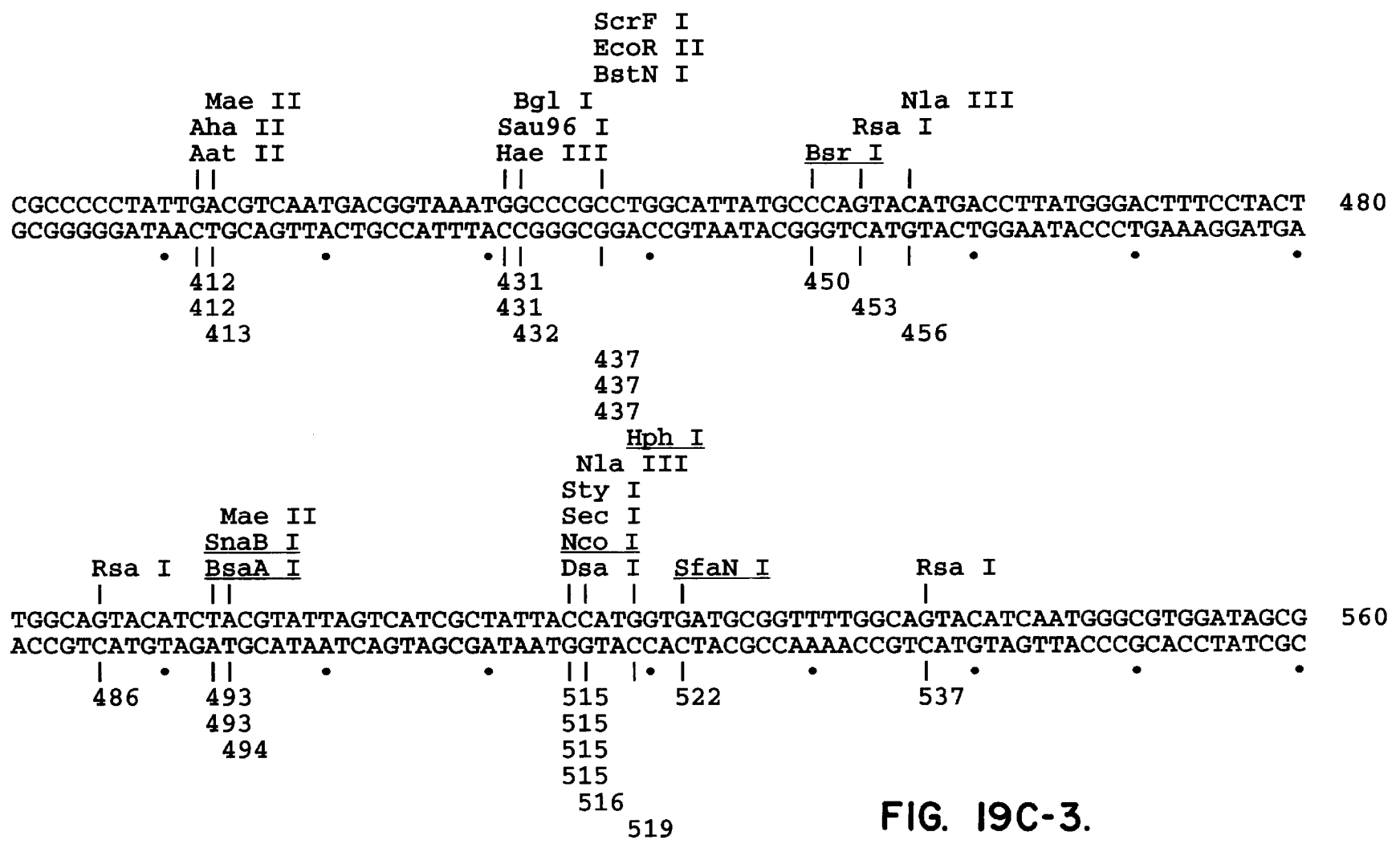
Figure 19C-5:
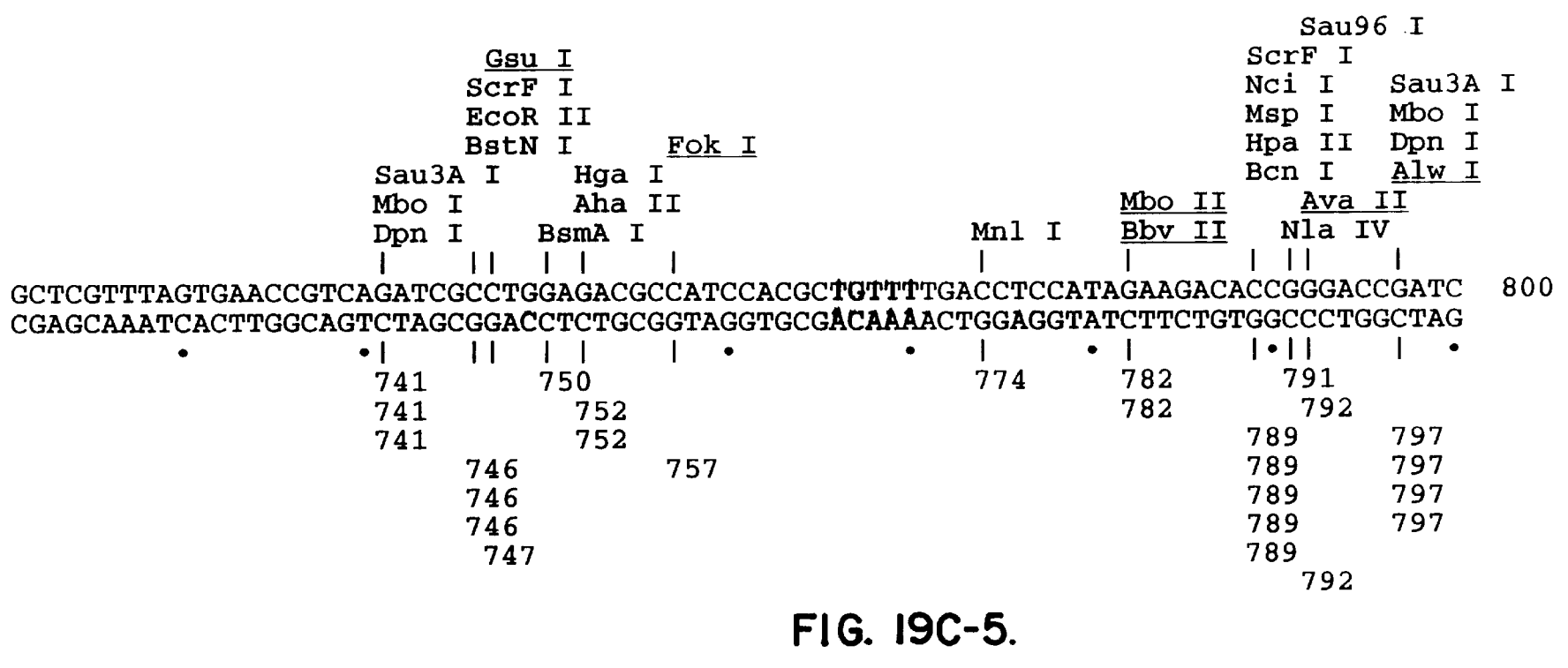
Figure 19C-6:
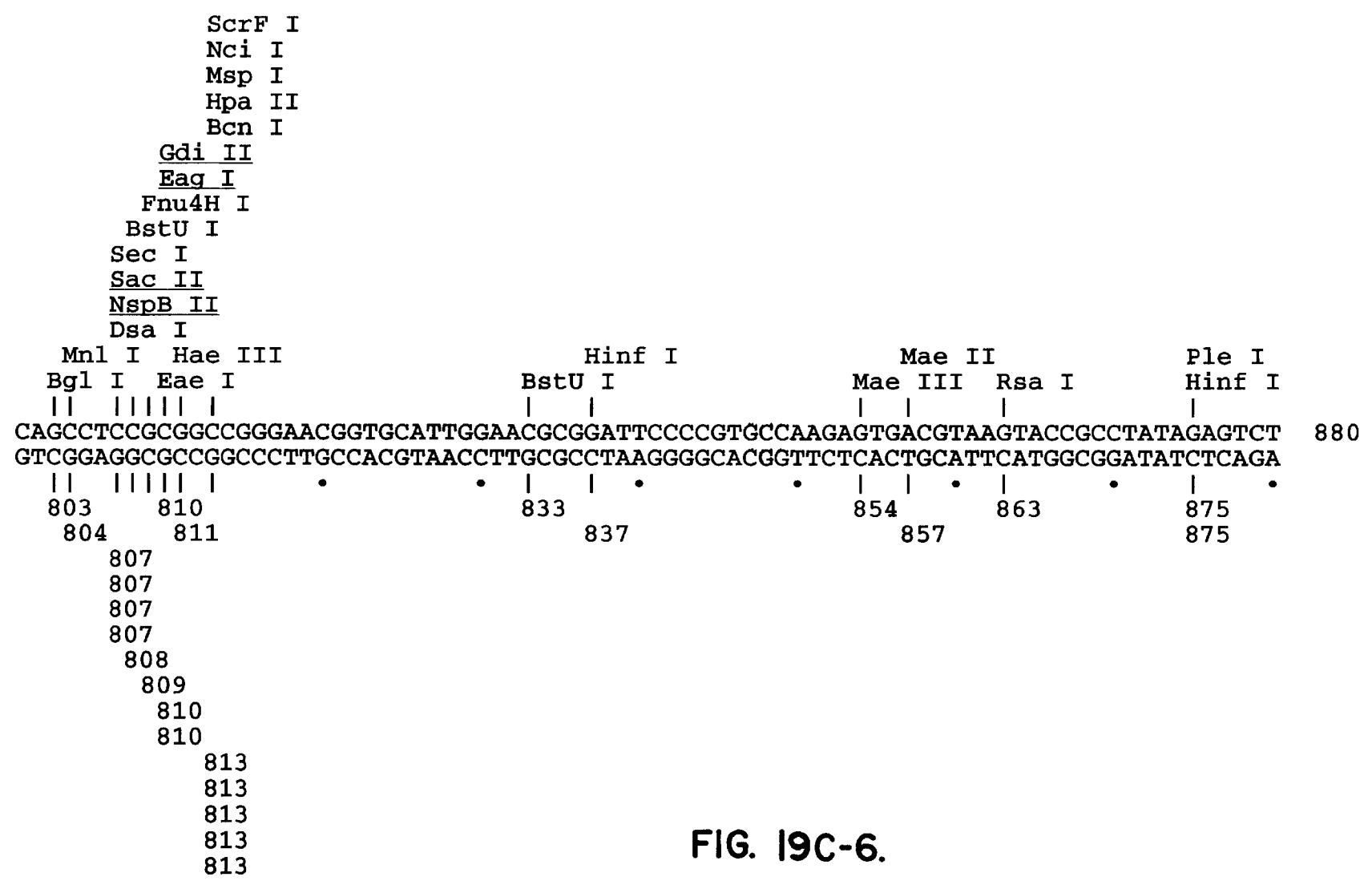

Construction of this plasmid is illustrated in FIG. 3. The plasmid was prepared as follows. pCATwt760 (Stinski and Roehr (1985) *J. Virol.* 55:431–441) was treated with HindIII and the fragment containing the HCMV base IE 1 enhancer and promoter element purified. The isolated fragment was then cloned into the HindIII site of pSP72 (Promega) creating pZN9. Clones were screened in which the enhancer and promoter element is as shown in FIG. 3. Following partial HindIII digestion of pZN9, the blunt ends were filled in with DNA polymerase I Klenow fragment. The resulting clone pZN12 has lost the HindIII site 5' to the enhancer and promoter element. pZN12 was then treated with Nco1 and HindIII and the large Nco1-HindIII fragment purified and ligated to a purified small Nco1-HindIII fragment from pBC12/CMV/IL-2 (Cullen, *Cell* (1986) 46:973–982. pBC12/CMV/IL-2 contains the HCMV promoter from the AD169 strain. The resulting clone was pZN13. pZN13 was partially digested with BamH1, filled in with DNA polymerase I Klenow fragment and the resulting clones screened for the clone which has lost the BamHI site at the 5' end of the enhancer and promoter element. The resulting clone was called pZN17. pZN17 was treated with HindIII and BamHI and the resulting HindIII-BamHI large fragment was purified and ligated to a purified small HindIII-BamHI fragment obtained from pSV2-CAT (Gorman et al. (1982), *Molecular Cell Biology*, 2:1044–1051). The resulting clone was pZN20. The full restriction map of HCMV (Towne) is shown in FIG. 19A SEQ ID NO: 1. HCMV (AD169) is shown in FIG. 19C SEQ ID NO: 2. A comparison of the two promoters is shown in FIG. 19B. Significantly more expression is obtained when a promoter from the AD169 strain is used as compared to one from the Towne strain. pZN20 contains a composite promoter which has the Towne sequence 5' of the NcoI site and the AD169 sequence 3' of the NcoI site. The NcoI site is indicated by the asterisk in FIG. 19B. pZN20 has this composite HCMV promoter followed by the CAT gene, SV40 t-intron and SV40 polyA addition site.

pZN27

Figure 7A:
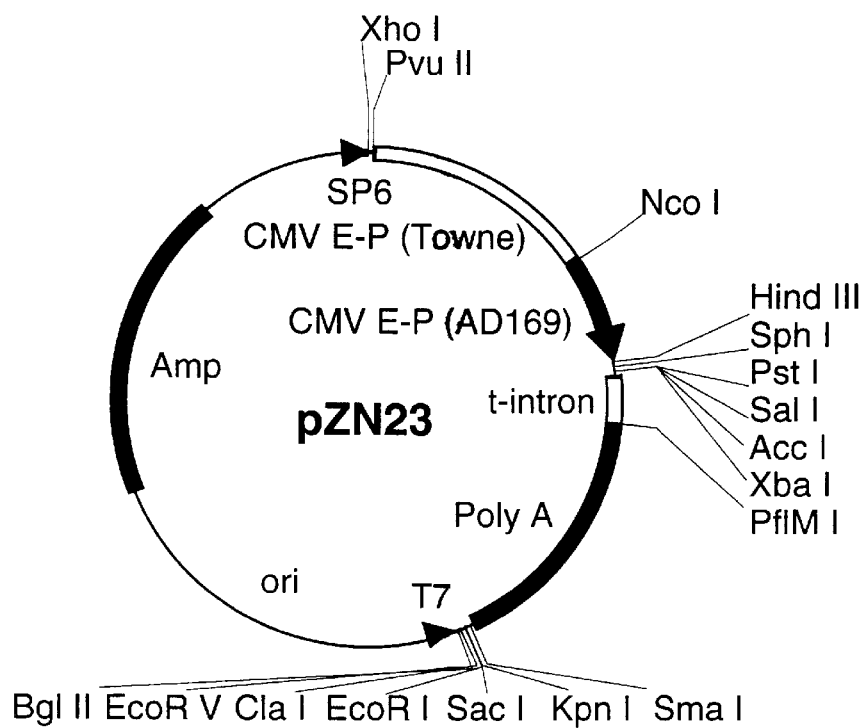
FIG. 7 shows the construction of plasmid pZN27.
Figure 7B:
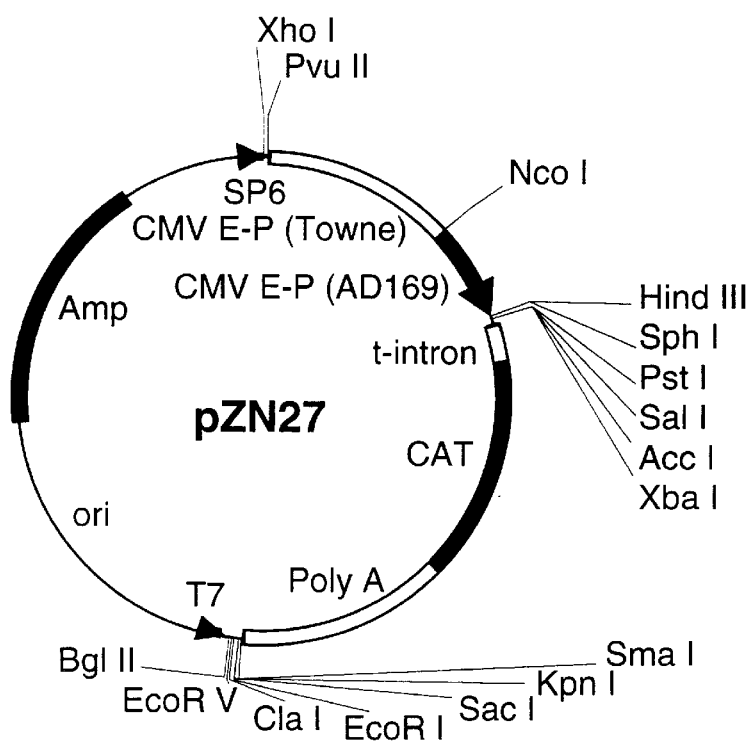

Construction of this plasmid is illustrated in FIG. 7. pZN27 contains the composite HCMV promoter followed in order by the SV40 t-intron, the CAT coding sequence and the SV40 polyA addition site pZN46

Figures 1, 27A:
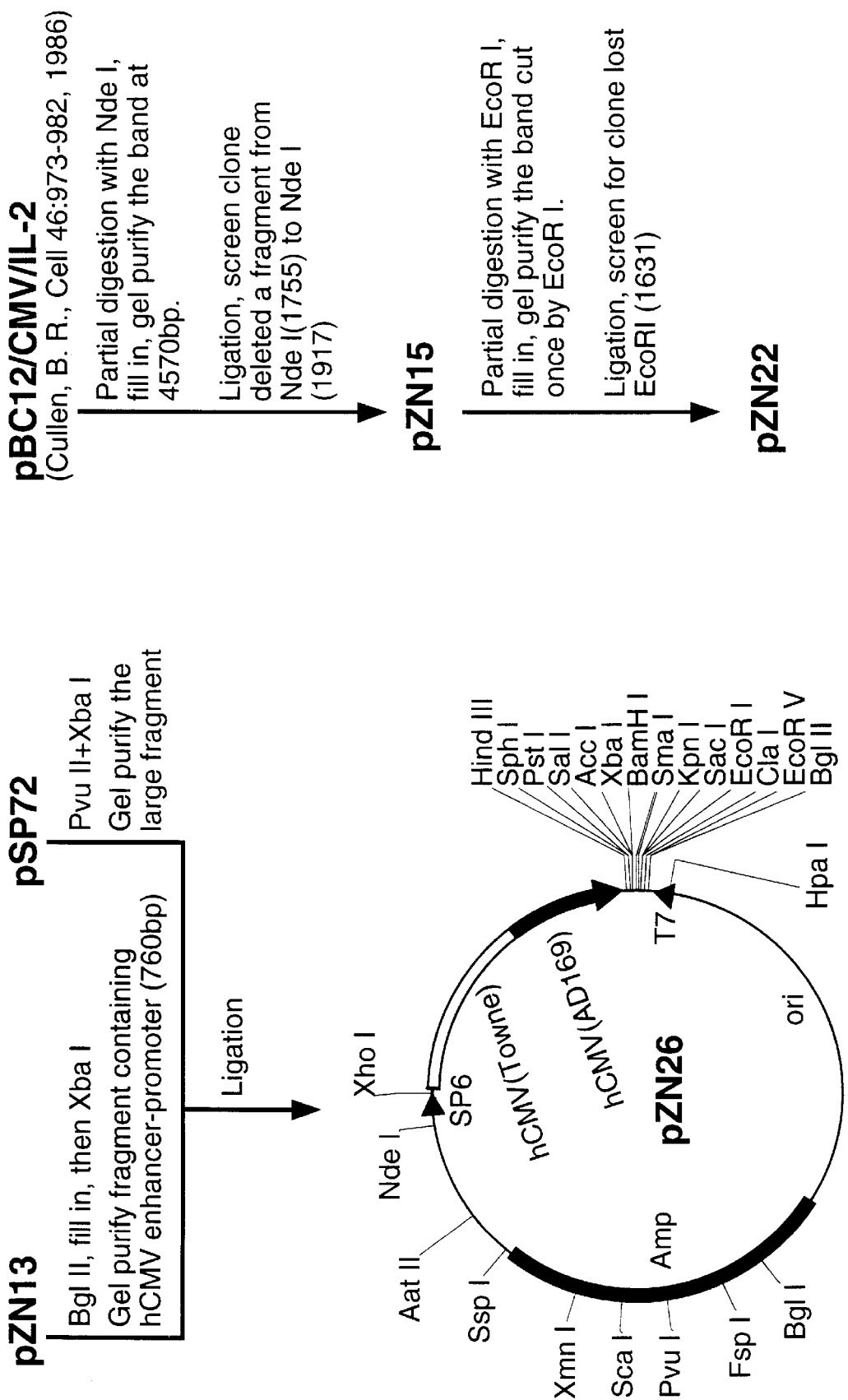
FIG. 27A shows the construction of plasmids pZN30 and pZN31 and FIG. 27B shows the construction of plasmid pZN46.
Figures 2, 27A:
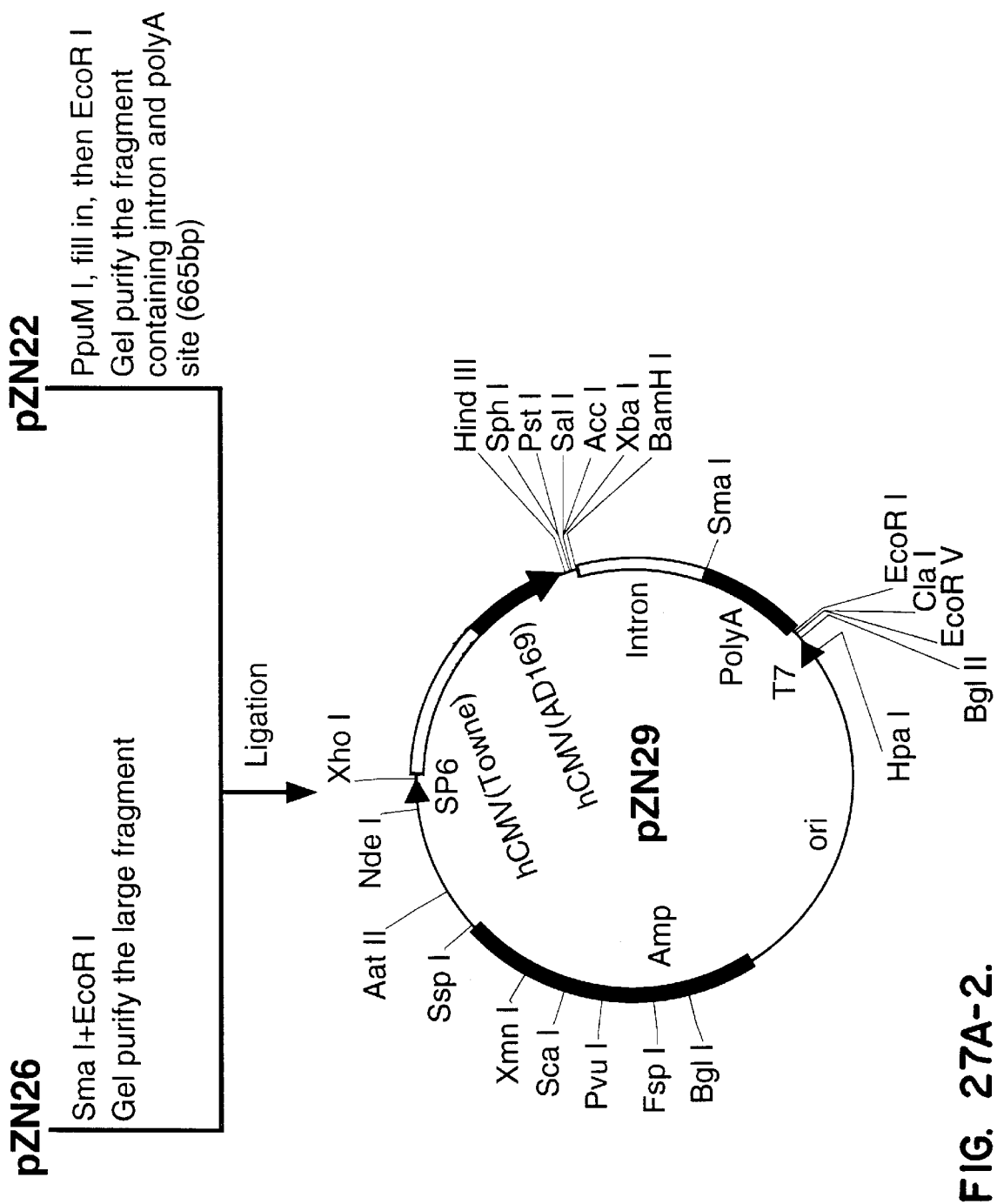
Figures 3, 27A:
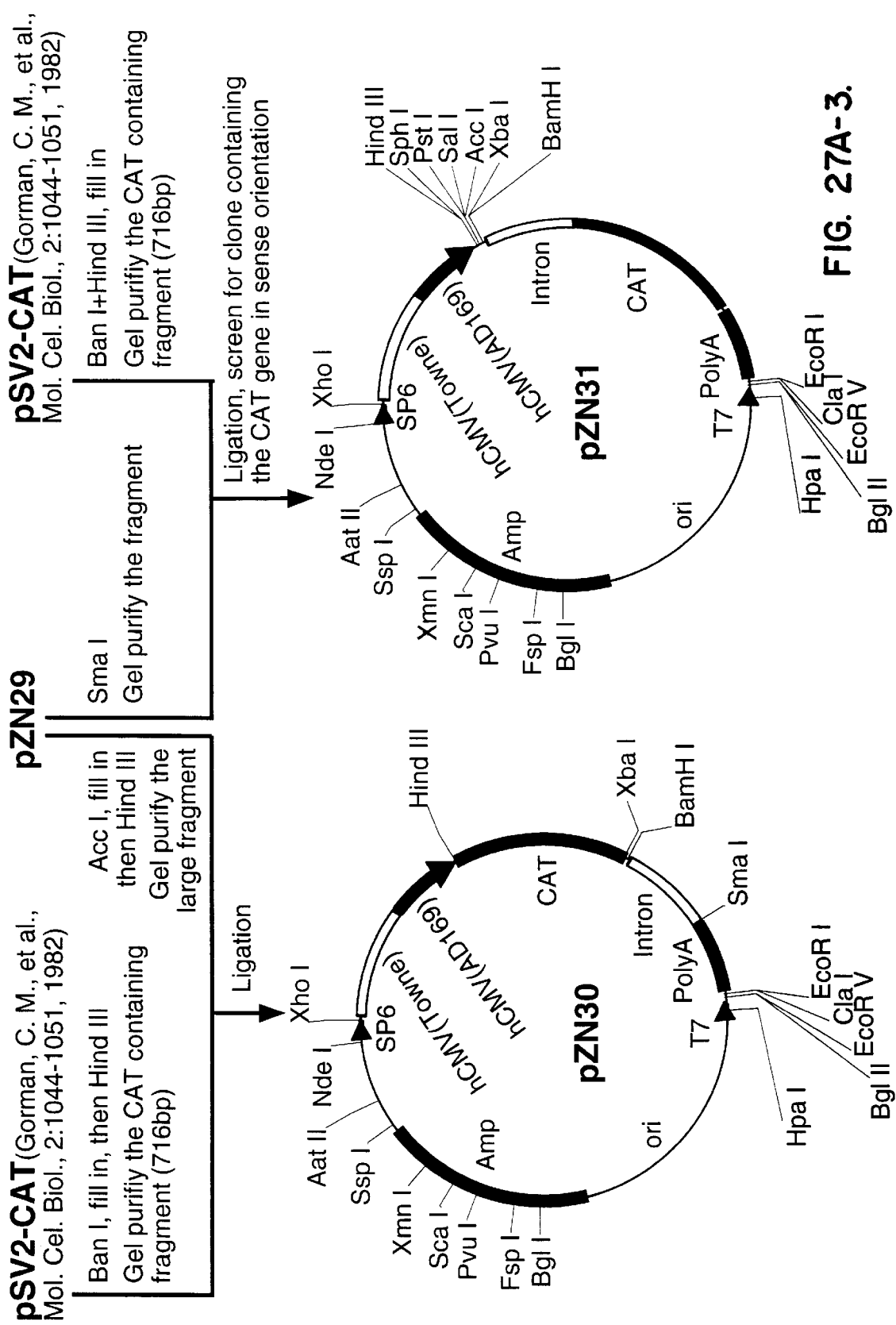
Figure 27B:
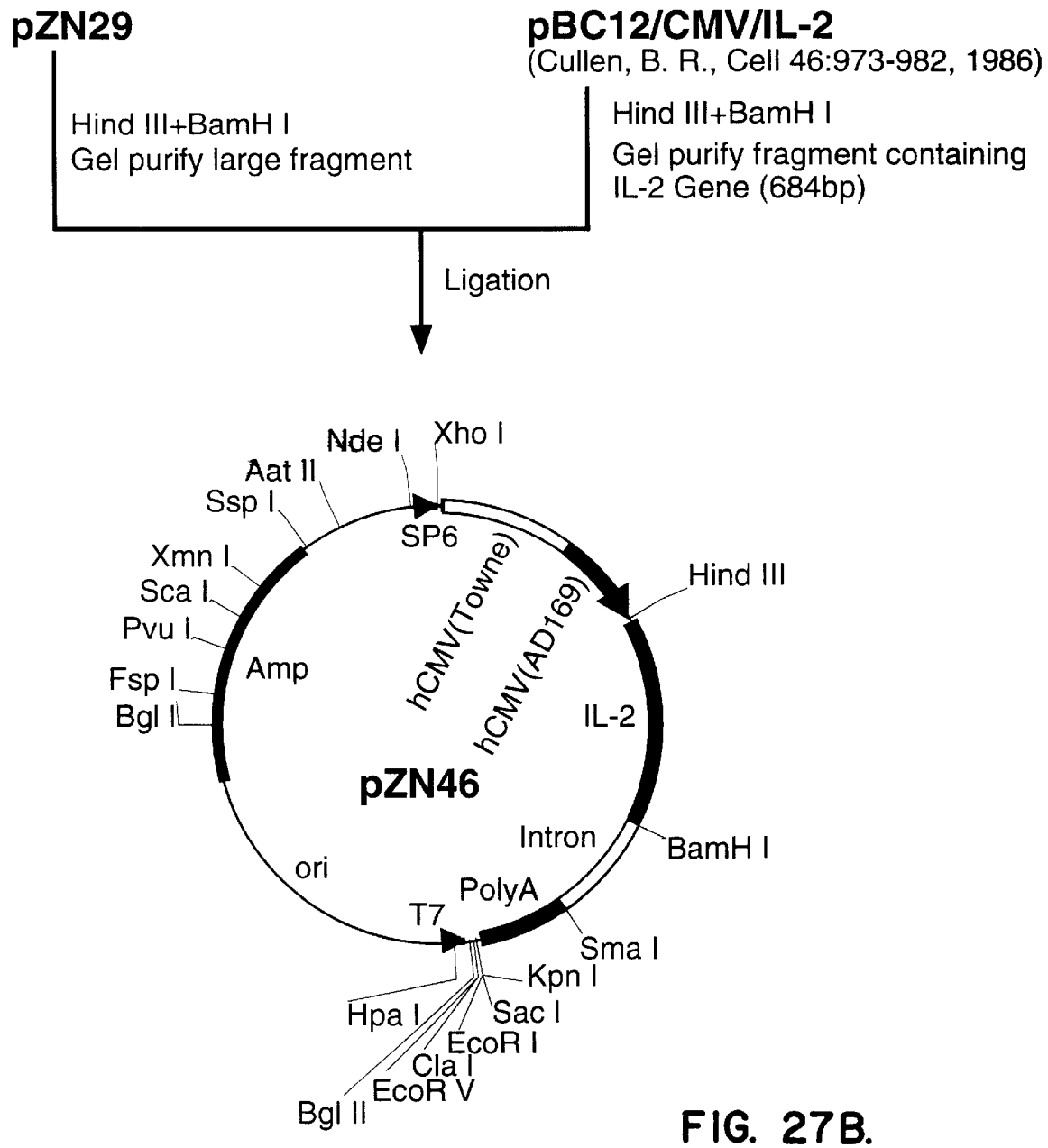
Figures 2, 28A:
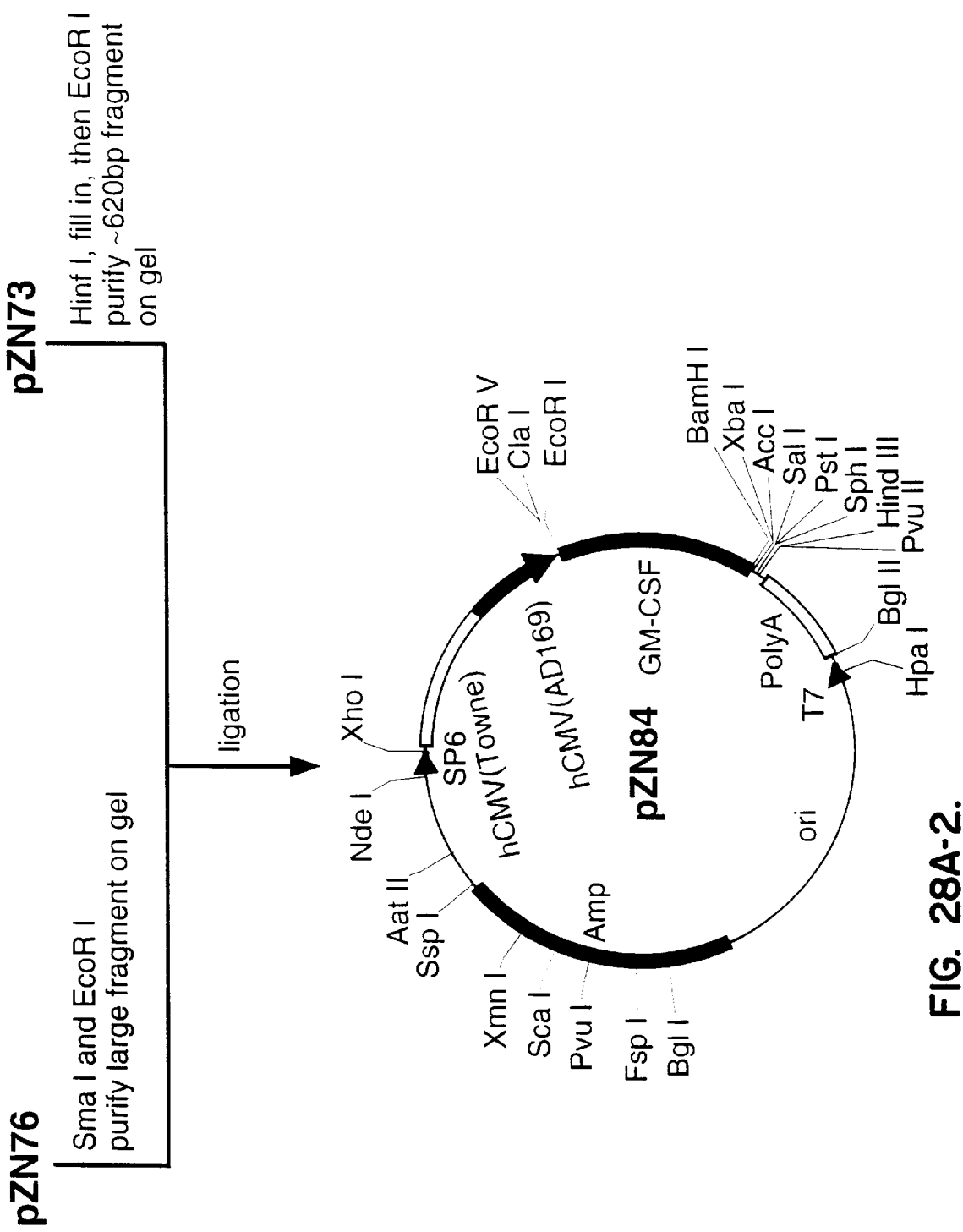
FIG. 28A shows the construction of plasmids pZN76, pZN73, and pZN84
Figure 28B:
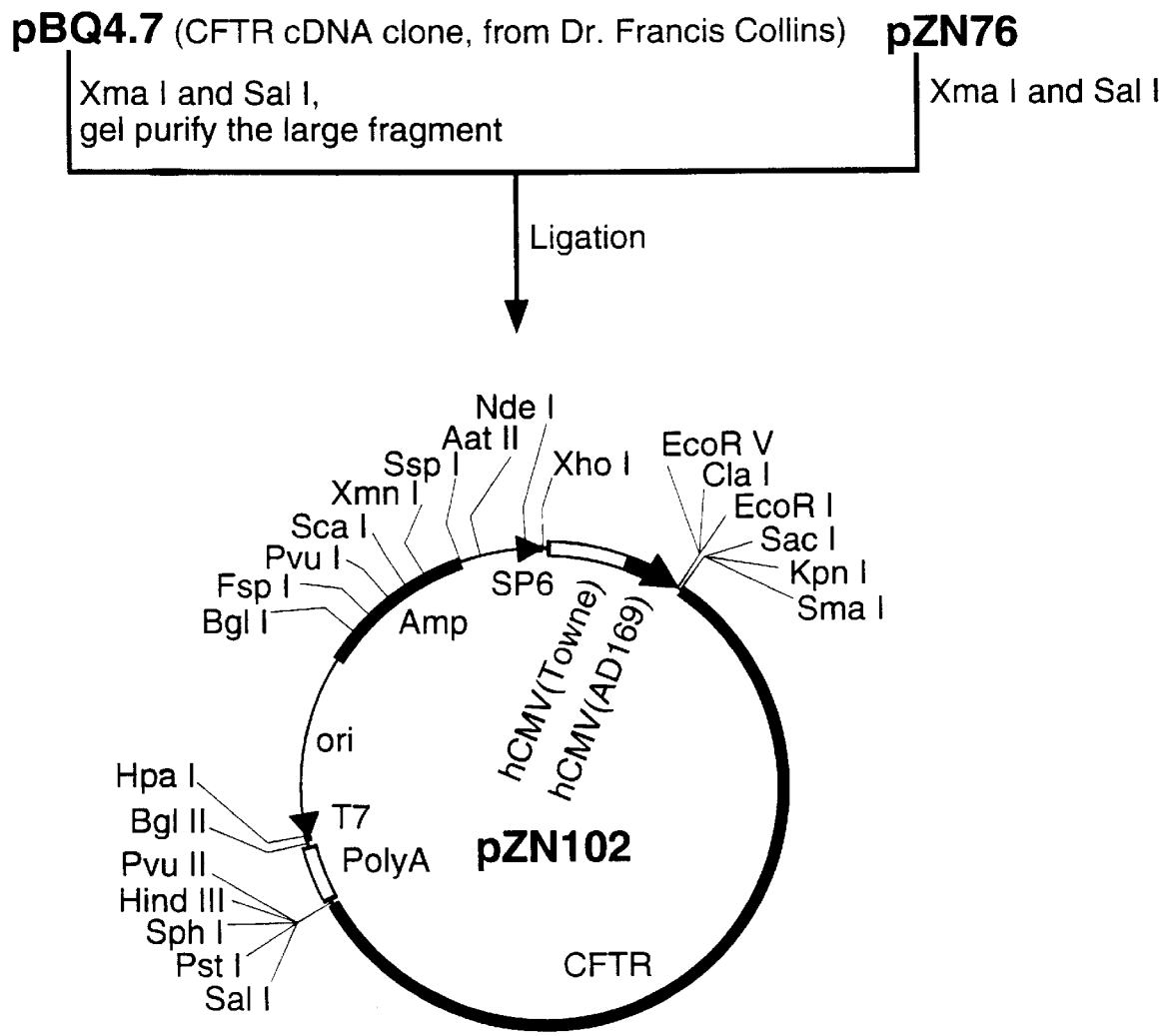
FIG. 28B shows the construction of plasmid pZN102.

Construction of this plasmid is shown in FIG. 27A and FIG. 27B. pZN46 contains the composite HCMV promoter, followed by the human IL2 gene, rat preproinsulin 2 intron and polyA addition site from the rat preproinsulin 2 gene. These last three components were derived from pBC12/CMV/IL-2 plasmid of Cullen (*Cell* 46:973–982 (1986). The rat preproinsulin2 intron was modified by deleting an internal 162 base pair NdeI fragment.

pZN32

Figure 10:
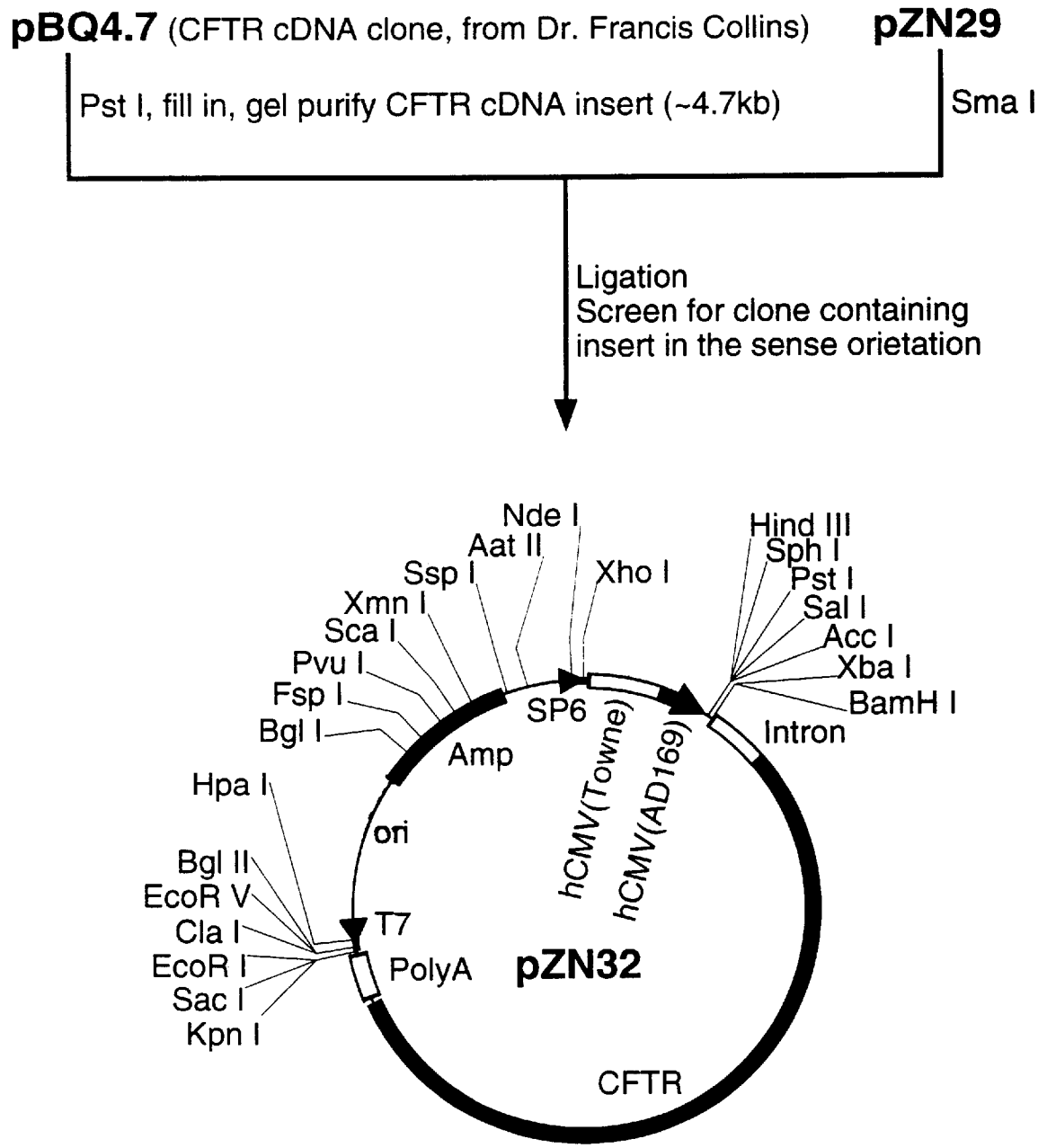
FIG. 10 shows the construction of plasmid pZN32.

Construction of this plasmid is shown in FIG. 10. pZN32 contains the composite HCMV promoter followed in order by the modified rat preproinsulin2 intron described for pZN46, CFTR cDNA, and rat preproinsulin2 gene polyA addition site as described for pZN46. CFTR cDNA was obtained from pBQ4.7 from F. Collins (Univ. of Michigan).

pZN51

Construction of this plasmid is shown in FIG. 11. pZN51 contains the composite HCMV promoter followed by the CAT coding sequence and the SV40 polyA site.

pZN60, pZN61, pZN62, pZN63

Construction of these plasmids is shown in FIG. 19. pZN60 contains the HCMV composite promoter followed by the modified rat preproinsulin 2 intron, the CAT coding sequence, and the SV40 polyA addition site. pZN61 is identical to pZN60 but contains an additional 166 base pairs 5' to the intron. This additional DNA is the 166 BP immediately 5' of the intron in the pBC12/CMV/IL-2 plasmid and may contain rat preproinsulin 2 gene coding sequence. pZN62 is similar to pZN60 except that the intron is 3' of the CAT coding sequence rather than 5' as in pZN60. pZN63 is identical to pZN62 except for the additional 166 base pairs 5' to the intron. This is the same additional sequence described for pZN61.

Example 2

Expression of chloramphenicol acetyltransferase (CAT) gene, in rodent lungs following aerosolized delivery of lipid carrier-nucleic acid complexes The lipid carriers used were plasmid pRSV-CAT, as described by Gorman, et al., *Proc. Natl. Acad. Sci. USA* (1982) 79:6777–6781; and Juang, and Gorman, *Mol. Cell. Biol.* (1990) 10:1805–1810; a plasmid containing the CAT gene driven by the RSV long terminal repeat; and plasmid pRSV-β-gal, as described by Hazinski et al, *Am. J. Respir. Cell Mol. Biol.* (1991) 4:206–209.

The pRSV-CAT plasmid was complexed to lipid carriers and administered to 25 gram female BALB/c mice as follows. Two mg of pRSV-CAT was mixed with 4 μmoles of DOTMA (GIBCO BRL, Grand Island, N.Y./cholesterol (2:1) small unilamellar liposomes in phosphate buffered saline and then nebulized in an Acorn I nebulizer (Marquest Medical Products, Inc., Inglewood Colo.) to groups of rats or mice in an Intox nose-only exposure chamber (Intox Products, Albuquerque, N.M.). The same procedure was followed with 0.5 mg pRSV-CAT mixed with 1.0 μmol DOTMA-cholesterol (2:1), as well as 2.0 mg pRSV-CAT alone. Two to five days later, animals were sacrificed and lungs collected. Lungs were also collected from untreated controls. The lungs were homogenized and cells disrupted with three freeze-thaw cycles. CAT activity in aliquots from the lung extracts was measured using a standard assay as described by Wolff, et al., *Science* (1990) 247:1465–1468.

Results

Figure 20:
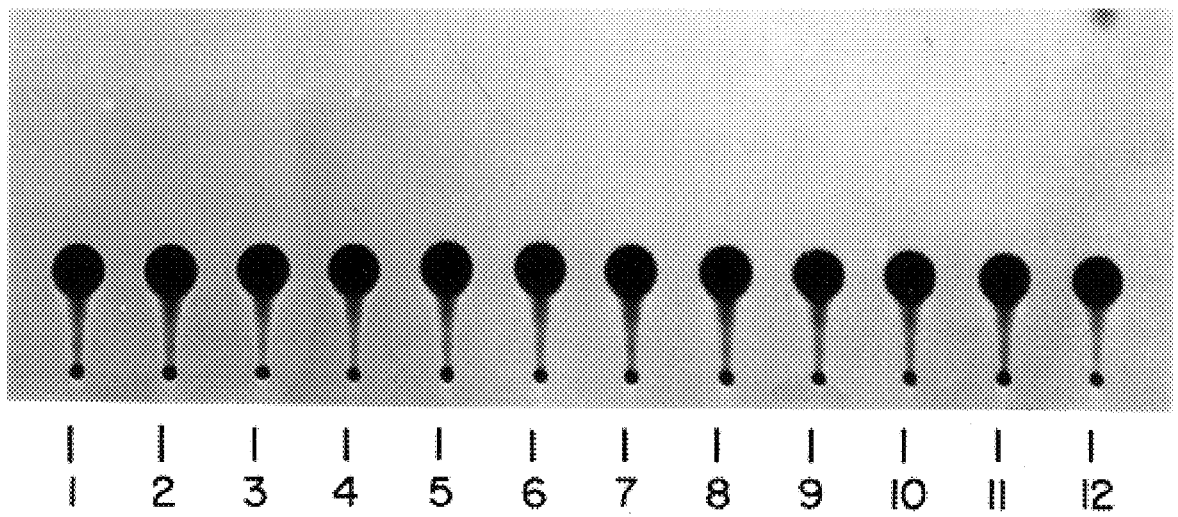
FIG. 20 demonstrates that aerosol administration of pRSV-CAT-DOTMA: cholesterol complexes resulted in expression of the CAT gene in mouse lungs. Lanes 1–3 were derived from mice receiving no treatment; lanes 4–6 represent mice administered 0.5 mg pRSV-CAT with 1.0 µmole DOTMA-cholesterol liposomes; lanes 7–9 were derived from mice receiving 2.0 mg pRSV-CAT alone; and lanes 10–12 represent mice given 2.0 mg pRSV-CAT with 4.0 µmol DOTMA-cholesterol liposomes in a 2 to 1 molar ratio. The CAT gene is not normally present in mammalian cells; the results thus indicate that the lung was successfully transfected by the pRSV-CAT DOTMA-cholesterol:liposome aerosol. The results also show that neither aerosol administration of the pRSV-CAT alone, nor a lower aerosol dose of pRSV-CAT: DOTMA-cholesterol complexes produce detectable expression of the CAT gene in mouse lungs. Thus, both the cationic liposome carrier, and a sufficient dose of DOTMA: liposome complexes are required to produce transgene expression in the lung after aerosol administration, maximum transgene expression is achieved by complexing the liposomes and DNA together at an :DOPE liposomes (A,B,C,D), or from untreated mice (E,F). The section shown in d was treated with normal rabbit serum in place of anti-CAT antibody. Magnification: A,D (×50); B,C,E (×250).

As can be seen in FIG. 20, animals administered 2.0 mg RSV-CAT with 4.0 μmol DOTMA/cholesterol (2:1) expressed the CAT protein while the control animals, as well as animals receiving RSV-CAT DNA abre and animals receiving a lower dose of RSV-CAT-DOTMA:chol complexes did not. A similar procedure was followed with respect to pRSV-β-gal, with the exception that 50 mg of pRSV-β-gal was mixed with 50 μmoles of DOTMA/cholesterol (2:1). The presence of β-gal activity was determined using a standard histochemical staining procedure. β-gal activity was present in the airway epithelial cells of exposed rats.

Also tested was a plasmid containing the CAT gene driven by the CMV promoter. This plasmid was made as described in Huang, M. T. F. and Gorman, C. M. *Nuc. Acids Res.* (1990) 18:937–947, with the exception that a CMV promoter and a hybrid intron sequence were used rather than the SV40 promoter in the plasmid pML.I.CAT, described therein. Briefly, the CAT lipid carrier was constructed by first making a pML-based plasmid containing the CMV promoter immediately followed by a portion of the 5'-untranslated leader from the adenovirus-major late (AML) region. This region contained all but the first 13 nucleotides of the first exon of the tripartite leader plus a portion of an intervening sequence (IVS) from the AML region. A synthetic oligonucleotide was inserted which merged with the adenovirus intron to provide a functional splice acceptor sequence derived from an IgG variable region. Bothwell, et al, *Cell* (1981) 24:625–637. This plasmid was then cut at two restriction sites bordering the intron (ClaI and PstI) to remove a 292 bp fragment. A matching synthetic oligonucleotide linker was inserted. The plasmid was termed pCIS-CAT.

Figure 21:
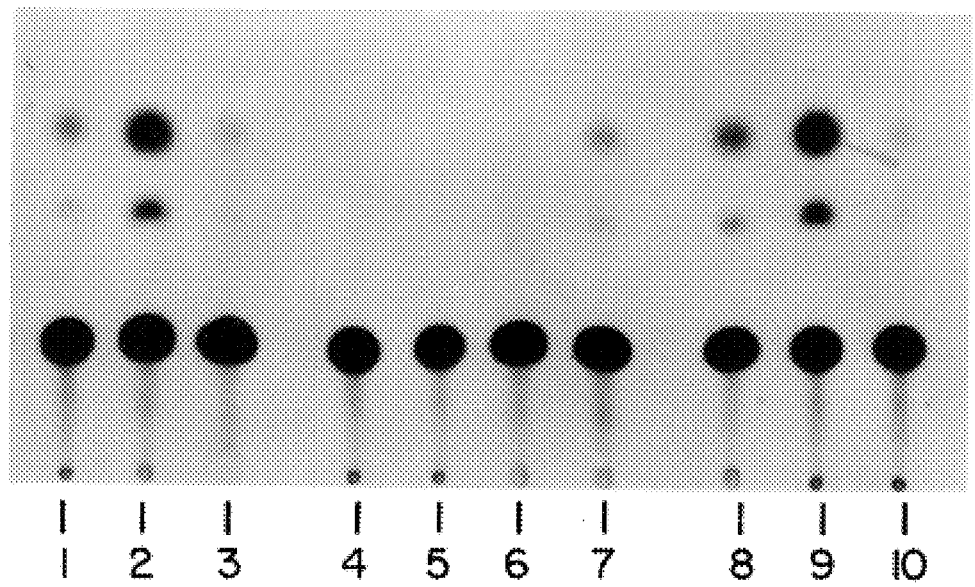
Figures 22A, 22B:
Figure 22C:
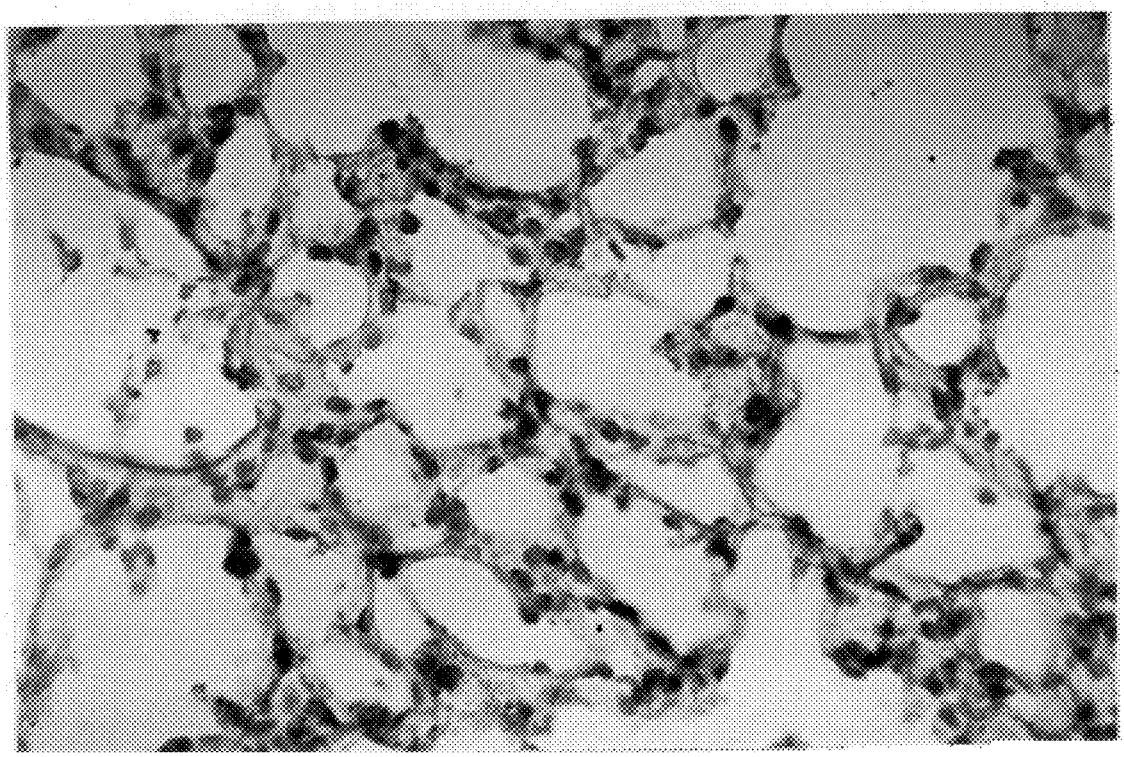
Figures 22D, 22E:
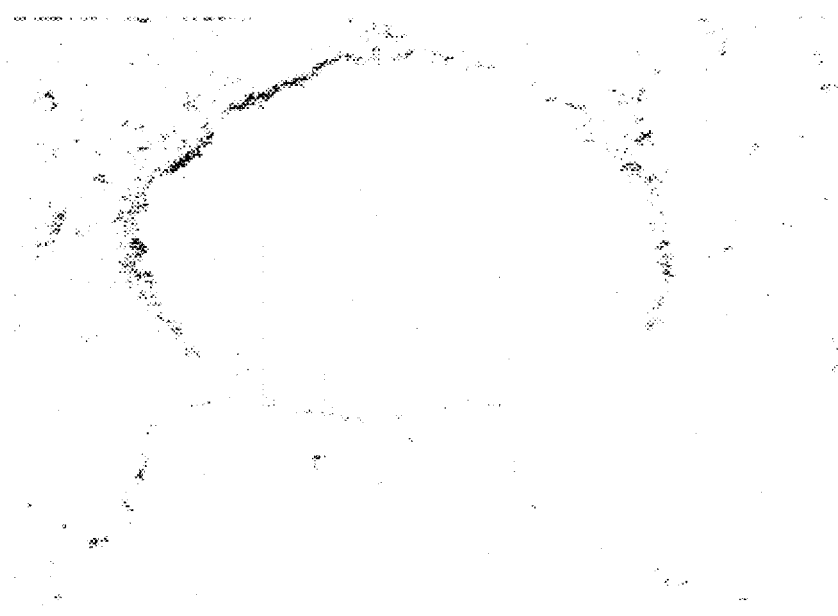
Figure 22F:
Figure 23:
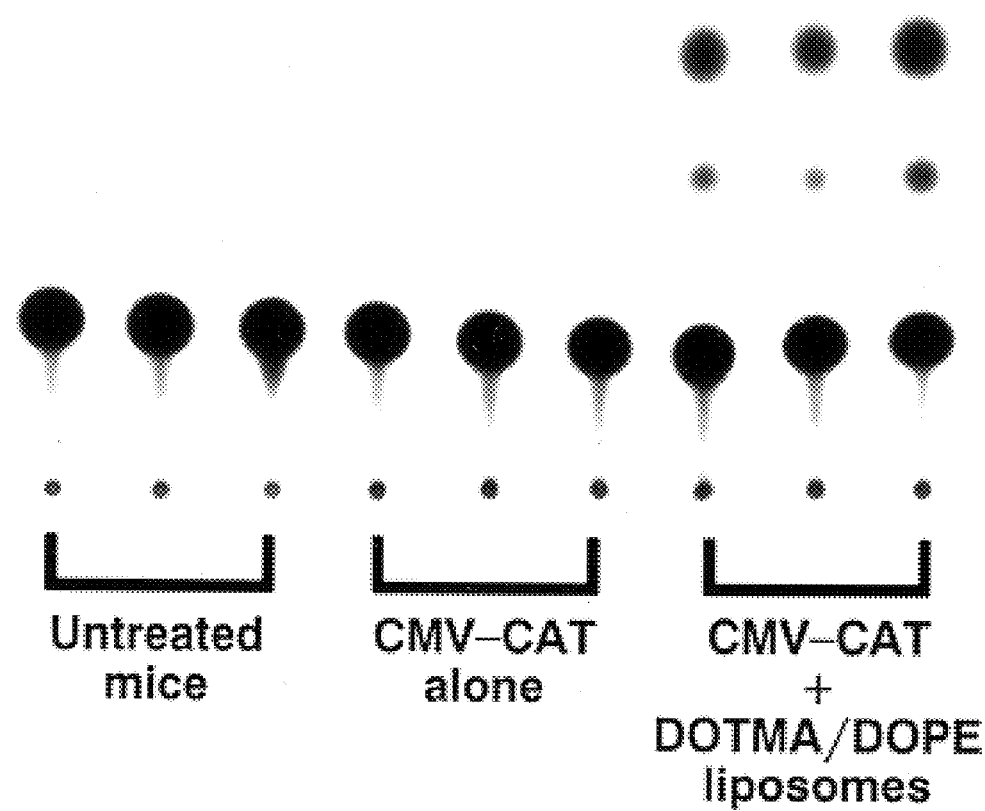
FIG. 23 shows CAT activity in lung extracts from mice sacrificed 72 hours after receiving an aerosol containing either 12 mg of CMV-CAT plasmid alone or 12 mg of CMV-CAT plasmid complex to 24 μmols of DOTMA-:DOPE (1:1) liposomes. Untreated mice were also assayed.

To test for expression of the CAT gene using pCIS-CAT, 12 mg pCIS-CAT was mixed with 24 μmoles of DOTMA/DOPE (1:1). Female ICR mice were placed in three different aerosol receiving chambers. All mice received the same amount of the CAT expression plasmid complexed to liposomes, as described above. Animals 1–3 were exposed to the aerosol in an Intox designed aerosol chamber. Animals 4–7 were exposed to the aerosol in a modified rat cage containing dividers for individual mice. Animals 8–10 were placed in a smaller, similarly modified mouse cage after being put in the restrainers used in the Intox chamber. 48 hours following aerosolization, the animals were sacrificed and whole lungs assayed for CAT expression using the chromatographic CAT assay. As can be seen in FIG. 21, a single aerosol dose of a CAT gene-expression plasmid complexed to cationic liposomes can produce high-level transgene expression in the lungs of mice. Significant levels of transgene expression are present in the lungs of all 7 mice (numbers 1–3 and 8–10) which were exposed to the aerosol mist in Intox nose-only exposure tubes which were constructed to maximize the amount of aerosol that the mice inhaled. The amount of variation seen here comparable to that seen in other aerosol experiments and may have several explanations, including variations in exposure to the aerosol mist, individual variations in efficiency of nasal filtration, etc.

Example 2
Preparation of Lipid carriers and DNA Complexing with Lipid carriers Lipid carriers containing a cationic lipid, such as {N(1-2-3-dioleyloxy) propyl}-N,N,N-triethylammonium} (DOTMA), dimethyl dioctadecyl ammonium bromide (DDAB), or 1,2-dioleoyloxy-3-(trimethylammonio)propane (DOTAP) or lysinyl-phosphatidylethanolammine and a second lipid, such as dioylphosphatidylethanolamine (DOPE) or cholesterol, were prepared as follows.

Preparation of lipid carriers

Lipids, e.g. DDAB, L-lysinyl-phosphatidylethanolammine (L-PE), E-PC, E-DMPC, cholesterol-ester-β-alanine (CEBA), DOTAP, and cholesterol (Chol) were dissolved in chloroform. Proper amounts of each lipid (determined by the desired molar ratio of each lipid in the final lipid carrier formulation usually 1 to 1 moles cationic lipid to moles non-cationic lipid but ranging from 5 to 1 to 1 to 5) were mixed together and evaporated to dryness on a rotary evaporator. The lipid film was then resuspended by vortexing after the addition of 5% dextrose in water or lipid carrier buffer (25 mM Tris-HCl pH7.4, 100 $\mu$M $ZnCl_2$ isotonic solution) to make a final lipid concentration of 20 mM of multi-lamellar vesicles (MLV). For the preparation of small unilamellar vesicles (SUV), the mixture was then sonicated in a bath sonicator for 15 min, and the lipid carriers were stored under argon at 4° C. until use.

Plasmid Preparation

The *E. coli* strain which carries the plasmid was grown in TB at 37° C. The method of plasmid purification is a modification of the protocol of "lysis by alkali" and "purification of plasmid DNA by precipitation with polyethylene glycol" described by Sambrook, el al. (*Molecular Cloning*, 2nd edition, 1989, Cold Spring Harbor Laboratory Press). The modification is that the precipitation of DNA by PEG is omitted. The final DNA preparation is dissolved in 10 mM Tris-HCl pH8.0.

Preparation of lipid carrier-plasmid complexes

Plasmids were diluted separately in 5% dextrose in water solution to the desired concentration (usually 1 $\mu$g/$\mu$g). The lipid carriers were also diluted in 5% dextrose in water to the same volume as the plasmid.

The amounts of lipid carriers used were determined based on the ratio of moles of liposomal lipid to $\mu$g of plasmid added, e.g. for lipid carrier:plasmid=1:1, one nanomole of cationic lipid is mixed with 1 $\mu$g of plasmid DNA. Plasmid and lipid carriers were then mixed together to form DNA:lipid carrier complexes.

Dose injected

At least 50 $\mu$g, and routinely 100 $\mu$g of plasmid DNA complexed to cationic lipid carriers is injected per mouse. For injection of plasmid alone, at a 500 $\mu$g and routinely 2 mg of plasmid DNA is injected by tail vein per mouse.

Example 3
Demonstration by Immunohistochemistry of CAT Gene Expression in the Lung After Intravenous (iv) injection of pZN27-DDAB: Cholesterol Lipid carrier Complexes Lipid Carrier
  DDAB:Chol=1:1, stock 20 mM in lipid carrier buffer.
Plasmid
  pZN27.
DNA:Lipid carrier Ratio
  Lipid carrier:plasmid=5 nanomoles cationic lipid:1 $\mu$g DNA
DNA dose
  100 $\mu$g plasmid DNA in 200 $\mu$l 5% dextrose in water was injected iv by tail vein per mouse.

Mice
  ICR, female, 25 grams.
Immunohistochemical staining to detect CAT protein in lung sections of mice in vivo
Procedure Forty eight hours after injection of the pZN27-DDAB:Chol complexes, the lungs are removed, perfused with 33% O.C.T., embedded in O.C.T. and snap frozen. Frozen tissue are sectioned at 6 microns, collected onto glass slides, fixed for 10 minutes in 4° C. acetone and then placed in 0.2% Triton X-100 to permeabilize membranes. Sections are then incubated for 12–48 hours math the monoclonal anti-CAT antibody (available from Dr. Parker Antin, Univ. of Arizona) or isotype negative control antibody at the appropriate dilution. After washing, 1) a biotinylated antibody directed against the primary antibody (Zymed, S. San Francisco) is added for a minimum of 60 minutes, 2) followed by application of the streptavidin-alkaline phosphatase complex (Zymed) for 60 minutes and 3) application of the substrate-chromogen appropriate for the enzyme label per manufacturers instructions. Slides are then coverslipped in water-soluble mounting media for examination.

Results

Figure 2A:
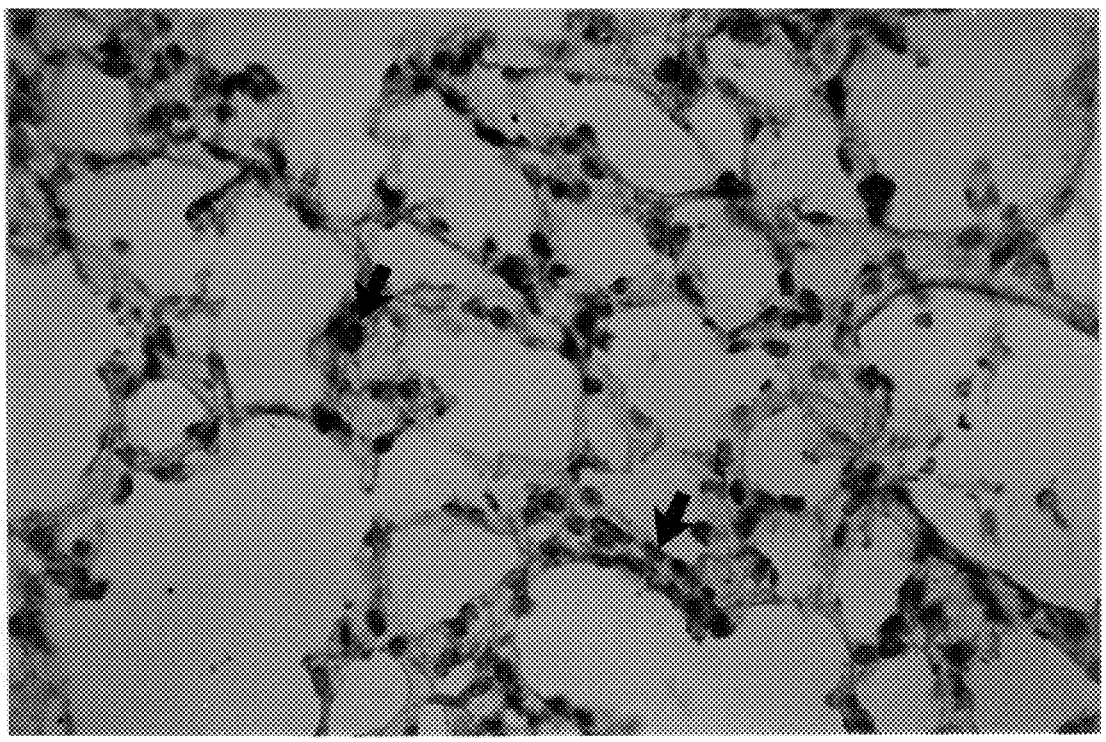
FIGS. 2(A–B). A shows a section of mouse lung 48 hours following iv injection of PZN27:DDAB:Chol expression vector-cationic lipid carrier complexes. Lipid carrier composition was 1:1 molar DDAB:Chol. Lipid carrier plasmid ratio was 5 nanomoles cationic lipid to 1 µg DNA. A dose of 100 µg DNA was injected per mouse. This field shows alveoli and alveolar lining cells, the majority (50–70%) of which stain positively for the presence of CAT protein when probed with anti-CAT antibody and visualized using alkaline phosphatase. The treated animals' lungs stain uniformly with diffuse involvement of alveolar and vascular endothelial cells. Airway epithelial staining is also seen indicating airway are also transfected. The CAT (chloramphenicol acetyl transferase) protein normally is not present in mammalian cells and therefore the presence of CAT protein in these cells indicates that they have been transfected in vivo.
FIG. 2B shows a section of mouse lung from a control animal treated with iv-injected lipid carrier only, and probed with anti-CAT antibody. Cells do not show significant staining, although low-level background staining is detectable in some alveolar macrophages, which possess endogenous alkaline phosphatase activity.
Figure 2B:
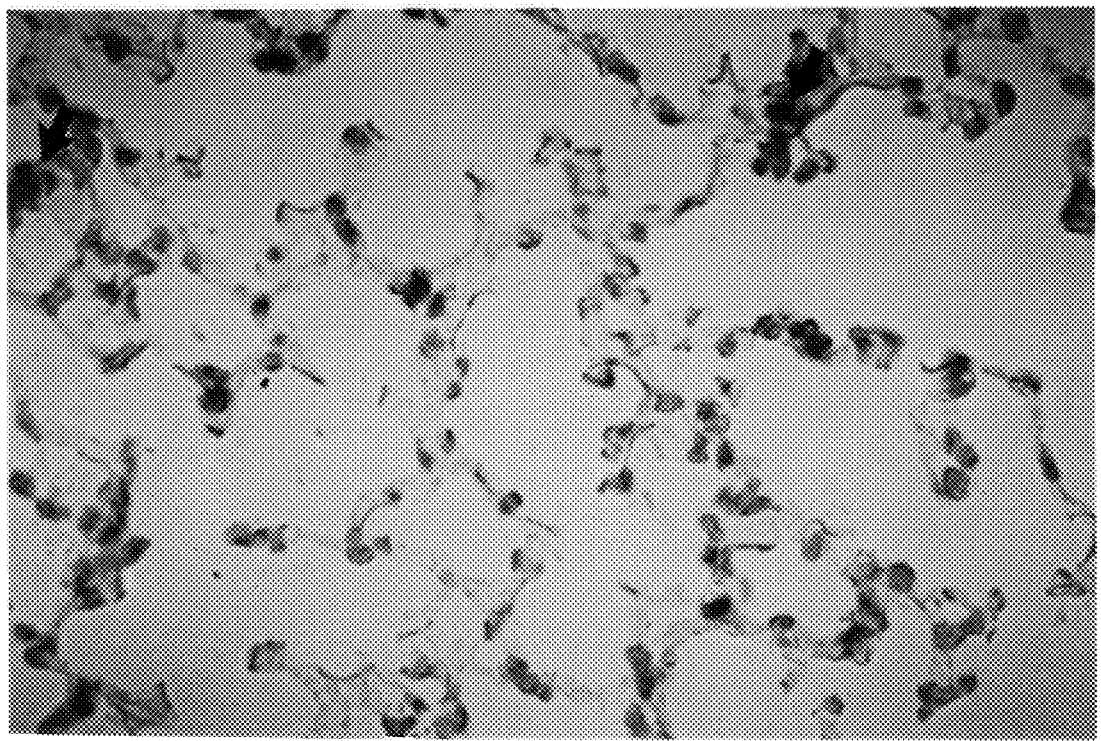
Figure 3A:
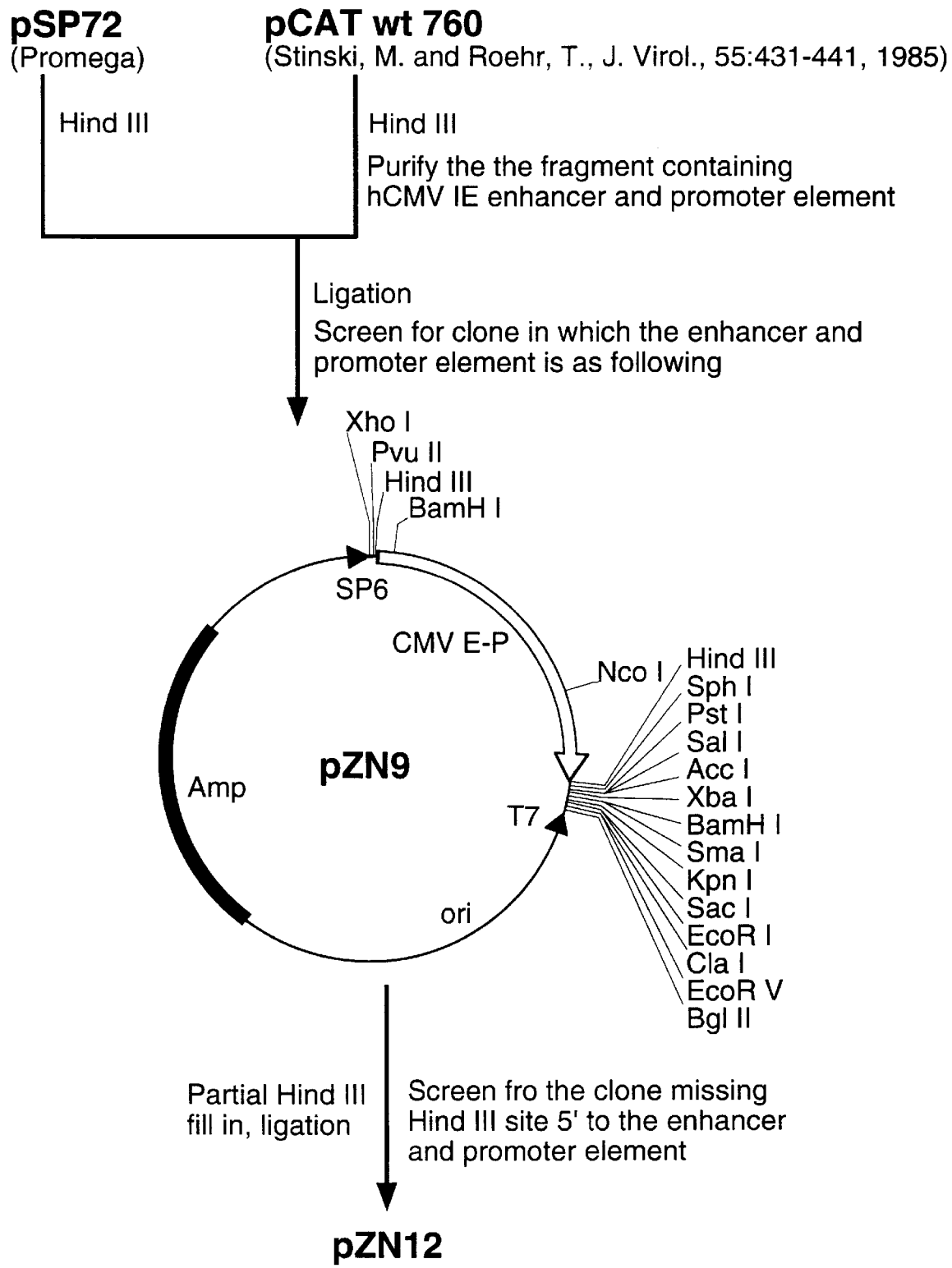
FIG. 3 shows construction of pZN20.
Figure 3B:
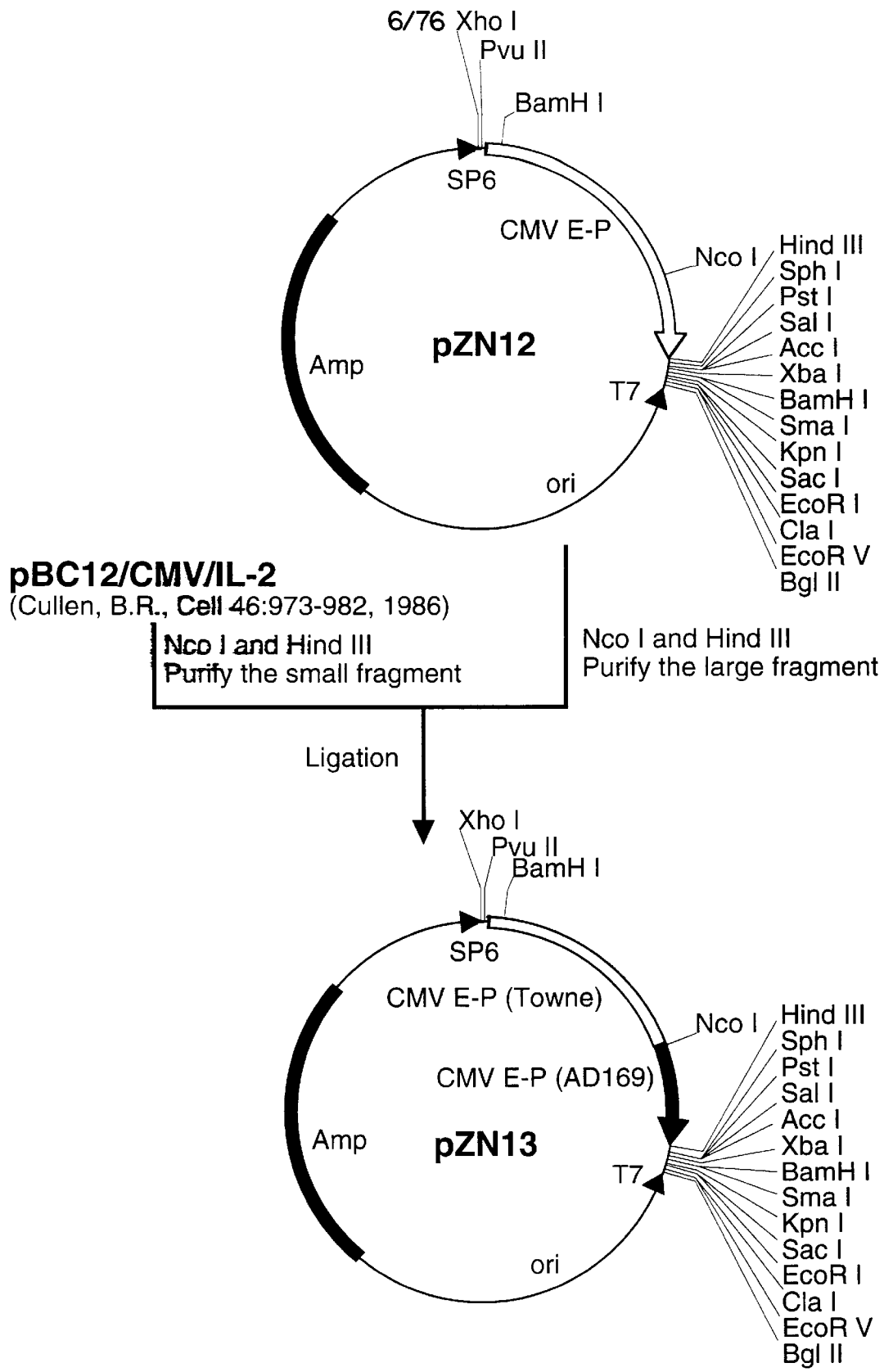
Figure 3C:
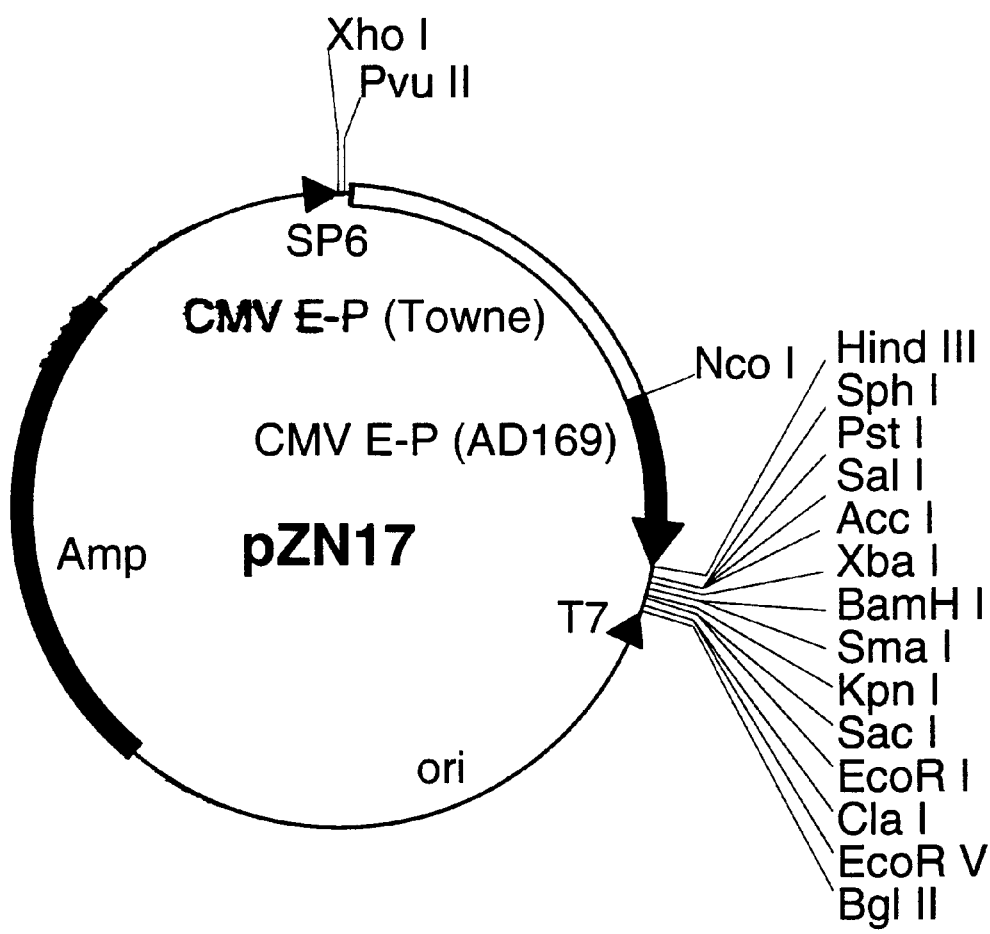
Figure 3D:
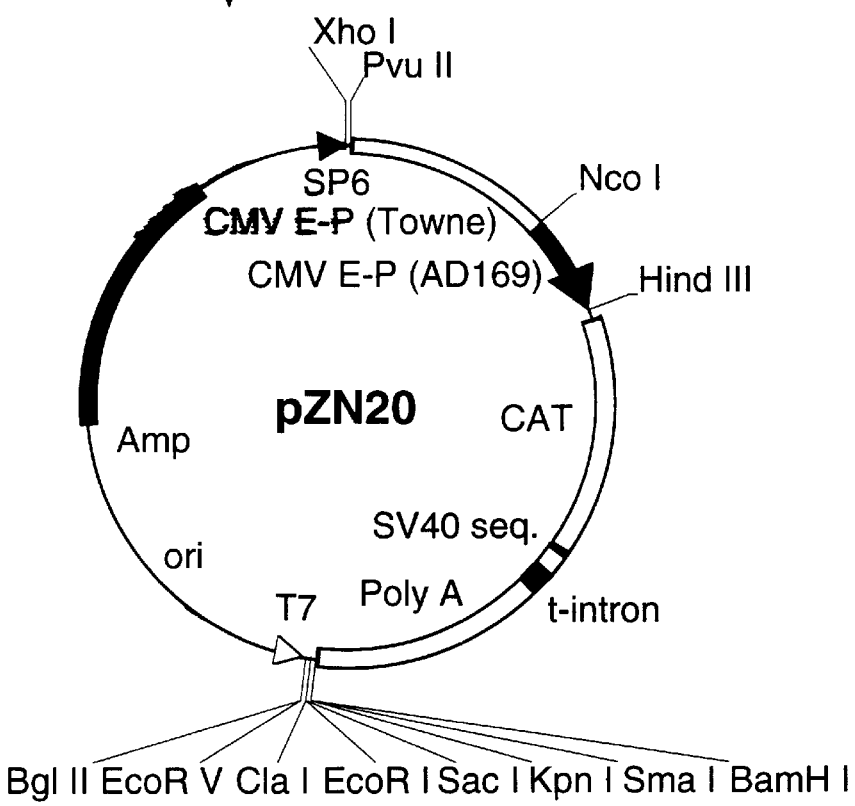

The results are shown in FIGS. 2A, 2B and demonstrate diffuse staining of the lung. The stain localizes to the alveolar walls, indication that greater than 70% of pulmonary vascular endothelial cells, as well as alveolar lining cells, including type I and type II cells and alveolar macrophages ages are transfected by a single iv injection of DNA lipid carrier complexes. In addition, significant numbers of bronchiolar airway lining cells stain positively for CAT protein, and are therefore transfected in vivo by iv injection of lipid carrier:DNA complexes. Thus, the great majority of all cells in the lung transfected by a iv injection of pZN27-DDAB:CHOL complexes.

Example 4
Expression of pZN20 Following Intraperitoneal Administration

Effect of the Amount of pZN-20cationic lipid carrier complexes injected ip on the level of CAT gene expression in vivo Female ICR mice (Simonson Labs, Gilroy, Calif.) were injected ip with 1 ml of 5% dextrose in water containing 0.01, 0.1 or 1 mg of pZN20 expression plasmid complexed to 0.01, 0.1 or 1 $\mu$moles, respectively of DDAB:DOPE lipid carriers. Mice were sacrificed 48 hours later, the organs removed, and tissues were homogenized in 0.25M Tris-HCL buffer pH 7.8, using a hand-held homogenizer. Cytoplasmic extracts were made, normalized by protein content and level of CAT protein was then measured. The experiments comprise three animals per group and the results show the mean dpm±SEM of acetylated chloramphenicol.

Methods

Lipid carriers containing DDAB were prepared in 1:1 molar ratio with DOPE, as follows: 10 $\mu$mole of DOPE dissolved in chloroform and 10 $\mu$moles of the cationic lipid, dissolved in ethanol were evaporated to dryness on a rotary evaporator. One ml sterile of water was added, and the mixture was sonicated in a bath sonicator (Laboratory Supply, Hicksville, N.Y.) for 20 min. Lipid carriers had mean diameters of approximately 100±25 nm. For CAT assay, cell extracts were made, and their protein content determined by the Coomassie blue assay (BioRad, Richmond, Calif.). One hundred $\mu$g of protein from the lung, spleen, liver, and heart extracts, and 50 $\mu$g of lymph node extract were reacted with $^{14}$C labeled chloramphenicol and chromatographed as previously described (Gorman, supra).

To calculate dpm, both the acetylated and unacetylated species were cut from TLC plates and radioactivity counted in a scintillation counter. The ratio between acetylated and unacetylated counts was used to calculate the mean dpm. The mean dpm from tissues of untreated control animals were subtracted from each treated animal for each tissue.
Results To assess potential dose-response relationships in vivo, animals were injected animals in groups of three with 0.01 mg, 0.1 mg, or 1 mg of pZN20 plasmid complexed to 0.01 µmole, 0.1 µmole, or 1 µmole respectively of DDAB:DOPE lipid carriers. Both the 0.1 mg and 1 mg DNA doses produced highly significant levels of CAT protein (p<0.005) in all the organs assayed. Maximal levels of CAT gene expression in each organ were produced by the 1 mg DNA dose: increasing the DNA-lipid carrier dose 10 fold resulted in an approximately 2 fold increase in lymph node CAT levels and a 3 fold increase in the spleen. Intraperitoneal injection of 1 mg of the pZN20 plasmid alone did not produce detectable CAT protein above background levels.

Example 5

Demonstration of CAT gene expression in the spleen after intravenous (iv) injection of p5'PRL3CAT:L-PE;CEBA complexes Lipid carrier L-PE: CEBA=1:1, stock 20 mM in lipid carrier buffer.

Plasmid p5'PRL3CAT.

DNA:Lipid carrier Ration

Lipid carrier:plasmid=1 nanomole cationic lipid: 1 µg plasmid DNA.

DNA dose

200 µg plasmid DNA in 200 µl 5% dextrose in water was injected by tail vein per mouse.

Mice

BalB/c, female, 25 grams.

Tissue extraction procedure

Forty eight hours after tail vein injection, mice were sacrificed, whole spleen was homogenized in 1 ml of 0.25M TRis-HCl pH 7.8, 5 mM EDTA, 80 µg/ml PMSF and the resulting extract was centrifuged and then the supernatant was subjected to 3 cycles of freeze-thaw and then heated to 65° C. for 20 min.

CAT assay procedure

100 µl of extract+10 µl of 20 mM acetyl CoA+4 µl of $^{14}$C-chloramphenicol (25 µCi/ml, 55 mCi/mmole, Amersham) were incubated together at 37° C. for 6 hr. At 3 hours, an additional 10 µl of acetyl CoA was added.

Results

The results are lane 2 (lipid carriers only) and lane 5 (lipid carrier-DNA complex), and indicate that a significant level of CAT activity is present in the spleen extract of the treated animal, but not in the extract of control spleen, taken from an animal injected with lipid carrier alone.

Demonstration of CAT gene expression in the lung after intravenous (iv) injection of pRSV-CAT:L-PE:CEBA complexes Lipid carrier L-PE:CEBA=1:1, stock 20 mM in lipid carrier buffer.

Plasmid pRSV-CAT.

DNA:Lipid carrier Ratio

Lipid carrier:plasmid=1 nanomole cationic lipid: 1 µg plasmid DNA.

DNA dose

100 µg plasmid DNA in 200 µl 5% dextrose in water was injected by tail vein per mouse.

Mice

BalB/c, female, 25 grams.

Tissue extraction procedure

Forty eight hours after tail vein injection, the animals were sacrificed, whole lung was homogenized in 1 ml of 0.25M Tris-HCl pH 7.8, 5 mM EDTA, 80 µg/ml PMSF and the resulting extract was centrifuged and then the supernatant was subjected to 3 cycles of freeze-thaw and then heated to 65° C. for 20 min.

CAT assay procedure

100 µl of extract+10 µl of 20 mM acetyl CoA+4 µl of $^{14}$C-chloramphenicol (25 1µCi/ml, 55 mCi/mmole, Amersham) were incubated together at 37° C. for 6 hr. At 3 hours, an additional 10 µl of acetyl CoA was added.

Results

Figure 9:
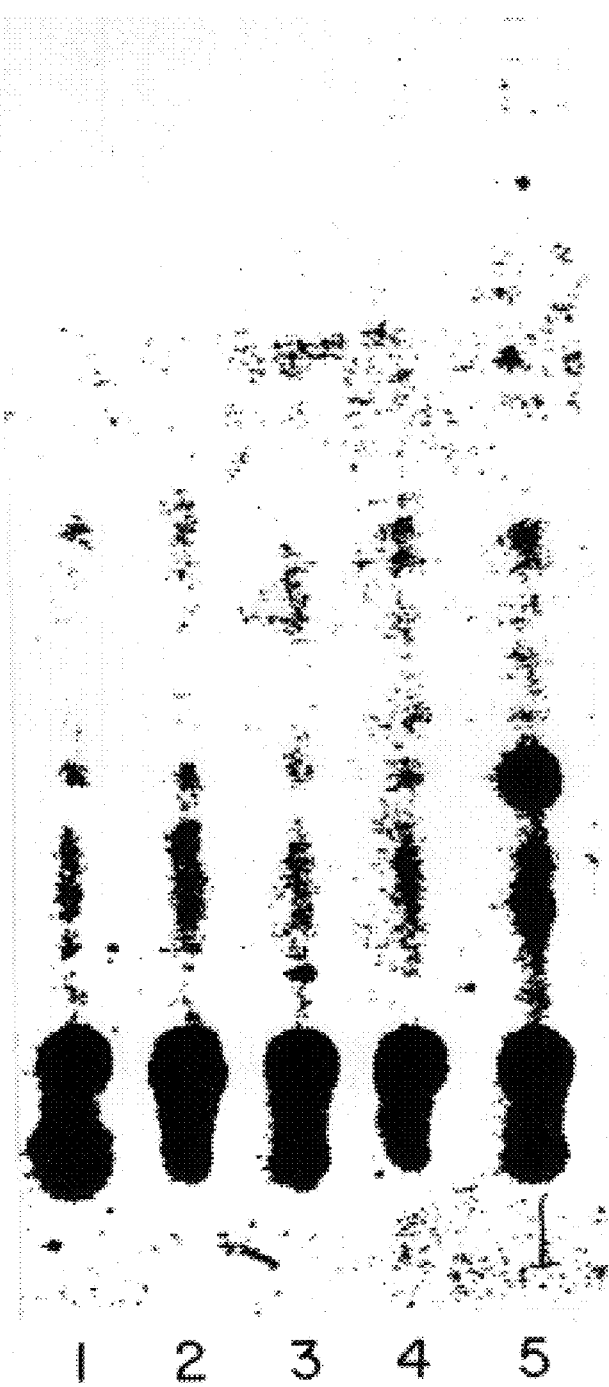

The results are shown in FIG. 9, and indicate that a significant level of CAT activity (indicative of expression of the transgene) was present in the lung of the animal injected with lipid carrier:DNA complexes (lane 5), but not present in the lungs from control animals (lanes 1–4).

Demonstration of CAT gene expression in multiple tissues after intravenous (iv) injection of pZN20:DDAB:DOPE complexes Lipid carrier DDAB:DOPE=1:1, stock 10 mM in 5% dextrose.

Plasmid pZN20.

DNA:Lipid carrier Ratio

Lipid carrier:plasmid=(A) 3 nanomole cationic lipid:1 µg plasmid DNA (SUV);(B) 6 nanomole cationic lipid:1 µg plasmid DNA (MLV).

DNA dose

100 µg plasmid DNA in 200 µl 5% dextrose in water was injected by tail vein per mouse. Three mice each received this dose of MLV:pZN20 and 3 mice each this dose of SUV:pZN20.

Tissue extraction procedure

Each organ was homogenized in 0.3 ml of 0.25 M Tris-HCl pH 7.8, 5 mM EDTA, and the resulting extract was centrifuged and then the supernatant was subjected to 3 cycles of freeze-thaw and then heated to 65° C. for 20 min.

CAT assay procedure

The protein concentration of each tissue extract was quantitated using a Coomassie blue-based protein assay (Bio-Rad, Richmond, Calif.,) and the same amount of total protein from each tissue extract was added in the CAT assay, together with 10 µl of 20 mM acetyl CoA+12 µl of $^{14}$C-chloramphenicol (25 µCi/ml, 55 mCi/mmole, Amersham), at 37° C. for 13 hrs.

Results

Figure 5A:
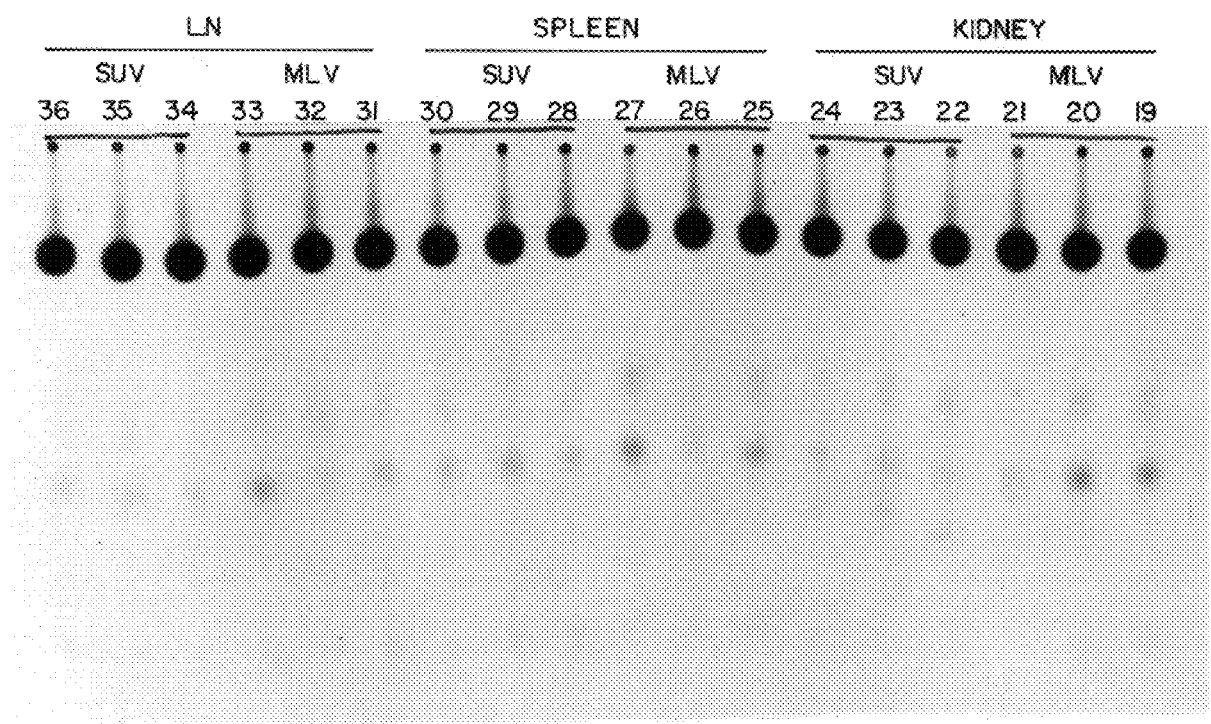
FIG. 5 shows CAT gene expression in the indicated tissues following intravenous injection of pZN20:DDAB:DOPE complexes. Lipid carriers were DDAB:DOPE 1 to 1 molar. Two lipid carrier-to-plasmid ratios (nanomoles cationic lipid µg plasmid DNA) were used, MLV, 6:1 and SUV, 3:1. Lanes 1–6 are samples from lung tissue; lanes 7–12, heart tissue; lanes 13–18, liver; lanes 19–24, kidney; lanes 25–30, spleen; lanes 31–36, lymph nodes. The first 3 sample of each tissue set were from animals injected with MLV, the next 3 samples of each tissue set were from animals injected with SUV. In lanes 1–18 the chromatograph runs from bottom to top, in lanes 19–36 the chromatograph runs from top to bottom. These results demonstrate that iv injection of pZN20:DDAB:DOPE complexes produces significant levels of CAT gene expression in six different tissues. Furthermore, MLV appear to mediate equal or greater levels of in vivo gene expression than do SUV composed of the same lipids.
Figure 5B:
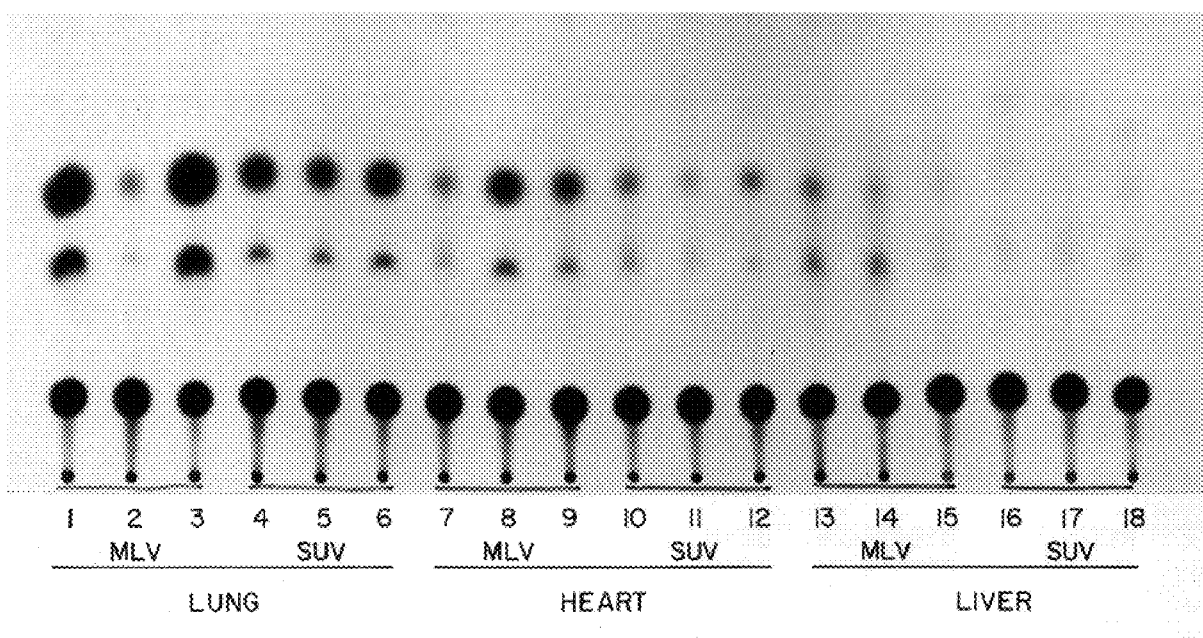
Figure 9A:
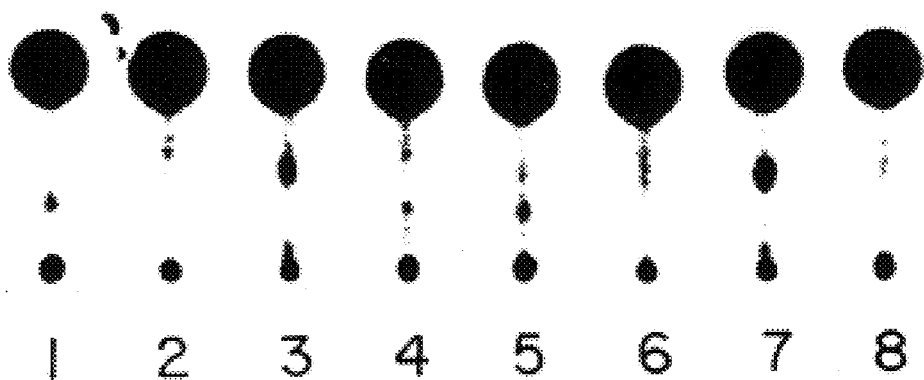
FIG. 9 shows CAT expression in the lung after intravenous injection of pRSV-CAT:L-PE:CEBA complexes. Lanes 1–3 are samples from untreated mouse lung, lane 4 is from a lung sample from a mouse treated with lipid carriers only, lane 5 is a sample from a mouse treated with the lipid carrier-DNA complex. Lipid carriers were 1 to 1 molar L-PE:CEBA. Lipid carrier-DNA complexes were 1 nanomole cationic lipid to 1 µg DNA. 100 µg DNA was injected per mouse. Chromatograph runs from bottom to top of Figure as shown.

The results are shown in FIG. 5, and demonstrate that iv injection of pZN20:DDAB:DOPE complexes significant levels of CAT gene expression in each of 6 different tissues including lung, heart liver, spleen, kidney and lymph nodes. Furthermore, MLV lipid carriers mediate equal or higher levels of in vivo transgene expression than do SUV lipid carriers composed of the same lipids.

Demonstration of CAT gene expression in vivo after intravenous (iv) injection of pZN20 alone Plasmid pZN20.

DNA:Lipid carrier Ratio

Plasmid DNA alone, without lipid carriers, was injected.

DNA dose

300 µg plasmid DNA in 200 µl 5% dextrose in water was injected by tail vein per mouse.

Mice
  ICR, female, 25 grams.
Tissue extraction procedure
  Each organ was homogenized in 0.3 ml of 0.25 M Tris-HCl pH 7.8, 5 mM EDTA, and the resulting extract was centrifuged and then subjected to 3 cycles of freeze-thaw and then heated to 65° C. for 20 min.
CAT assay procedure
  The protein concentration of each tissue extract was quantitated using a ninhydrin-based protein assay (Bio-Rad, Richmond, Calif.), and same amount of total protein from each tissue extract was added in the CAT assay, together with 10 µl of 20 mM acetyl CoA+12 µl of $^{14}$C-chloramphenicol (25 µCi/ml, 55 mCi/mmole, Amersham) at 37° C. for 13 hrs.

Figure 6:
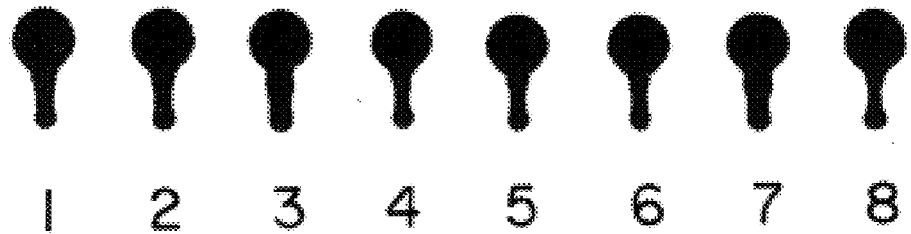
FIGS. 6(A–B) shows the results of iv injection of DOTMA:DOPE complexed to pSIS-CAT plasmid does not produce detectable CAT expression in vivo.

Example 6
Injection of DOTMA:DOPE+pSIS-CAT Plasmid Clearly Did Not Produce Detectable CAT Gene Expression in vivo)
Lipid carrier
  DOTMA:DOPE=1:1, in 5% dextrose in water
Plasmid
  pSIS-CAT (Huang, M. T. F. and C. M. Gorman, 1990, *Nucleic Acids Research* 18:937–947).
Ratio
  Cationic lipid:plasmid=4 nmoles: 1 µg, dose: 100 µg DNA in 200 µl 5% dextrose in water.
Mouse
  ICR, female, 25 grams.
Injection
  Tail vein.
Tissue collection and processing
  Mice we sacrificed at day 2 and day 6, and lung, spleen, liver, and heart were collected. The whole organs were homogenized in 0.5 ml, except livers which were homogenized in 2.0 ml, of 0.25M Tris-HCl pH 7.8, 5 mM EDTA, 2 µg/ml aprotinin, 1 µg/ml E64, and 0.5 µg/ml leupeptin (all protease inhibitors were purchased from Boehringer Mannheim). Extracts were subjected to three cycles of freeze-thaw, then heated to 65° C. for 10 min.
CAT assay
  100 µl of extracts for each assay with 0.3 µCi of $^{14}$C-chloramphenicol and 10 µl of 20 mM acetyl CoA at 37° C. for either 5 hrs, or 24.5 hrs, and the materials were then extracted using ethyl acetate and analyzed on TLC plates.
Result
  There were no acetylated chloramphenicol species presented as determined by comparing the extracts from treated animals with that from control animals.
  Thus, under similar experimental conditions that produce high level expression of pZN27, the use of the pSIS-CAT expression vector does not result in any detectable expression of the linked-CAT gene in any of the tissues assayed in vivo. The lack of expression of pSIS-CAT in vivo may be due either to a different promoter-enhancer element (SV40) or to a different intron sequence when compared to the pZN27 vector, which yields high level in vivo expression.
  The results are shown in FIG. 6.

Example 7
Interaction Of DNA: Lipid carrier Complexes With Cell Surface Receptors
Cells and cell culture
  CV-1 (African green monkey kidney), U937 (human myelocytic leukemia), murine erythroleukemia (MEL) cells, and K562 cells (human erythroleukemia cells were obtained from the American Type Culture Collection (Rockville, Md.). CV-1 and MEL cells were maintained in Dulbecco minimum essential medium (DME)- H-21 with 5% fetal bovine (FBS) at 37° C. and 7% $CO_2$. Rat alveolar type II cells and rat alveolar macrophages were isolated and purified as previously described. (Debs et al. *Amer. Rev. Respiratory Disease* (1987) 135:731–737; Dobbs, L. *Amer. Rev. Respiratory Disease* (1986) 134:141–145) Type II cells were maintained in DME-H-16 with 5% FBS at 37° C. and 7% $CO_2$. Twenty nanomoles of DOTMA:DOPE lipid carriers complexed to 20 µg of pRSV-CAT plasmid DNA were added to 2 million cells growing in 60 mm Falcon plastic dishes (either SUV or MLV), and fixed for EM at time points from 15 minutes to 2 hours thereafter.
Fixation and Processing for Electron Microscopy
  DOTMA lipid carriers and cells in tissue culture or freshly isolated from blood or pulmonary alveoli were fixed in 1.5% glutaraldehyde in 0.1 molar sodium cacodylate buffer containing 1% sucrose, pH 7.4, at room temperature for 1 hr. Following tannic acid and uranyl acetate enhancement, tissue was dehydrated in a graded series of alcohols and embedded in epoxy 812 resin (Ernest F. Fullam, Inc., Latham, N.Y.) sectioned on an MT 2 microtome using diamond knives and examined with a Jeol 100CX transmission electronmicroscope operating at 80 kv. The results are shown in FIG. 4.
  The most frequent interaction between DOTMA lipid carriers, either uni- or multiammellar lipid carriers, complexed to plasmid DNA and the various cell types (CV-1 monkey kidney cells, U937 human myelomonocytic leukemia cells, K562, MEL erythroblastic leukemia cells, rat alveolar macrophages, and alveolar type II cells), is that of lipid carrier adhesion and internalization in a typical coated vesicle pathway (FIGS. 4a–f). This interaction is common to well defined examples of receptor-mediated endocytosis. All cells which appear to have contacted cationic lipid carrier:DNA complexes ingest the complexes after binding to the plasma membrane. All these cell types demonstrate the same classical receptor-mediated endocytic pathway of internalization. Human cells are more efficiently transfected than are other cells, such as rodent cells.

Example 8
Demonstration of High Level CAT Gene Expression in Multiple Tissues After Intravenous (iv) Injection of pZN27 Alone, or pZN27:DDAB:cholesterol SUV Complexes
Lipid carrier
  DDAB:Chol=1:1, stock 10 mM in 5% dextrose. After addition of 5% dextrose to the dried lipid film, the SUV were prepared by sonication in a bath sonicator for 20 minutes.
Plasmid
  pZN27.
DNA:Lipid carrier Ratio
  Cationic lipid:plasmid DNA=5 nanomoles:1 µg DNA.
DNA dose
pZN27 alone
  Individual mice received 500 µg, 1 mg, 2 mg, or 500 µg, followed 4 hours later by a second 500 µg dose, respectively of pZN27 in 200 µl 5 dextrose in water by tail vein injection.
pZN27 complexed to lipid carrier
  100 µg plasmid DNA complexed to 500 nanomoles to DDAB:Chol SUV lipid carriers in 200 µl 5% dextrose in water was injected by tail vein per mouse.
Mice
  ICR, female, 25 grams.
Tissue extraction procedure
  Each organ was homogenized in 0.3 ml of 0.25 M Tris-HCl pH 7.8, 5 mM EDTA, and the resulting extract was centrifuged and the supernatant was then subjected to 3 cycles of freeze-thaw and then heated to 65° C. for 20 min.

CAT assay procedure

The protein concentration of each tissue extract was quantitated using a Coomassie blue-based protein assay (Bio-Rad, Richmond, Calif.), and same amount of total protein from each tissue extract was added in the CAT assay, together with 10 μl of 20 mM acetyl CoA+12 μl of $^{14}$C-chloramphenicol (25 μCi/ml, 55 mCi/mmole, Amersham)), at 37° C. for 13 hrs.

Results

Figures 1, 8A:
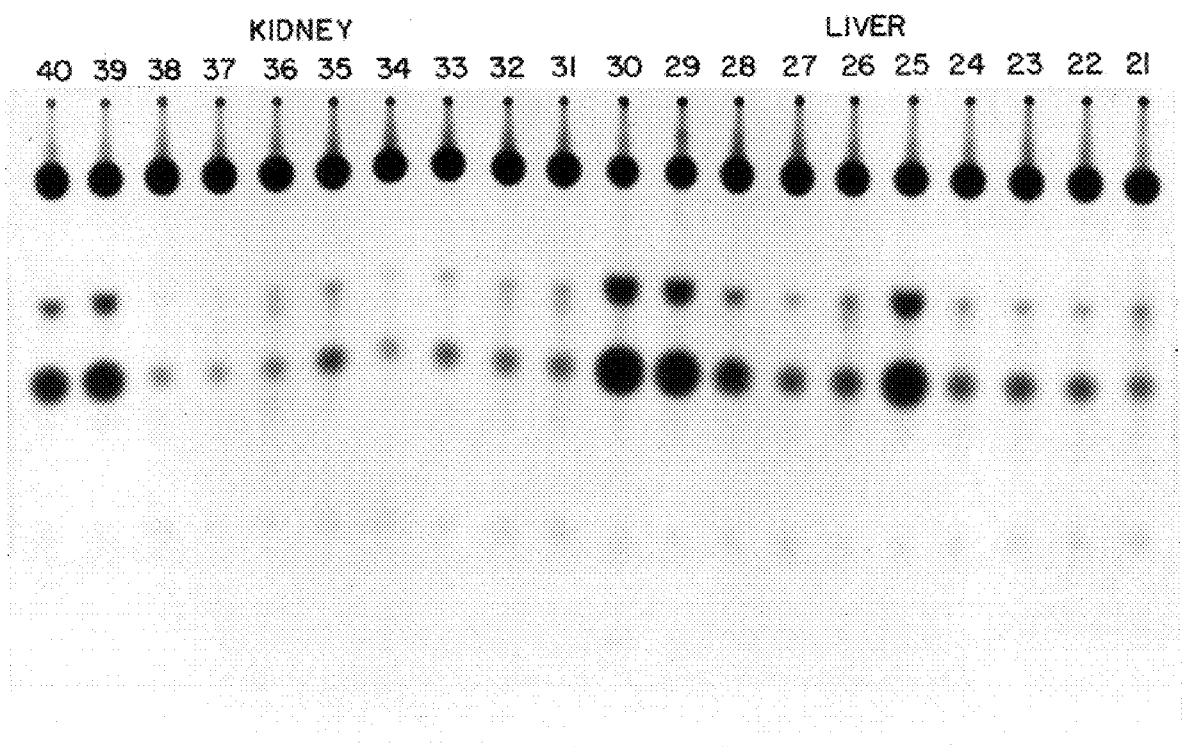
FIG. 8A lanes 1–10, lung; lanes 11–20, heart; lanes 21–30, liver; lanes 31–40, kidney.
Figures 2, 8A:
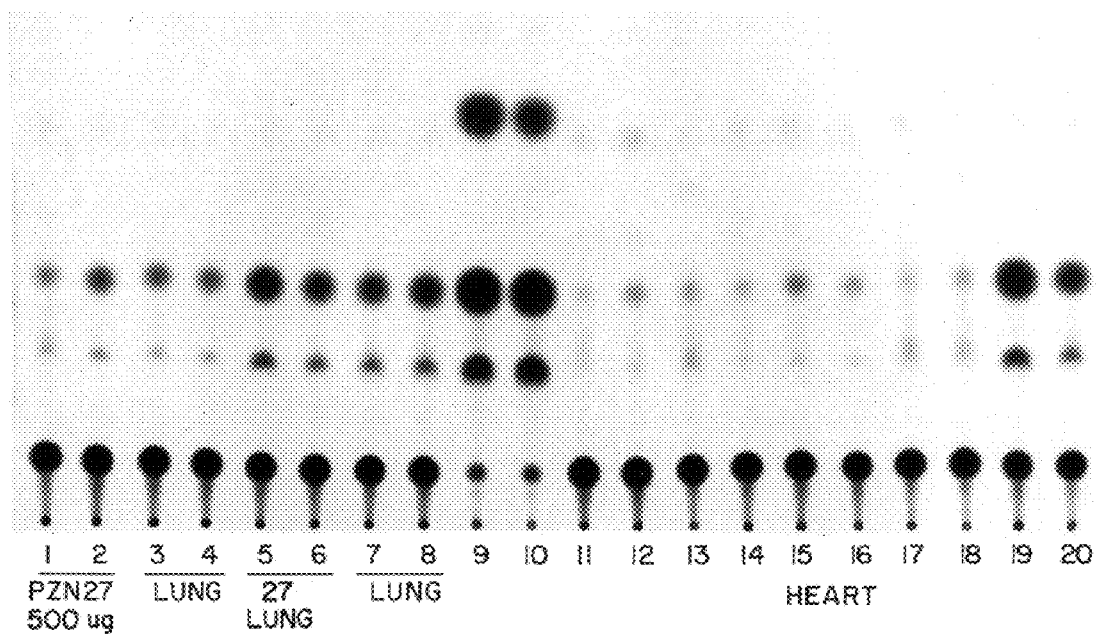
Figure 8B:
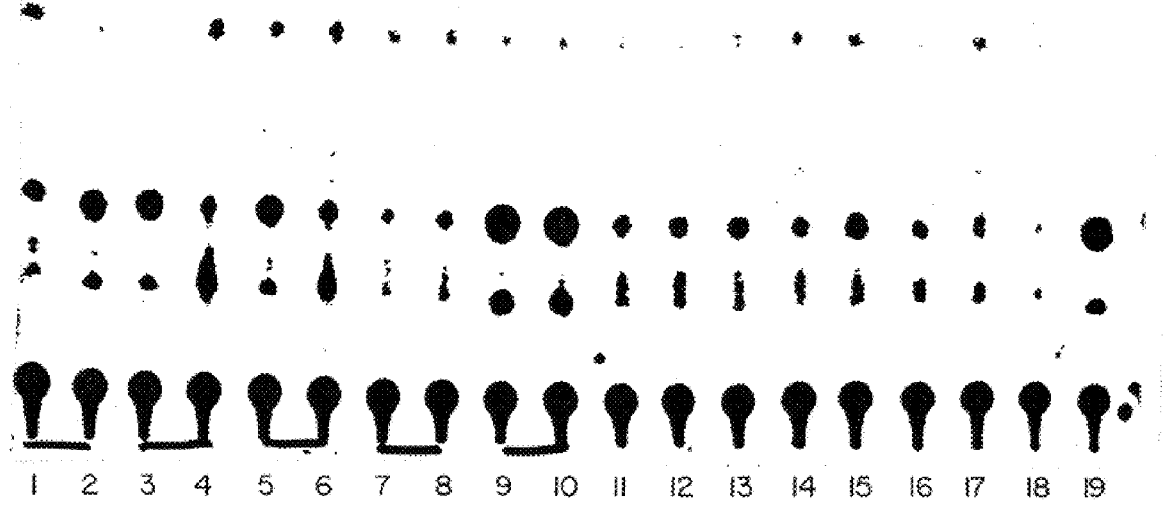
In FIG. 8B lanes 1–20 the chromatograph runs from bottom to top. Lipid carriers were 1 to 1 molar DDAB:Chol. Lipid carrier-DNA complex was 5 nanomoles cationic lipid to 1 µg DNA.

The results are shown in FIG. 8. Significant levels of CAT gene expression were seen in each of the 6 different tissues (lung, heart, liver, kidney, spleen and lymph nodes) assayed after injection of either pZN27 alone, or pZN27 complexed to DDAB:cholesterol lipid carriers. Expression of a transgene in multiple tissues in vivo after systemic injection of a naked expression plasmid has not been demonstrated previously.

Example 9
High level airway expression of the human CFTR gene in mouse lungs after aerosol administration of DDAB: cholesterol liposome-pZN32 complexes Animals Two months old, female, ICR mice obtained from Simonsen, Gilroy, Calif., were used.

Preparation of plasmid DNA

The plasmid used, pZN32, contains the human CFTR gene coding region fused to the human cytomegalovirus immediate early promoter-enhancer element shown in FIGS. 3–5 attached hereto. A full restriction map of the immediate early enhancer and promoter region of HCMV (Towne) and HCMV (AD169) is provided in FIGS. 19A and 19C. The two sequences SEQ ID NOS:2 and 3 are compared in FIG. 19B. pZN32 was purified using alkaline lysis and ammonium acetate precipitation, and the nucleic acid concentration measured by UV absorption at 260 nm.

Preparation of cationic lipid carriers

Lipid carriers were prepared as small unilamellar vesicles (approximately 100 nm in diameter) containing the cationic lipid DDAB (dimethyl dioctadecyl ammonium bromide) as DDAB:cholesterol in a 1:1 molar ratio. DDAB was purchased from Sigma, St. Louis, Mo., and cholesterol was purchased from CalBioChem, San Diego, Calif. Stock solutions of the lipids were dissolved in chloroform. Lipids were mixed in a round-bottomed flask and evaporated to dryness on a rotary evaporator under reduced pressure. Double distilled water was added to produce final lipid concentrations of 10 mM each, and the resulting mix was sonicated for approximately 20 minutes in a bath sonicator (Laboratory Supplies, Hicksville, N.Y.).

Aerosol delivery of plasmid/lipid carrier complexes to mice

Twelve mg of pZN32 complexed to 24 μmols of DDAB:cholesterol (1:1) liposomes was aerosolized over two different aerosol periods on the same day. To prevent aggregation and precipitation of the oppositely charged components, the liposomes and DNA were diluted separately in sterile water prior to mixing. Six mg of plasmid DNA and 12 μmols of DDAB:cholesterol (1:1) liposomes were each diluted to 8 ml with water and mixed. Four ml of the DNA-liposome mixture was then placed into two Acorn I nebulizers (Marquest, Englewood, Colo.), and the animals placed in an Intox small animals chamber (Albuquerque, N.M.). An air flow rate of 4 L min$^{-1}$ was used to generate the aerosol. Ninety minutes were required to aerosolize this volume (4 ml) of DNA-liposome mixture. The animals were removed from the chamber for 1–2 hours and then the above procedure was repeated with a second 4 ml dose.

Immunohistochemical staining for the human CFTR protein in mouse lungs

At selected time points following aerosolization, mice were sacrificed and their lungs immediately removed. The lung were slowly inflated with phosphate buffered saline (PBS) containing 3.3% by volume OCT (Miles, Inc.), then placed in a tissue cassette filled with OCT, and frozen in 2-methylbutane chilled in a dry ice/ethanol bath. Cryosections were cut at 5 μm and collected onto sialinized slides. CFTR protein was detected after fixation of cryosections for 10 minutes in either 4% acetone or 2% paraformaldehyde in PBS containing 0.1% Tween 20 (PBST). All subsequent dilutions and washes were done in PBST. Following fixation, sections were washed three times (5 minutes each) with PBST then covered with 10% normal rabbit serum for 10 minutes at 20° C. Immunolocalization of CFTR was then performed using an affinity purified rabbit polyclonal anti CFTR antibody, α-1468, provided by Dr. Jonathan Cohn, Duke University. The serum was replaced with α-1468, diluted (1:1000). The antibody-covered section was gently overlaid with a siliconized coverslip and incubated in a humid chamber at 4° C. for 24 hours. Slides were then warmed to 20° C. and washed three times. The presence of bound rabbit antibody against CFTR was detected by covering sections with biotinylated, affinity-purified, goat anti-rabbit antibody (Lipid carrier Laboratories), diluted 1:300 for 1 hour, followed by washing (3×10 minutes) and replacement with streptavidin labelled with alkaline phosphatase (Zymed, South San Francisco) for 20 minutes. Immobilized alkaline phosphatase was detected using AP-red (Zymed) as the chromogen; endogenous alkaline phosphatase was inhibited with levamisole (Zymed). Other controls, run concurrently, included the use of normal rabbit serum in place of primary antibody and the use of lung tissue from untreated mice. Photo-microscopy was performed using Kodak Ektachrome 64T film at x50 and x250.

Results

Figure 11B:
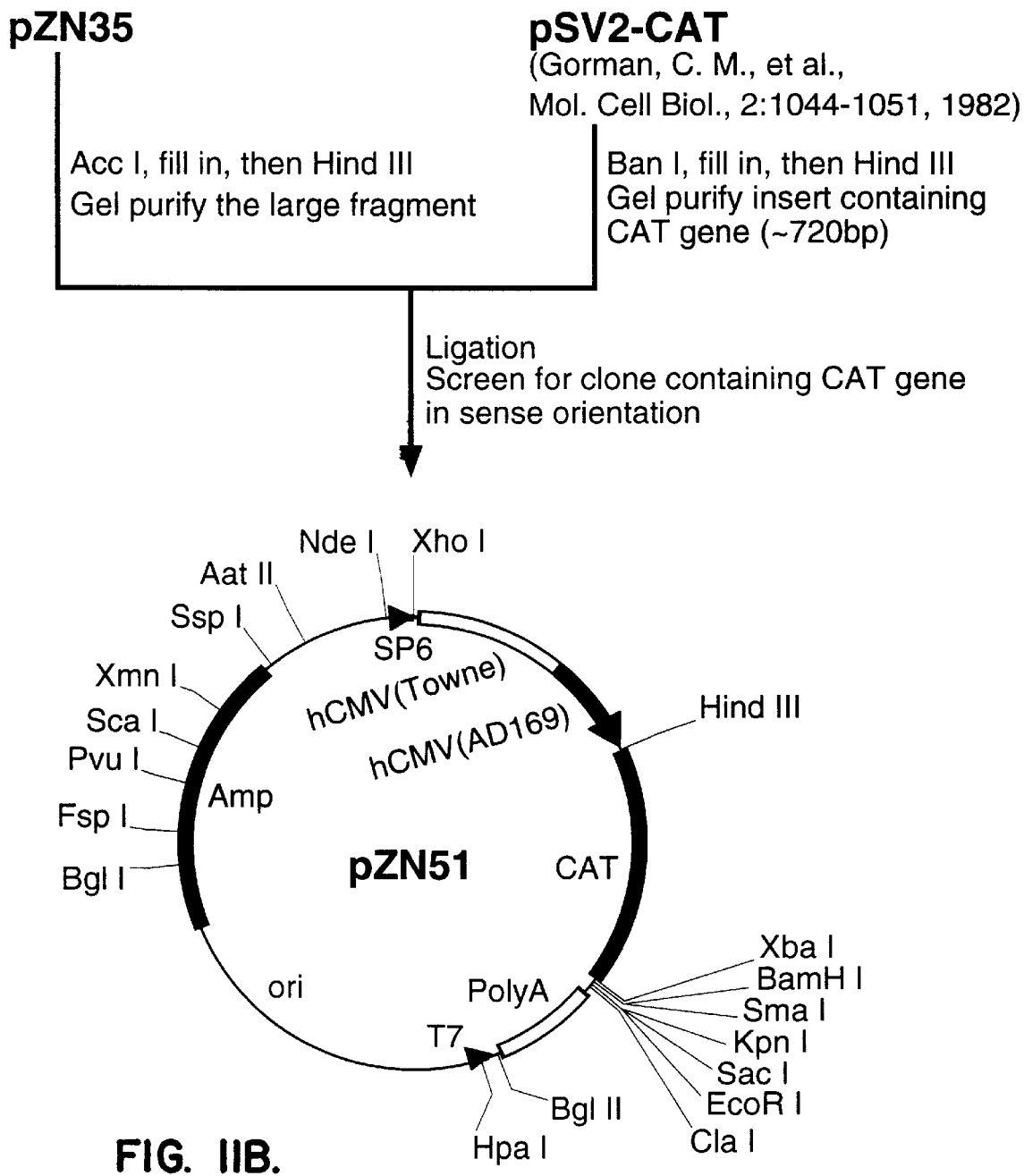
FIG. 11 shows the construction of plasmid pZN51.
Figure 12A:
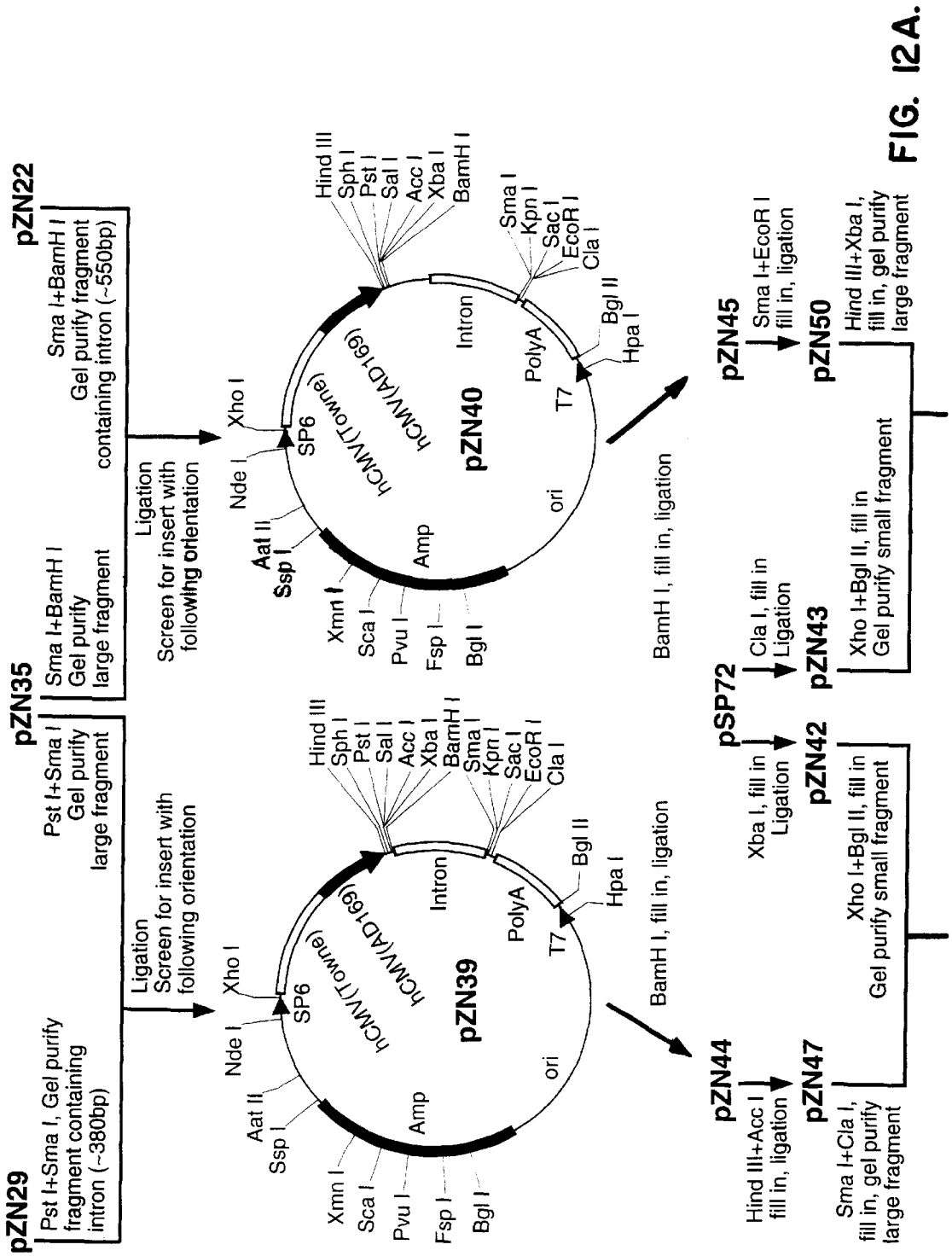
FIG. 12A shows the construction of plasmids pZN47, pZN49, pZN48 and pZN50.
Figures 1, 12B:
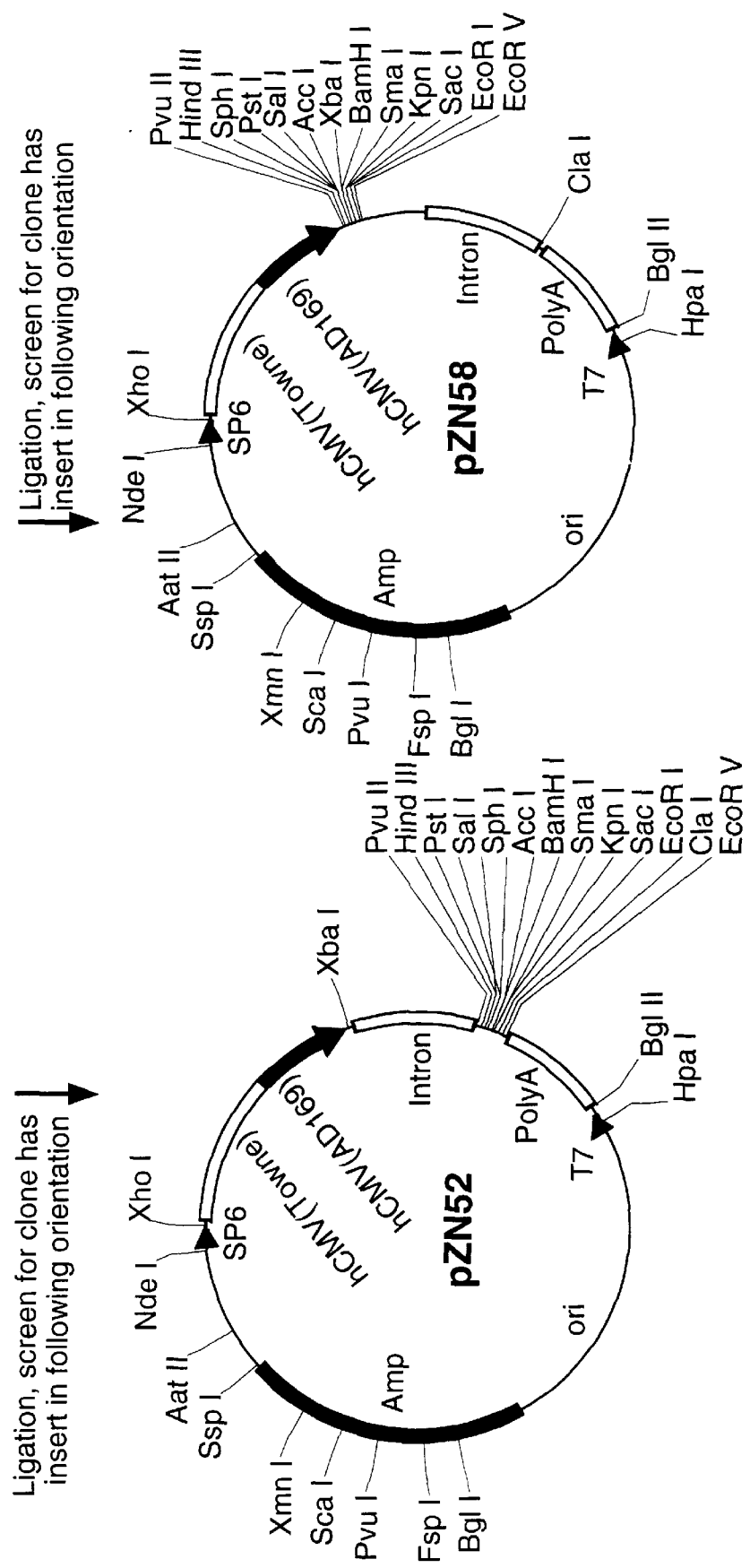
FIG. 12B lanes 1–10, spleen; lanes 11–20, lymph nodes. Each tissue set of 10 contains samples treated with the following in order: 2 samples, 500 µg DNA; 2 samples, 1 mg DNA; 2 samples, 2 mg DNA; 2 samples, 500 µg DNA twice; 2 samples, lipid carrier-DNA complex 100 µg DNA.
Figures 2, 12B:
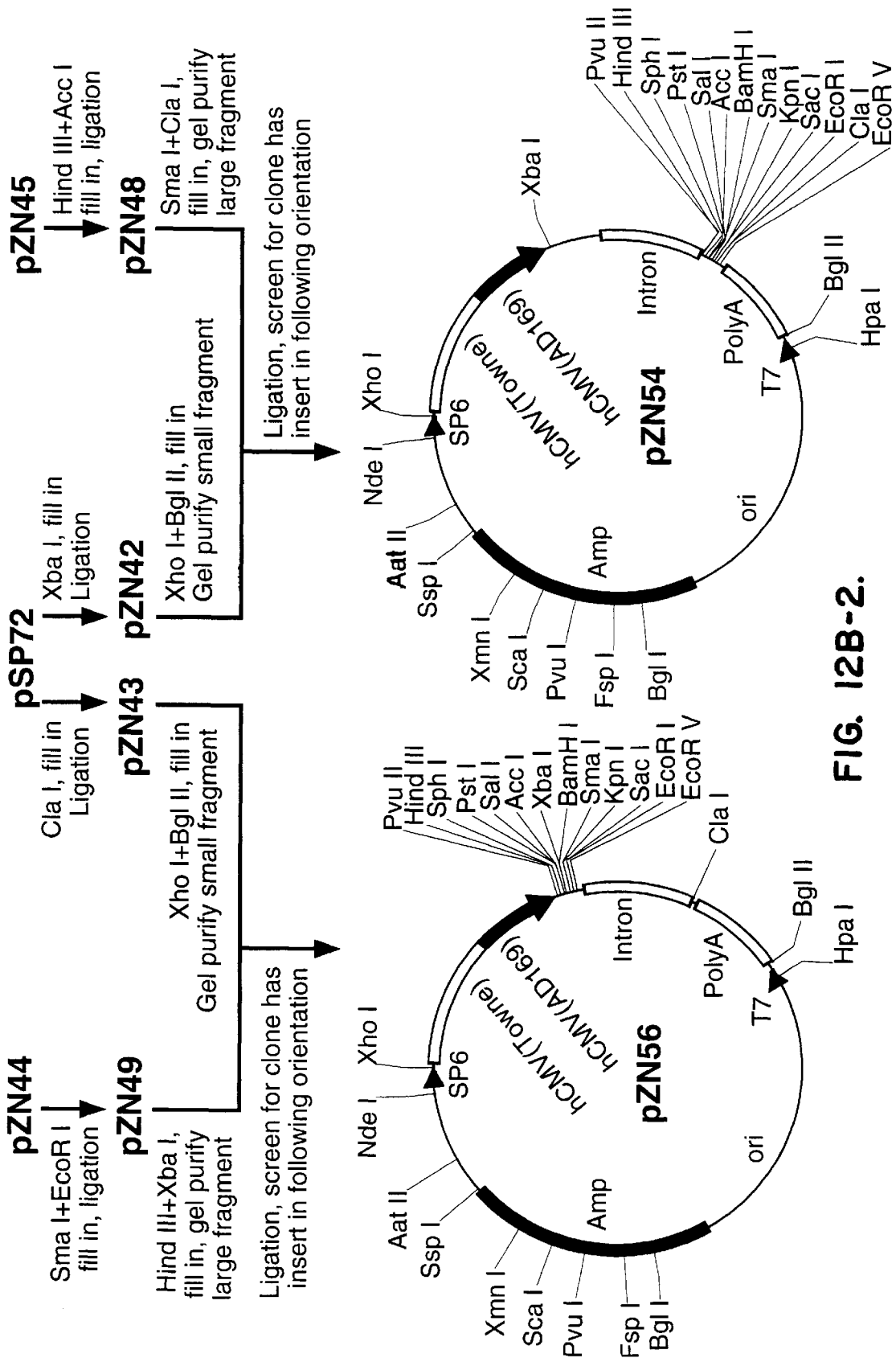
Figures 1, 12C:
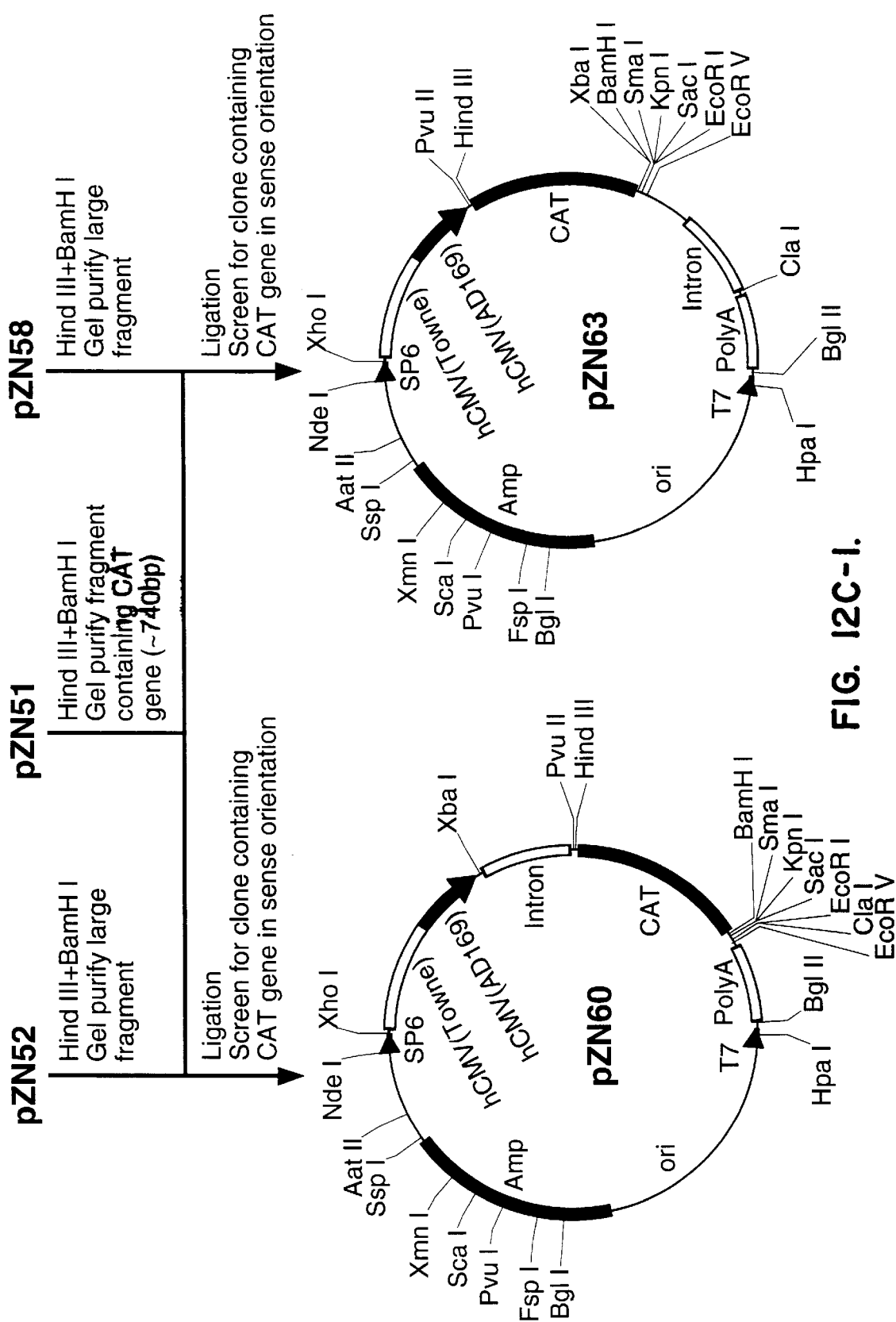
FIG. 12C shows the construction of the final plasmids, pZN60 through pZN63, from the intermediates.
Figures 2, 12C:
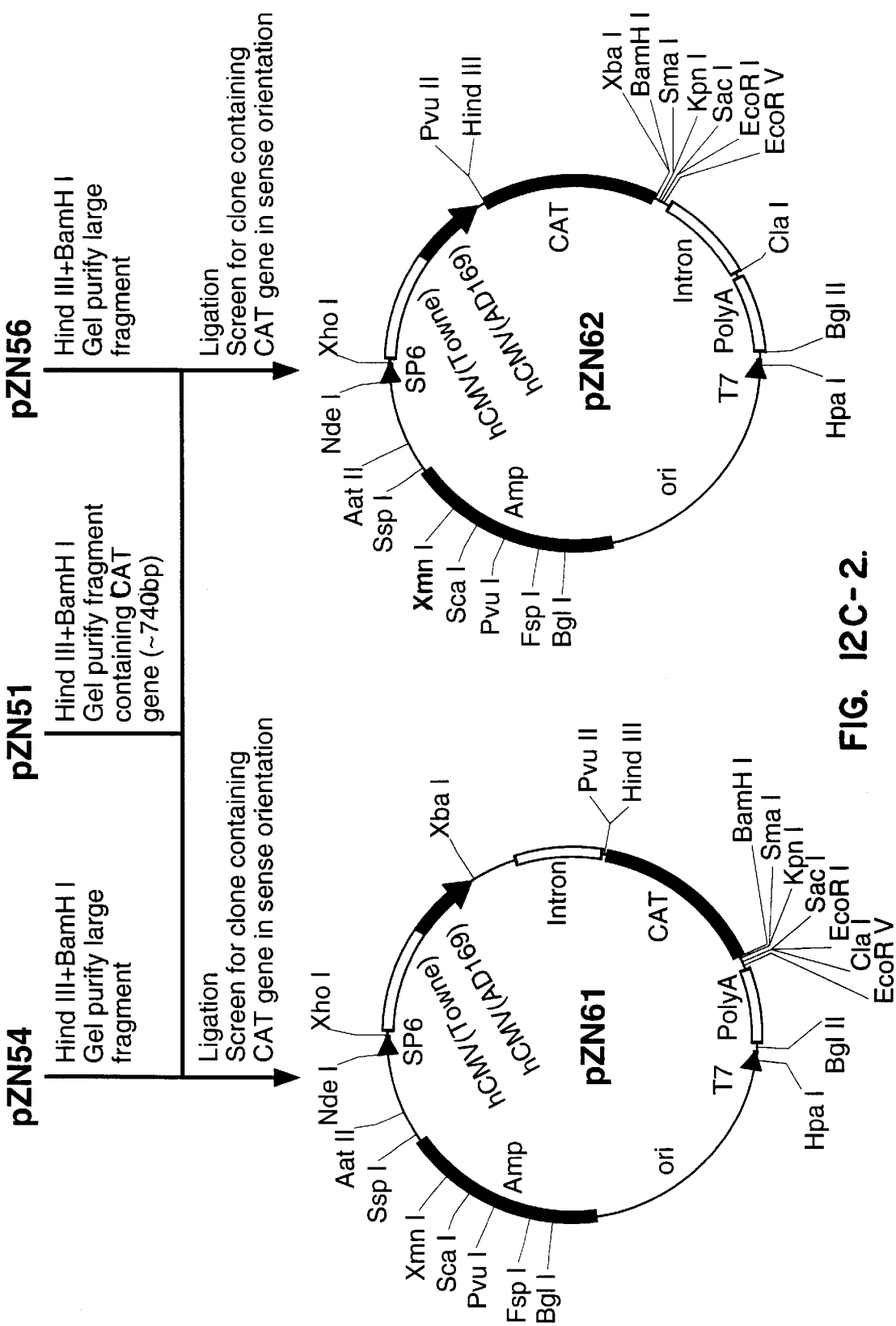

Photomicrographs of frozen sections (viewed at different magnifications) of mouse lung 48 hours following aerosol exposure to pZN32-DDAB:cholesterol (1:1) liposome complexes and lung from untreated control are shown in FIGS. 11A–11E. As demonstrated by the intense staining with the polyclonal anti-CFTR antibody, α-1468, the overwhelming majority of the airways were transfected with the human CFTR gene. See FIGS. 11A, 11C and 11E. By visual inspection, essentially all the cells in transfected airways stain positively, demonstrating that the overwhelming majority of airway cells are transfected with the human CFTR gene in vivo with a single aerosol dose of pZN32 complexed to DDAB-cholesterol (1:1) liposomes. Representative sections are shown in FIG. 11. There was no histologic evidence of lung damage, inflammation or edema present in any of the pZN32-DDAB:cholesterol (1:1) liposome-treated animals. pZN32-DDAB:cholesterol (1:1) liposome-treated and control animals could not be distinguished histologically. Significant expression of the human CFTR gene is present in at least 50% of all the airways and at least 50% of all of the airway lining cells (by visual inspection) in mouse lungs for at least 60 days following a single aerosol dose of pZN32 complexed to DDAB-cholesterol (1:1) liposomes. Frozen sections of mouse lungs from control animals (FIGS. 11B and 11D) do not show any detectable staining for CFTR, confirming that all the CFTR expression present in FIGS. 11A, 11C and 11E is due to transfection of lung cells with the human CFTR gene.

Figure 13:
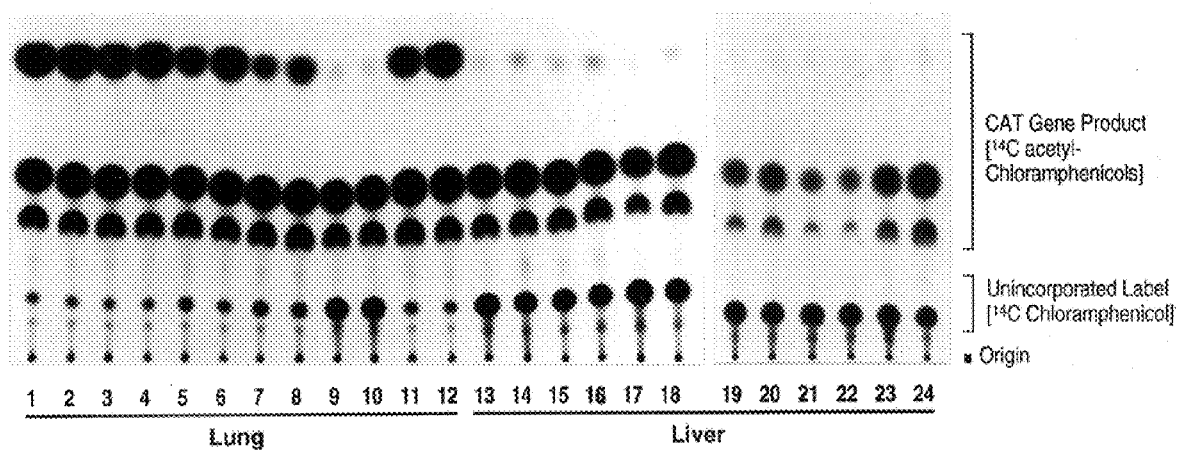
FIG. 13 shows an autoradiograph of the thin layer chromatograph of the CAT assay for six different plasmids injected intravenously in mice. Lanes 1–12 show the CAT activity in lung tissue; Lanes 13–24 show the CAT activity in live tissue. Lanes 1, 2, 13, 14-pZN51; lanes 3, 4, 15, 16-pZN60; lanes 5, 6, 17, 18-pZN61; lanes 7, 8, 19, 20-pZN62; lanes 9, 10, 21, 22-pZN63; lanes 11, 12, 23, 24-pZN27. Lipid carriers were DDAB:Chol (1:1). Lipid carriers-DNA complexes were 5 nmoles cationic lipid to 1 µg DNA. 100 µg DNA was injected per mouse. Each lane represents a single mouse. Chromatograph runs from bottom to top of Figure as shown.
Figure 14A:
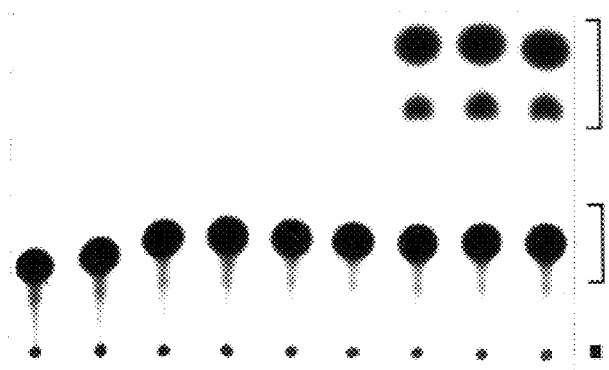
FIGS. 14(A–F) show CAT activity in heart (14A), spleen (14B), lung (14C), LN (14D), kidney (14E), and liner (14F) in lungs from uninjected mice (lanes 1–3), mice injected IV with pBE3.8CAT (lanes 4–6), or pCIS-CAT (lanes 7–9).
Figure 14D:
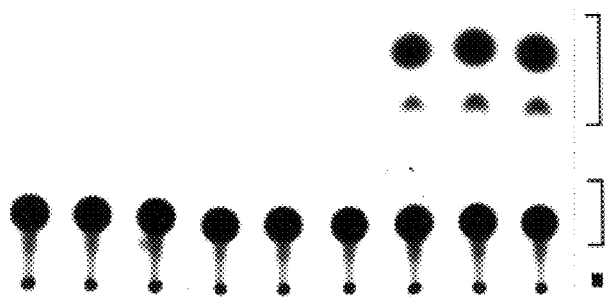
Figure 14E:
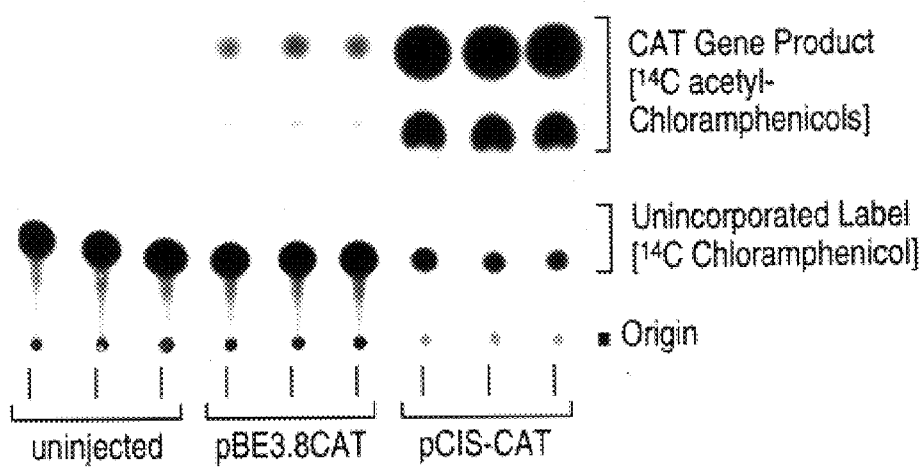
Figure 14B:
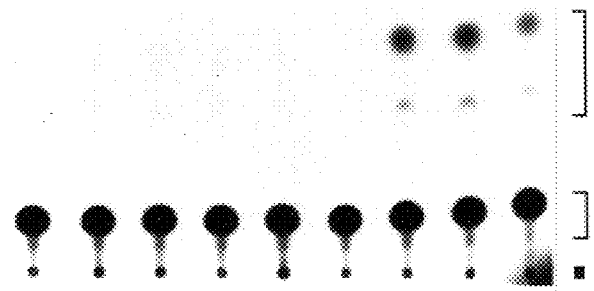
Figure 14C:
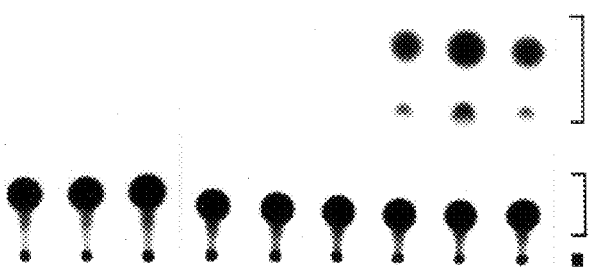
Figure 14F:
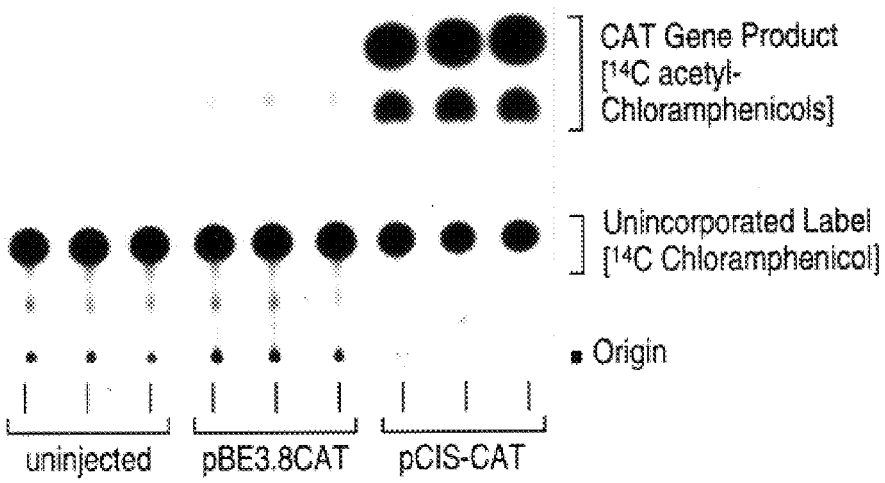
Figure 15A:
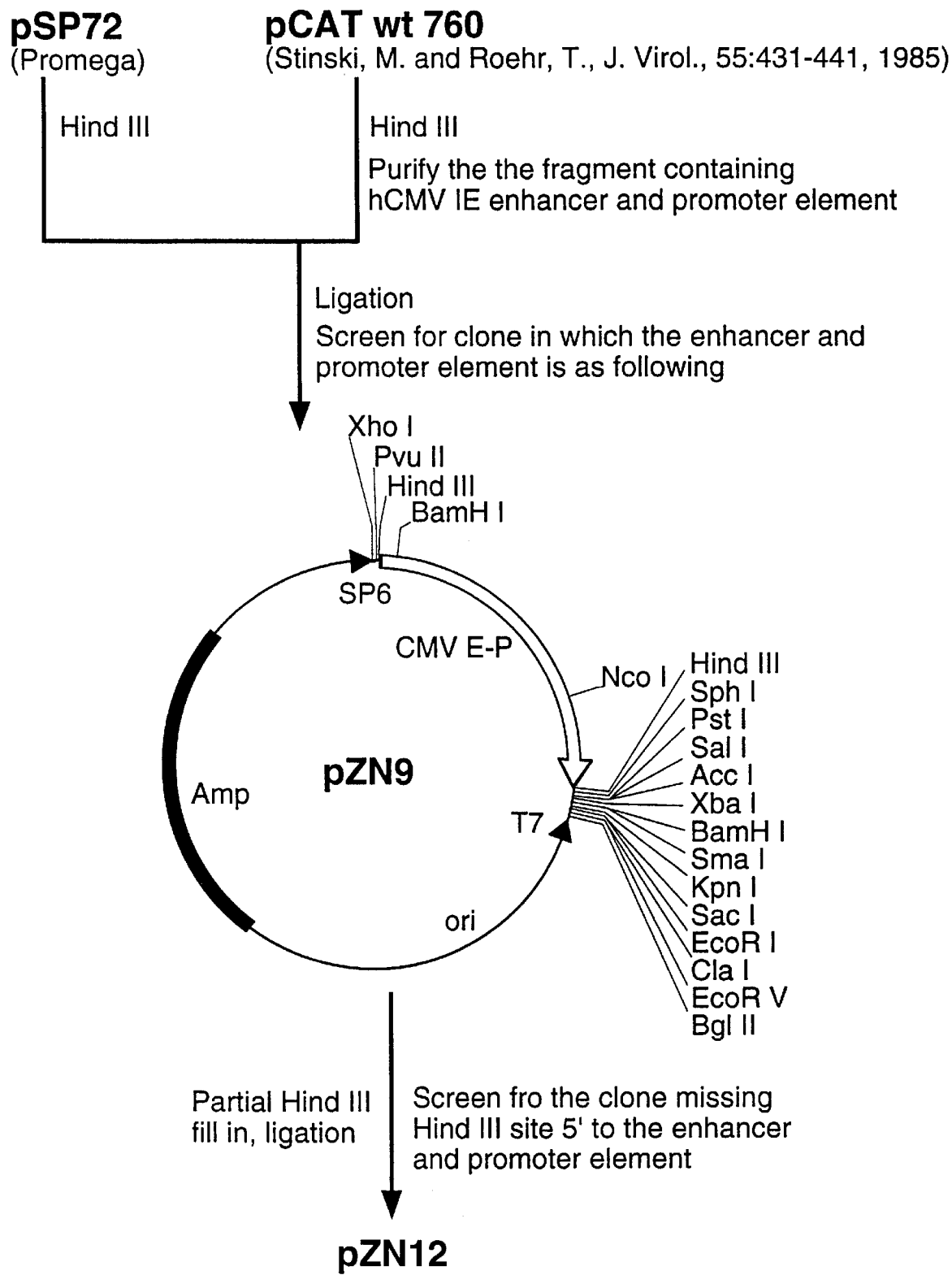
FIG. 15 shows construction of pZN13.
Figure 15B:
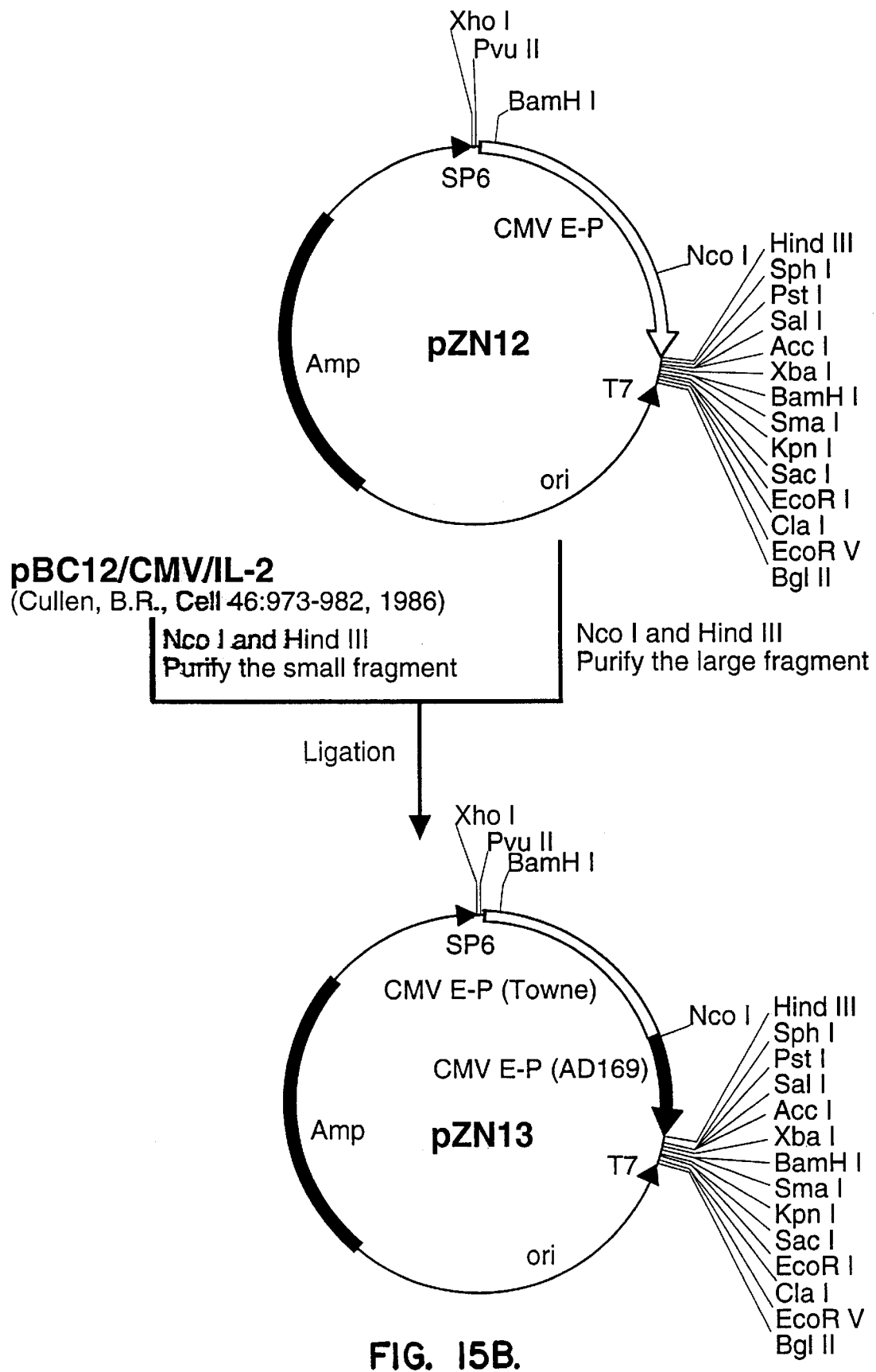
Figure 15C:
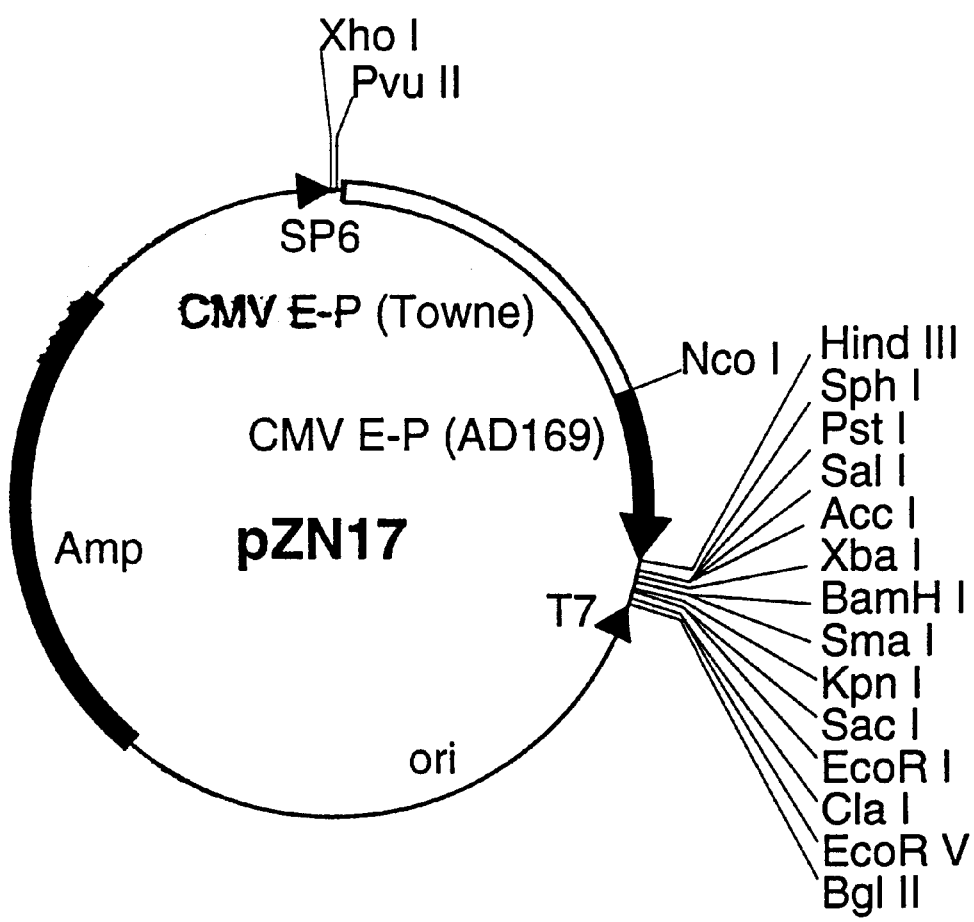
Figure 16A:
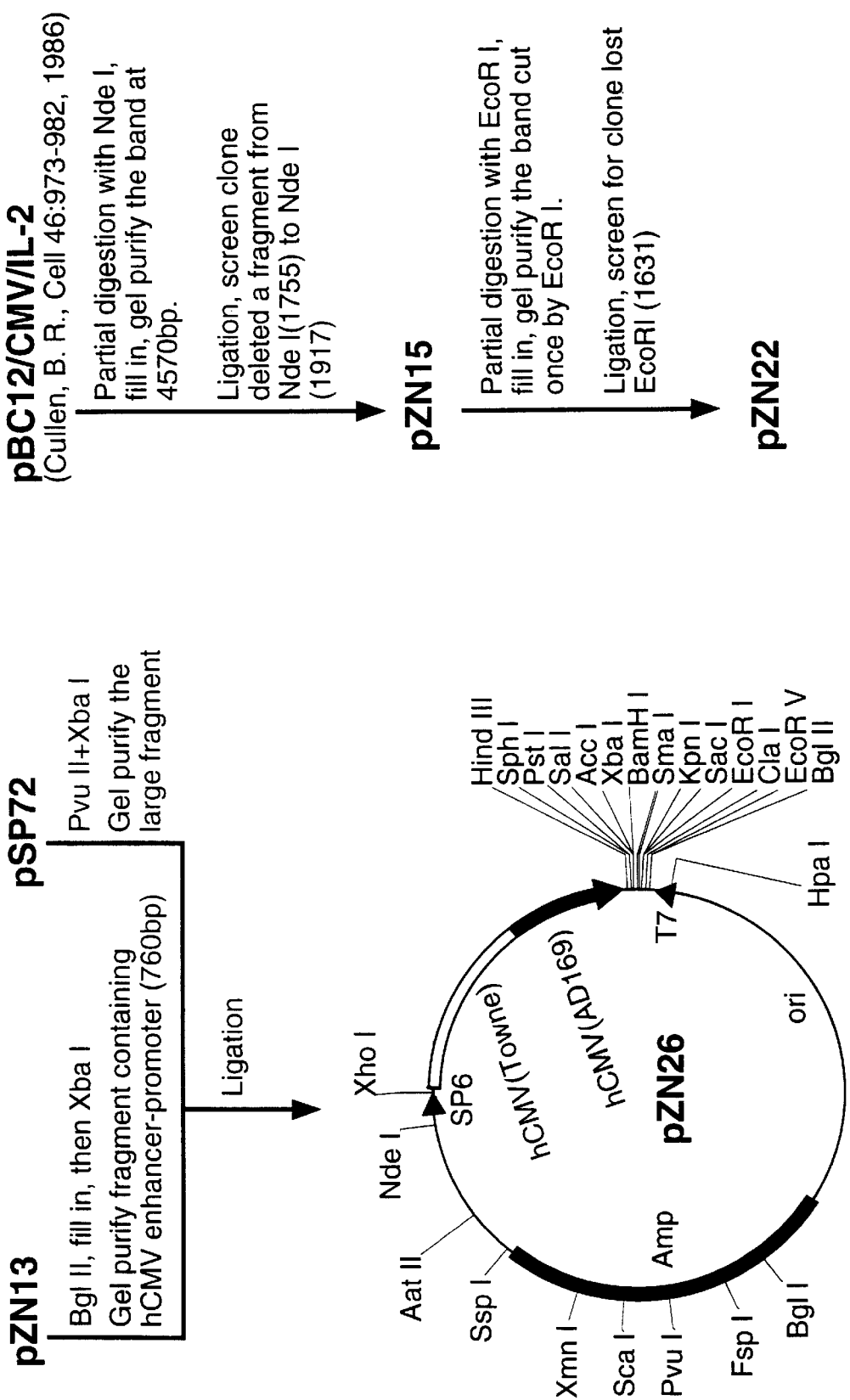
FIG. 16 shows construction of pZN29.
Figure 16B:
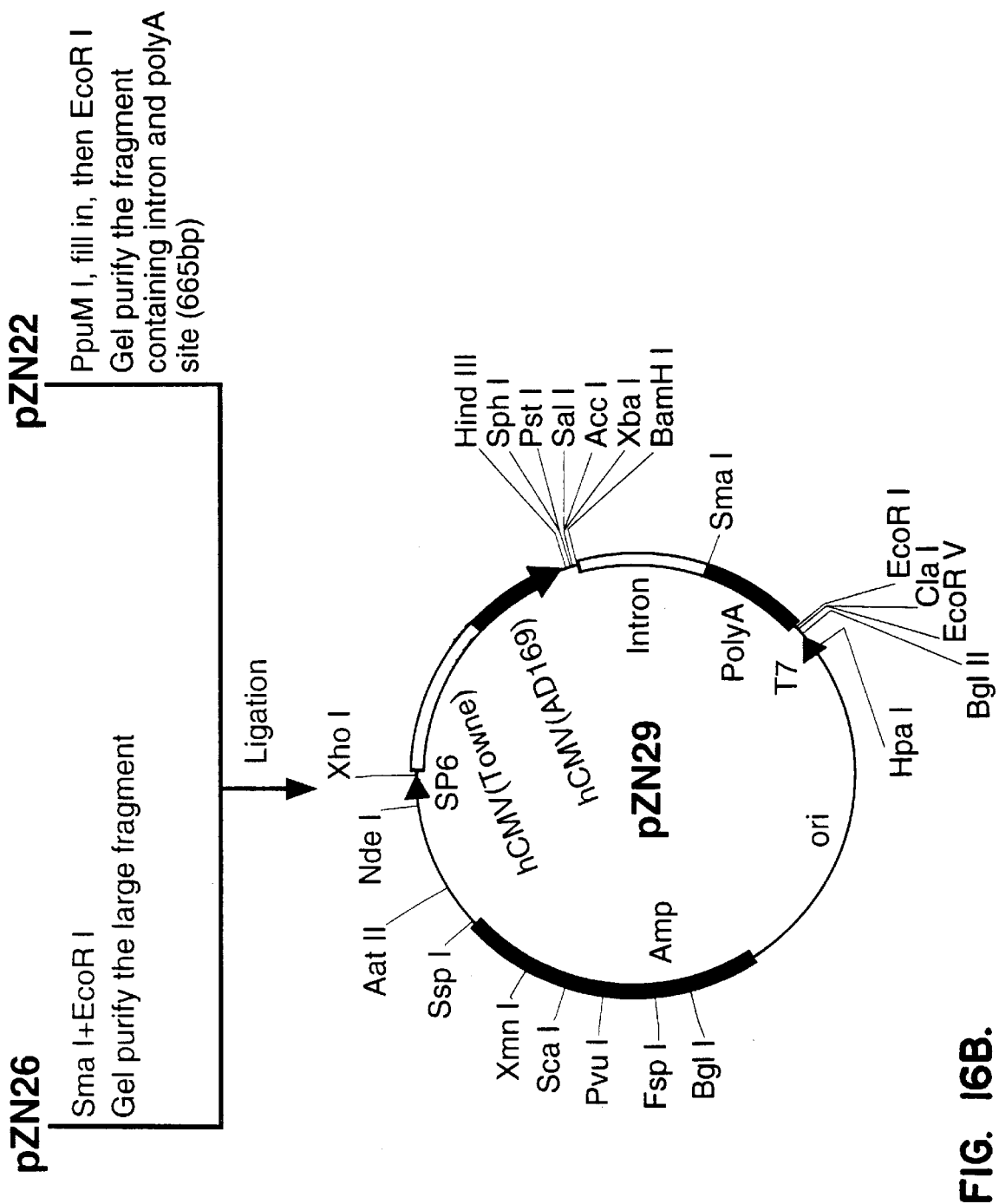
Figure 17:
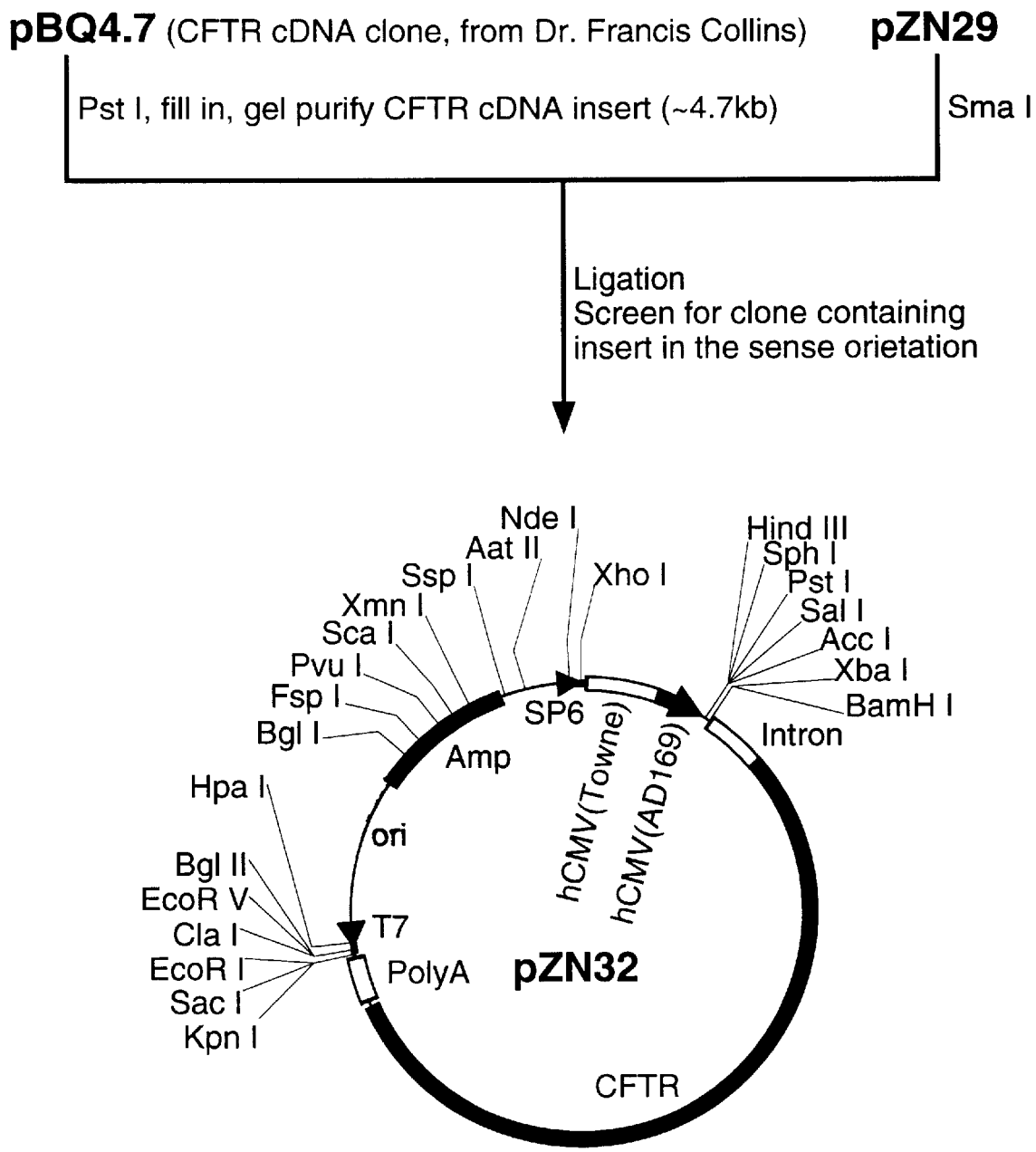
FIG. 17 shows construction of pZN32.

Example 10
Demonstration of CAT Gene Expression in Lung and Liver After Intravenous Injection of Different CAT gene-Containing Plasmids Lipid carrier
  DDAB:Chol=1:1, stock 5 mM in 5% dextrose in water.
Plasmids
  Plasmids are indicated below.
DNA-Lipid carrier Ratio
  Cationic lipid:plasmid DNA=1 nanomole:1 g
Dose
  100 μg DNA in 200 ul volume injected intravenously by tail vein injection.
Mice
  ICR, female, 25 g
Procedure
  The animals were sacrificed 24 hours after injection. The tissue extraction procedure and CAT assay were as described in Example 12 except that the CAT assay was incubated for 3 hr at 37° C. and 2.0 mM paraoxon (Lai, C.-C. et al. Carcinogenesis 9:1295–1302 (1988)) was added to the liver samples. The results are shown in FIG. 13. Lanes 1–12 are lung samples, lanes 13–24 are liver samples. Lanes 1, 2, 13, 14 are pZN51; lanes 3, 4, 15, 16 are pZN60; lanes 5, 6, 17, 18 are pZN61; lanes 7, 8, 19, 20 are pZN62; lanes 9, 10, 21, 22 are pZN63; and lanes 11, 12, 23, 24 are pZN27. pZN51, which does not contain an intron, is expressed as well as or better than plasmids containing an intron.

Example 11

Generalized versus tissue and cell type-specific CAT gene expression produced by iv injection of CMV-CAT-liposome or CFTR-CAT-liposome complexes, respectively
Mouse
  ICR female, 25 grams.
Liposome
  DDAB:Cholesterol=1:1 SUV, 10 mM in 5% dextrose in water.
Plasmid
  1) pZN27 or 2) pBE3.8CAT (see Chou et al., J. Biol Chem 266:24471, 1991 for construction).
Procedure
  Mice in groups of 3 received 1) no treatment, or a single iv tail vein injection of DDAB:CHOL liposomes complexed to 100 μg of 2) a 3.8 kb sequence of the 5' upstream region of the human CFTR gene fused to the CAT gene (pBE3.8CAT) or 3) pZN27. Mice were sacrificed 24 hours later and CAT activity assayed in lung, liver, spleen, lymph nodes, kidney and heart, as described in Example 12. Immunohistochemical analysis of lung section from each of the groups was performed as described in Example 11.
Results
  FIGS. 14A–F CAT assay demonstrated that CMV-CAT produced significant CAT gene expression in the lung, liver, heart, spleen, lymph nodes and kidney, whereas CFTR-CAT produced lung-specific gene expression. Thus, the CMV promoter induces expression of a linked gene in a wide range of tissues, whereas the 5' flanking region of the human CFTR gene directs tissue-specific transgene expression after iv, liposome-based administration.
  Immunohistochemical staining of frozen lung sections from these mice showed that iv injection of CMV-CAT-liposome complexes produced CAT gene expression in endothelial, alveolar and airway cells within the lung. In contrast, CFTR-CAT-liposome complexes produced CAT gene expression primarily in airway epithelial cells. (This approximates the pattern of endogenous CFTR gene expression in rat lung, as determined by in situ hybridization studies (Trezise and Buchwald, Nature, 353:434, 1991). This is the first demonstration that transgenes can be expressed within mouse lung in either a generalized or cell type-specific fashion after iv injection, depending on the regulatory element used. Results are shown in FIGS. 26A–E.

Example 12

High level, lung specific expression of a transgene complexed to cationic liposomes following aerosol administration
Animals
  Two month old, female, ICR mice were used in all experiments.
Preparation of plasmid DNA
  The chloramphenicol acetyltransferase (CAT) gene was used as a reporter to measure transgene expression levels (Gorman et al., Proc. Nat'l Acad Sci (USA) (1982) 79: 6777–6781). The plasmid used contains the CAT gene fused to the human cytomegalovirus (CMV) immediate early promoter-enhancer element (pCIS-CAT). The plasmid was purified using alkaline lysis and ammonium acetate precipitation (Sambrook et al. (1989) supra), and the nucleic acid concentration measured by UV absorption at 260 nm. The CAT gene is not present in eukaryotic cells. Its product is an enzyme which catalyzes the transfer of acetyl groups from acetylCoA to the substrate chloramphenicol.
Preparation of cationic lipid carriers
  Lipid carriers were prepared as small unilamellar vesicles (approximately 100 nm in diameter) containing the cationic lipid DOTMA as DOTMA:DOPE (1:1 mole ratio). DOTMA is (N[1,2,3,-dioleyloxy)propyl]-N,N,N-triethylammonium (Syntex Corporation), and DOPE is the neutral lipid dioleoylphosphatidylethanolamine (Avanti Polar Lipids). Stock solutions of the lipids were dissolved in chloroform and stored under argon at −20° C. Lipids were mixed in a round-bottomed flask and evaporated to dryness on a rotary evaporator under reduced pressure. Double-distilled water was added to produce final lipid concentrations of 10 mM each, and the resulting mix was sonicated for approximately 20 minutes in a bath sonicator (Laboratory Supplies, Hicksville, N.Y.). The liposomes were stored under argon at 40° C. until use.
Aerosol delivery of plasmid/lipid carrier complexes to mice
  Twelve mg of plasmid complexed to 24 μmols of DOTMA:DOPE (1:1) liposomes was aerosolized and administered to mice over two different aerosol periods on the same day. In order to prevent aggregation and precipitation of the oppositely charged components, the plasmid and the liposomes were diluted separately in sterile water prior to mixing. Six mg of plasmid DNA and 12 1mols of DOTMA:DOPE (1:1) liposomes were each diluted to 8 ml with water and mixed. Four ml was then placed into each of two Acorn I nebulizers (Marquest, Englewood, Colo.), the animals placed into an Intox small animal exposure chamber (Albuquerque, N.M.), and an air flow rate of 4 L min$^{-1}$ used to generate the aerosol. Approximately 90 minutes were required to aerosolize 4 ml. The animals were removed from the chamber for 1–2 hours and then the above procedure was repeated with a second 4 ml dose.
Radiometric Assay of CAT Activity
  Organs were dissected from animals sacrificed in a $CO_2$ chamber at periods from 1 to 21 days following aerosolization, washed in cold phosphate buffered saline (PBS), and homogenized using a hand-held tissue homogenizer in 250 mM Tris-HCl, pH 7.5, containing 5 mM EDTA for lungs and spleen and 250 mM Tris-HCl, pH 7.5, containing 5 mM EDTA plus the protease inhibitors aprotinin, E-64, and leupeptic (Boehringer Mannheim) for liver, heart and kidneys. The inhibitors prevent degradation of acetylated chloramphenicol species generated during the assay, thereby allowing optimal detection of CAT expression.
  Following homogenization of the tissue, cells were lysed by three freeze/thaw cycles, the lysate heated (65° C. for 10 minutes), and centrifugated (16,000×g, 2 minutes). The protein concentration of the extracts were measured using a Coomassie blue-based assay (Bio-Rad). Protein concentrations were normalized and a volume of extract added to 10 µl of 100 mM acetylCoA (Sigma), 0.3 µCi of [$^{14}$C]-labelled chloramphenicol (Amersham), and distilled water to a final volume of 180 µl, and allowed to react at 37° C. for 8–10 hours (Gorman et al. (1982) supra). Following the reaction, the acetylated and unacetylated chloramphenicol species were extracted with cold ethyl acetate, spotted on silica TLC plates, and developed with a chloroform:methanol (95:5 v/v) solvent. The TLC plates were exposed to photographic film (Kodak X-OMAT) for one to three days and then read visually.

Preparation of Genomic DNA and Southern Hybridization

Immediately following aerosolization, mice sacrificed and their lungs removed. Genomic DNA was isolated and analyzed by Southern hybridization (Sambrook et al. (1989) supra) using a Hybond N$^+$ membrane (Amersham). A CAT probe was prepared from a 1.6 kb fragment of the CAT gene labelled with α-[$^{32}$P]dATP by random priming, which yielded a probe with an approximate specific activity of 2×10$^9$ dpm/µg. After hybridization, the membrane was washed three times in 2×SSC, 0.1% SDS at 65° C. for 20 minutes and exposed to film for 24 hours. In order to determine the approximate transfected CAT gene copy number, blots were also hybridized with a 1.1 kb BSU 36-1 single copy probe from a mouse factor VIII-A genomic clone (Levinson et al., *Genomics* (1992) 13: 862–865). Relative amounts of the CAT plasmid deposited in individual mouse lungs were quantitated by phosphorimaging analysis using a Molecular dynamics 400A phosphorimaginer (Johnson et al., *Electrophoresis* (1990) 11: 355–360). The amount of retained probe in each lane following hybridization with the CAT probe was normalized to the amount of DNA loaded per lane using the counts measured after hybridization with a Factor VIII-A single copy probe.

In Situ Immunochemical Staining for CAT enzyme

At selected time points following aerosolization, mice were sacrificed and their lungs immediately removed. The lungs were slowly inflated with phosphate buffered saline (PBS) containing 33% by volume OCT (Miles, Inc.), placed in a tissue cassette filled with OCT, and frozen in 2-methylbutane chilled in a dry ice/ethanol bath. Cryosections were cut at 5 µm and collected onto salinized slides. CAT was detected after fixation of cryosections for 10 minutes in either 4% acetone or 2% paraformaldehyde in PBS containing 0.1% Tween 20 (PBST). All subsequent dilution and washes were also done in PBST.

Following fixation, sections were washed three times (5 minutes each) then covered with 10% normal rabbit serum for 10 minutes at 20° C. The serum was replaced with diluted (1:500) rabbit polyclonal antibody against CAT (Drs. Parker Antin and David Standring, UCSF Medical Center). The antibody covered section was gently overlaid with a siliconized coverslip and incubated in a humid chamber at 4° C. for 24 hours. Slides were then warmed to 20° C. and washed three time. The presence of bound rabbit antibody against CAT was detected by covering sections with biotinylated, affinity purified, goat anti-rabbit antibody (Vector Laboratories) diluted 1:300 for 1 hour, followed by washing (3×10 minutes) and replacement with streptavidin labelled with alkaline phosphatase (Zymed, South San Francisco) for 20 minutes. Immobilized alkaline phosphatase was detected using AP-red (Zymed) as the chromogen, with endogenous alkaline phosphatase being inhibited with levamisole (Zymed). To control for potential spurious adherence of the streptavidin conjugate to bronchiolar epithelium, some sections were treated with free avidin and biotin prior to application of the primary antibody. Other controls, run concurrently, included the use of normal rabbit serum in place of primary antibody and the use of lung tissue from untreated mice. Photo-microscopy was performed using Kodak Ektachrome 64T film x50 (FIGS. 6A,D) and x250 (FIGS. 6B,C,E,F).

Results

Initially, mice were exposed either to an aerosol generated from a solution containing 12 mg of a CMV-CAT expression plasmid alone or to an aerosol generated from a solution containing 12 mg of CMV-CAT complexed to 24 µmoles of DOTMA:DOPE (1:1) liposome. Aerosols were administered to animals after they were placed individually in nose-out cones and inserted into an Intox small animal exposure chamber. The mice showed no apparent ill effects or respiratory distress either during or after aerosol exposure. FIG. 7 shows the results of CAT assays from extracts of the lungs of mice sacrificed 72 hours following aerosol administration. Significant CAT gene expression was seen only in mice exposed to aerosolized DNA/lipid carrier complexes.

Figure 24A:
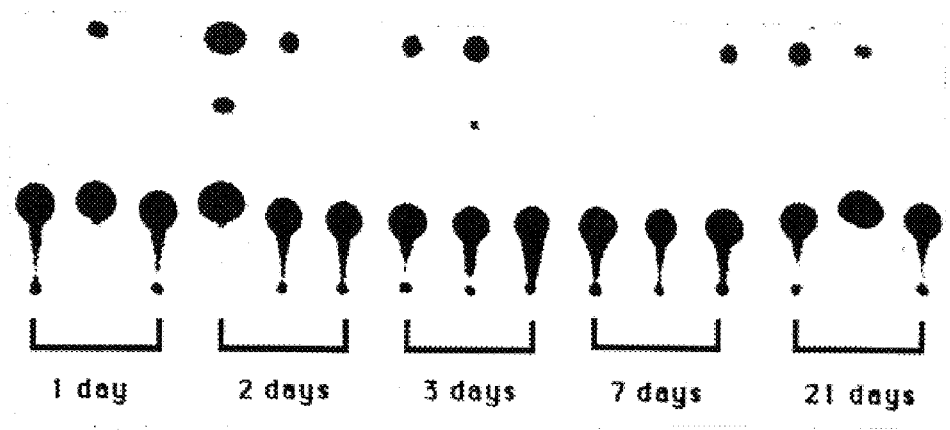
FIGS. 24(A–B) shows (A) CAT activity in lung extracts from mice sacrificed from one to twenty-one days after receiving an aerosol containing 12 mg of pCIS-CAT plasmid complexed to 24 μmols of DOTMA:DOPE liposomes; and (B) shows CAT activity in several different tissue extracts from mice and indicates that expression of the transgene is lung-specific after aerosolization of DNA-liposome complexes into normal mice sacrificed at the three day time point in FIG. 8A. Control extract contains CAT enzyme.
Figure 24B:
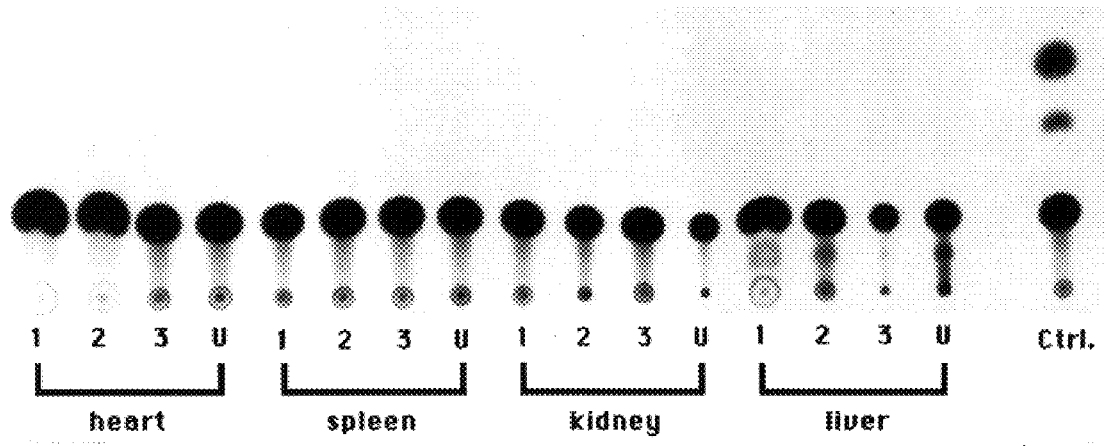

How long CAT protein was present in the lungs of mice and whether expression of the reporter gene was limited to the lung was also investigated. Despite inter-animal variation, high levels of CAT activity are present for at least 21 days following a single aerosol dose of DNA/lipid carrier complexes (FIG. 24A). No CAT activity was detectable in extracts from the heart, spleen, kidneys or liver of animals that showed high level expression in the lung (FIG. 24B), suggesting that transgene expression following aerosol delivery is restricted to the lung. This is consistent with prior observations showing that penetration of very high molecular weight substances through the respiratory epithelium of normal animals is very limited. Plasmid DNA/lipid carrier complexes have molecular weights greater than 10$^6$ daltons.

Although the small animal exposure chamber used in these experiments is designed to efficiently deliver a uniform aerosol dose to multiple animals up to 48 individual animals, we have observed significant variations in the level of CAT activity in the lungs of mice within a single experiment. One possible explanation for this variability is that the amount of DNA/liposome complex deposited in the lungs of mice is not uniform. In order to test this hypothesis, initial lung deposition of liposomes was measured using fluorescence analysis and initial lung deposition of DNA was measured using Southern blot analysis.

Figure 25:
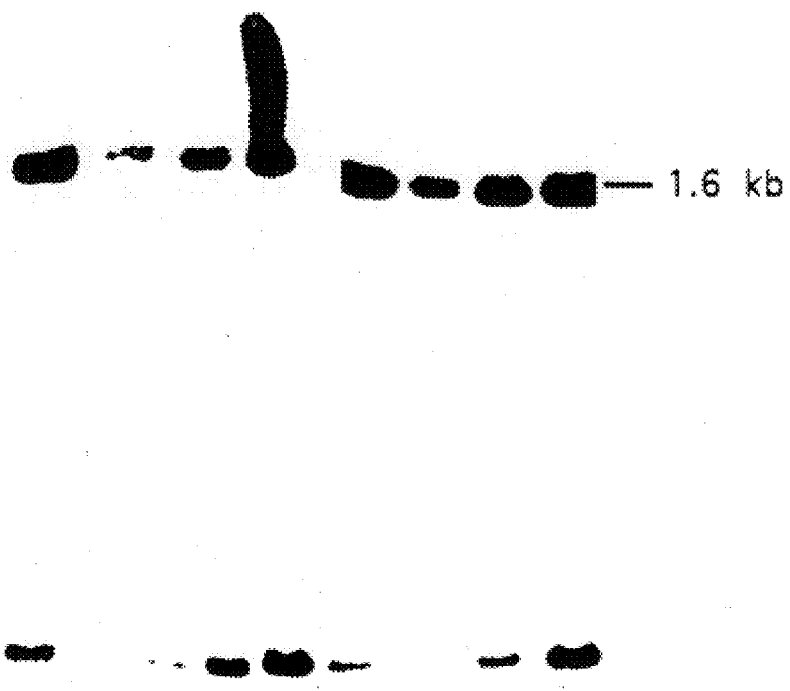
FIG. 25 shows Southern blot hybridization of genomic DNA from the lungs of mice sacrificed immediately after receiving an aerosol containing 12 mg of pCIS-CAT plasmid complexed to 24 μmols of DOTMA:DOPE liposomes (lanes 1–4, 6–9) and from an untreated control mouse (lane 5). Samples were digested with the restriction enzyme HindIII and probed with a 1.6 kb CAT fragment (upper panel). The same membrane was hybridized with a 1.1 kb BSU 36-1 single copy probe from a mouse factor VIII. A genomic clone (lower panel).
Figure 26A:
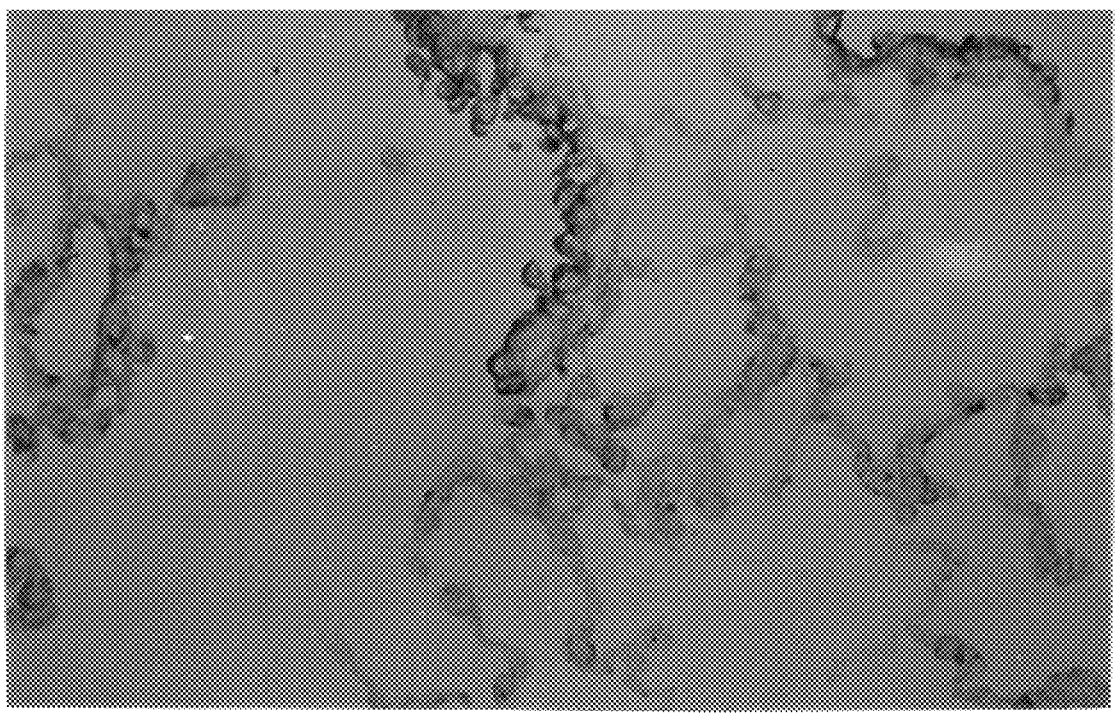
FIGS. 26(A–E) show histological analysis of CAT activity in lung from mice injected with CMV-CAT (FIGS. 26A and 26D), CFTR-CAT (FIGS. 26B and 26D) and control animals (FIGS. 26C and 26E).
Figure 26B:
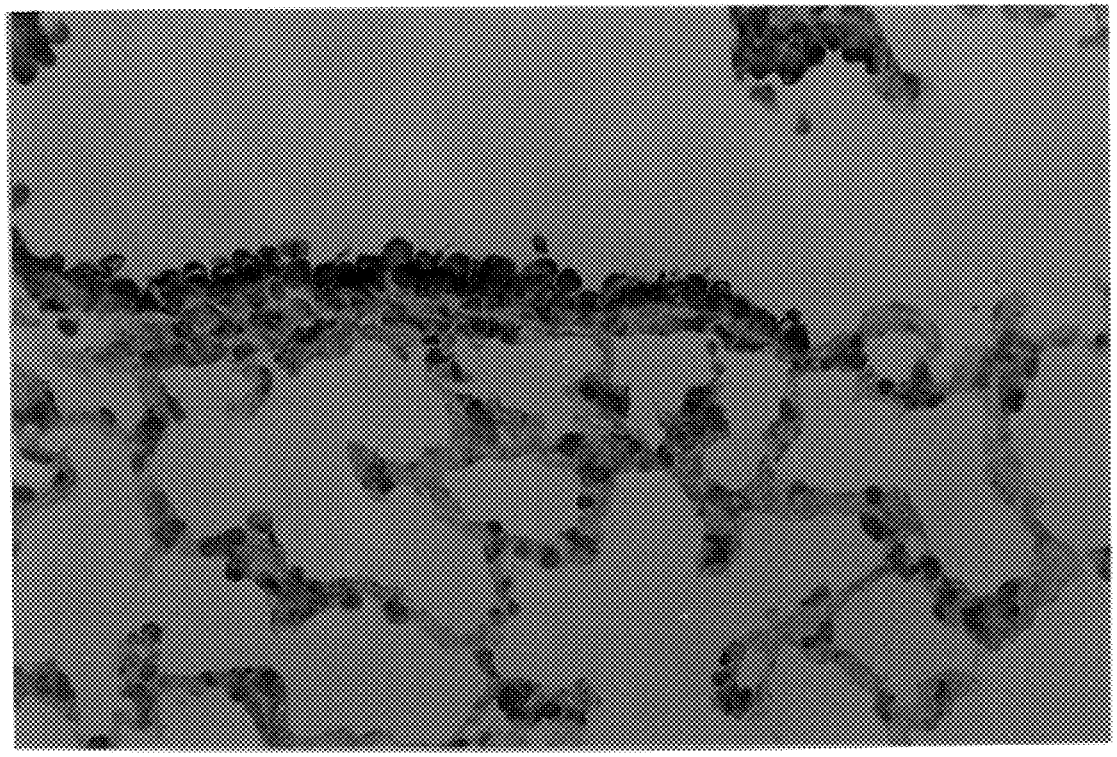
Figure 26C:
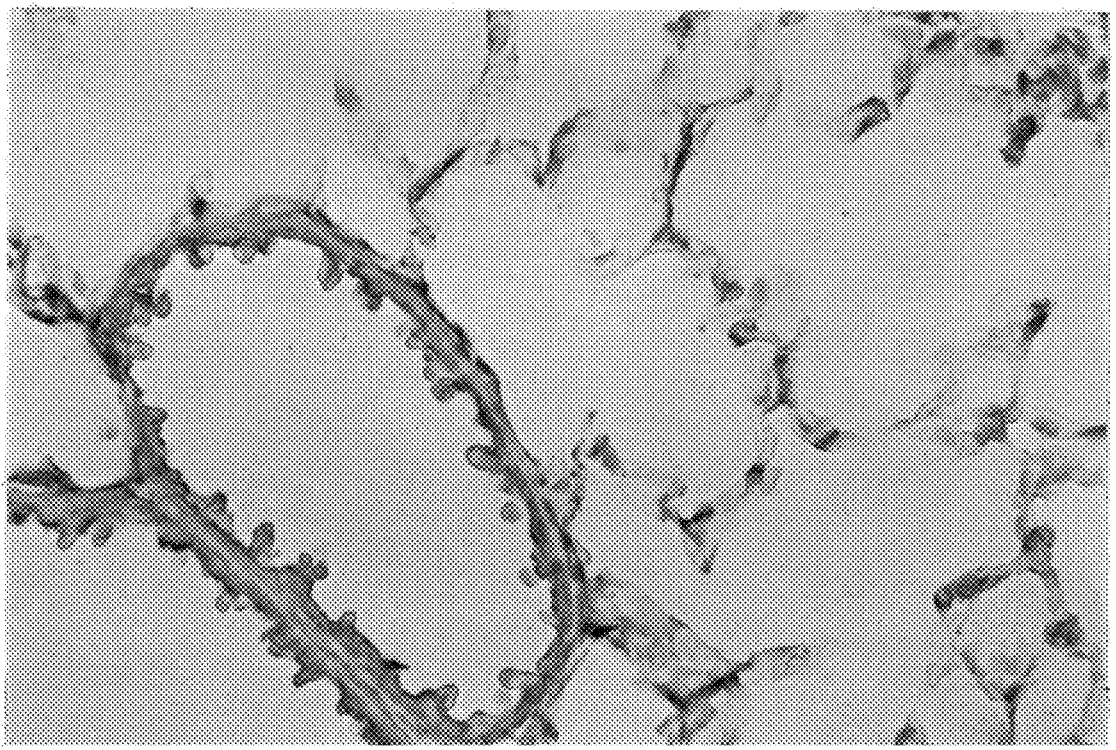
Figure 26D:
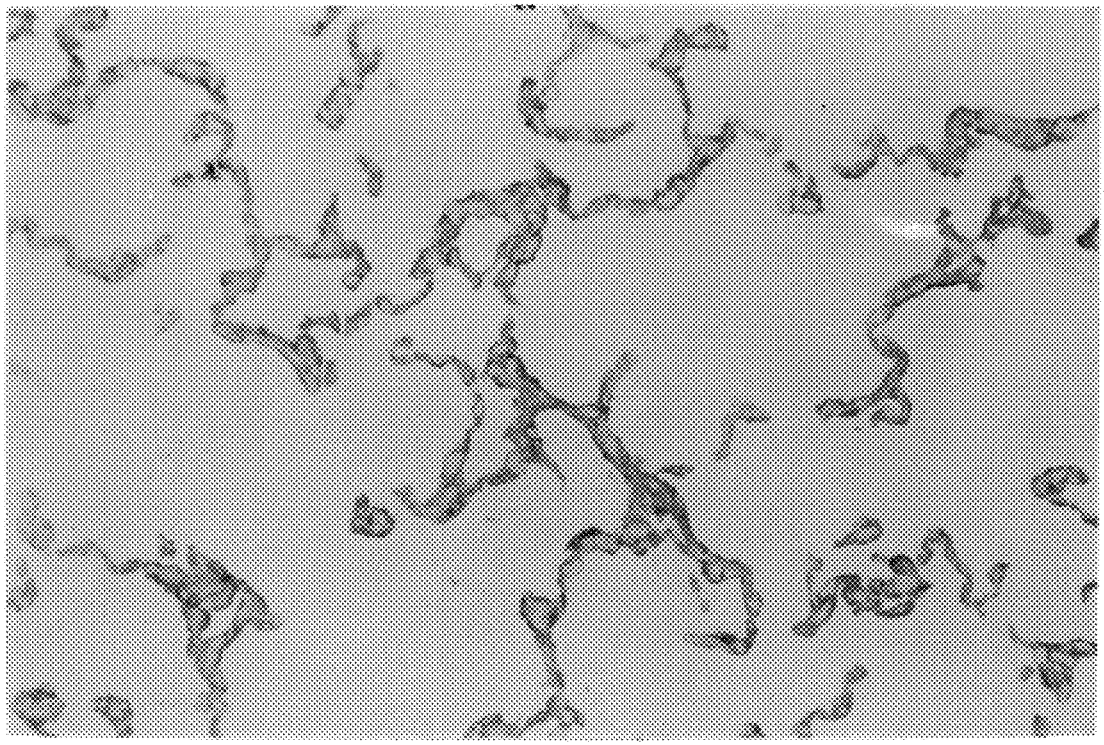
Figure 26E:
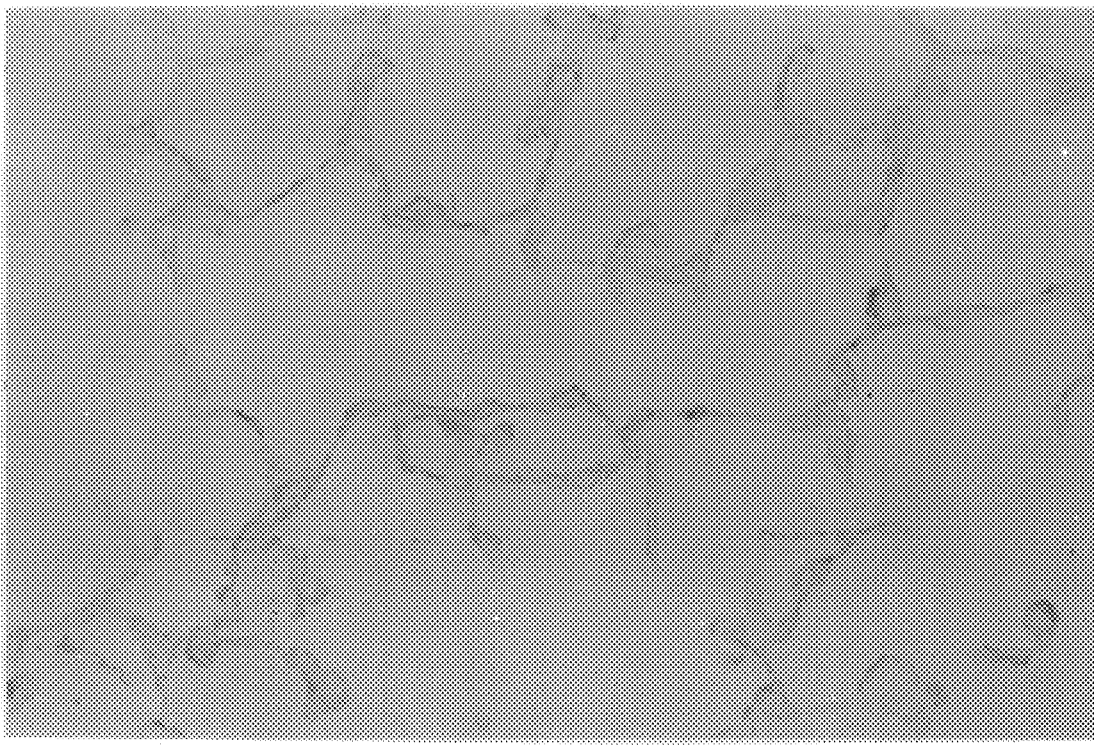

Aerosolized cationic liposomes alone or DNA/liposome alone or DNA/liposome complexes containing 0.5 mole percent of a fluorescently labelled lipid, rhodamine-phosphatidylethanolamine, were administered to mice. Immediately following aerosolization, the animals were sacrificed and their lungs removed, homogenized and rhodamine fluorescence measured using a fluorimeter. The recovered fluorescence per animal was 0.06%±0.02 (S.D.) of the total amount aerosolized. This suggests that less than 10 µg out of the 12 mg of DNA aerosolized per experiment was actually deposited in the lung. In addition, there was no significant difference in lipid deposition between animals receiving liposomes alone and those receiving the DNA/liposomes complexes. Since it is possible that a disruption of the complex could have occurred during nebulization, the amount of CAT gene deposited during aerosolization (FIG. 25) was also assessed. Immediately following aerosol delivery of DNA/lipid carrier complexes, mice were sacrificed and total lung DNA prepared. Southern blots were probed with α[32P]-labelled CAT gene. Labelled bands were scanned and demonstrated less than a 4-fold difference in plasmid deposition between animals in the same experiment (FIG. 25). These results suggest that the mouse to mouse variation in CAT gene levels following aerosol delivery (up to ten-fold) is not only a function of the amount of complex initially deposited in the lung, but also may reflect differences in the site of uptake, rate of lung clearance, and/or variation in the ability of different lung cell types to express the transgene.

To determine the types and percentage of lung cells which were transfected in vivo, lungs of mice sacrificed 72 hours following exposure to an aerosol containing DNA/liposome complexes were cryosectioned, probed with a polyclonal anti-CAT antibody and counterstained to detect intracellular CAT protein (FIG. 22). Lung sections taken from DNA/lipid carrier treated mice had a diffuse immunostaining pattern involving involving bronchiolar and alveolar components. The bronchiolar epithelial cytoplasm stained with greatest intensity and uniformity. CAT antigen was detected (as demonstrated by red staining) in nearly all conducting airways with only rare individual or 2–3 cell clusters not staining (FIGS. 22A, 22B). The diffuse alveolar pattern was due to moderately intense staining of the majority of alveolar lining cells (FIG. 22C). These areas occasionally faded into small, randomly scattered regions where lining cell staining was faint. Focal, intense staining (arrows) occurred in the cytoplasm of scattered, individual, alveolar lining cells (FIG. 22C). Controls included substitution of the primary antibody with normal rabbit serum (FIG. 22D) and use of lung sections from untreated animals (FIGS. 22E, 22F). Immunostaining was not detectable in either of the control preparations. Examination of multiple sections of lung from treated and control mice demonstrated no significant lesions which would indicate adverse effects of the aerosol treatment.

As shown by the above results, a single aerosol dose of an expression liposome, containing a gene of interest, complexed to cationic liposomes transfects the majority of the cells lining both the conducting airways and the alveoli of the lung, the gene product is present in the lung for at least 60 days, the expression appears to be lung-specific, and there is no histological evidence of damage following exposure. Thus, the aerosolized cationic liposomes mediate efficient transfection of non-dividing as well as dividing cells. This is important because many airway epithelial cells are well differentiated and divide slowly or not at all. The lipid carriers appear to be both well tolerated and non-immunogenic. Furthermore, the appearance, behavior and life span of mice treated with either aerosolized or injected pZN32: DDAB-cholesterol (1:1) complexes appear normal and are indistinguishable from untreated, normal control animals, demonstrating the lack of toxicity of these carrier constructs, and the overexpression of the human CFTR gene in mammals. Additionally, the effects of repeated aerosol administration of the DNA/liposome complexes is effective and is non-toxic. The cationic liposome-mediated DNA delivery by aerosol provides high level, lung-specific transgene expression in vivo.

All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH:     616
      (B) TYPE:       nucleic acid
      (C) STRANDEDNESS: single
      (D) TOPOLOGY:   linear (xi) SEQUENCE DESCRIPTION: SEQ ID NO: 1:

```
GGCGACCGCC CAGCGACCCC CGCCCGTTGA CGTCAATAGT GACGTATGTT CCCATAGTAA      60

CGCCAATAGG GACTTTCCAT TGACGTCAAT GGGTGGAGTA TTTACGGTAA ACTGCCTACT     120

TGGCAGTACA TCAAGTGTAT CATATGCCAA GTCCGCCCCC TATTGACGTC AATGACGGTA     180

AATGGCCCGC CTAGCATTAT GCCCAGTACA TGACCTTACG GGAGTTTCCT ACTTGGCAGT     240

ACATCTACGT ATTAGTCATC GCTATTACCA TGGTGATGCG GTTTTGGCAG TACACCAATG     300

GGCGTGGATA GCGGTTTGAC TCACGGGGAT TTCCAAGTCT CCACCCCATT GACGTCAATG     360

GGAGTTTGTT TTGGCACCAA AATCAACGGG ACTTTCCAAA ATGTCGTAAT AACCCCGCCC     420

CGTTGACGCA AATGGGCGGT AGGCGTGTAC GGTGGGAGGT CTATATAGCA GAGCTCGTTT     480

AGTGAACCGT CAGATCGCCT GGAGACGCCA TCCACGCTGT TTTGACCTCC ATAGAAGACA     540

CCGGGACCGA TCCAGCCTCC GCGGCCGGGA ACGGTGCATT GGAACGCGGA TTCCCCGTGC     600
```

```
CAAGAGTGAC GTAAGT                                                      616

(2) INFORMATION FOR SEQ ID NO: 2:

(i) SEQUENCE CHARACTERISTICS:
        (A) LENGTH:       930
        (B) TYPE:         nucleic acid
        (C) STRANDEDNESS: single
        (D) TOPOLOGY:     linear (xi) SEQUENCE DESCRIPTION: SEQ ID NO: 2:

AATCAATATT GGCCATTAGC CATATTATTC ATTGGTTATA TAGCATAAAT CAATATTGGC        60

TATTGGCCAT TGCATACGTT GTATCCATAT CATAATATGT ACATTTATAT TGGCTCATGT       120

CCAACATTAC CGCCATGTTG ACATTGATTA TTGACTAGTT ATTAATAGTA ATCAATTACG       180

GGGTCATTAG TTCATAGCCC ATATATGGAG TTCCGCGTTA CATAACTTAC GGTAAATGGC       240

CCGCCTGGCT GACCGCCCAA CGACCCCCGC CCATTGACGT CAATAATGAC GTATGTTCCC       300

ATAGTAACGC CAATAGGGAC TTTCCATTGA CGTCAATGGG TGGAGTATTT ACGGTAAACT       360

GCCCACTTGG CAGTACATCA AGTGTATCAT ATGCCAAGTA CGCCCCCTAT TGACGTCAAT       420

GACGGTAAAT GGCCCGCCTG GCATTATGCC CAGTACATGA CCTTATGGGA CTTTCCTACT       480

TGGCAGTACA TCTACGTATT AGTCATCGCT ATTACCATGG TGATGCGGTT TTGGCAGTAC       540

ATCAATGGGC GTGGATAGCG GTTTGACTCA CGGGGATTTC CAAGTCTCCA CCCCATTGAC       600

GTCAATGGGA GTTTGTTTTG GCACCAAAAT CAACGGGACT TTCCAAAATG TCGTAACAAC       660

TCCGCCCCAT TGACGCAAAT GGGCGGTAGG CGTGTACGGT GGGAGGTCTA TATAAGCAGA       720

GCTCGTTTAG TGAACCGTCA GATCGCCTGG AGACGCCATC CACGCTGTTT TGACCTCCAT       780

AGAAGACACC GGGACCGATC CAGCCTCCGC GGCCGGGAAC GGTGCATTGG AACGCGGATT       840

CCCCGTGCCA AGAGTGACGT AAGTACCGCC TATAGAGTCT ATAGGCCCAC CCCCTTGGCT       900

TCTTATGCAT GCTATACTGT TTTTGGCTTG                                       930

(2) INFORMATION FOR SEQ ID NO: 3:

(i) SEQUENCE CHARACTERISTICS:
        (A) LENGTH:       616
        (B) TYPE:         nucleic acid
        (C) STRANDEDNESS: single
        (D) TOPOLOGY:     linear (xi) SEQUENCE DESCRIPTION: SEQ ID NO: 3:

GGCGACCGCC CAGCGACCCC CGCCCGTTGA CGTCAATAGT GACGTATGTT CCCATAGTAA        60

CGCCAATAGG GACTTTCCAT TGACGTCAAT GGGTGGAGTA TTTACGGTAA ACTGCCCACT       120

TGGCAGTACA TCAAGTGTAT CATATGCCAA GTCCGCCCCC TATTGACGTC AATGACGGTA       180

AATGGCCCGC CTAGCATTAT GCCCAGTACA TGACCTTACG GGAGTTTCCT ACTTGGCAGT       240

ACATCTACGT ATTAGTCATC GCTATTACCA TGGTGATGCG GTTTTGGCAG TACACCAATG       300

GGCGTGGATA GCGGTTTGAC TCACGGGGAT TTCCAAGTCT CCACCCCATT GACGTCAATG       360

GGAGTTTGTT TTGGCACCAA AATCAACGGG ACTTTCCAAA ATGTCGTAAT AACCCCGCCC       420

CGTTGACGCA AATGGGCGGT AGGCGTGTAC GGTGGGAGGT CTATATAGCA GAGCTCGTTT       480

AGTGAACCGT CAGATCGCCT GGAGACGCCA TCCACGCTGT TTTGACCTCC ATAGAAGACA       540

CCGGGACCGA TCCAGCCTCC GCGGCCGGGA ACGGTGCATT GGAACGCGGA TTCCCCGTGC       600

CAAGAGTGAC GTAAGT                                                      616
```

```
(2) INFORMATION FOR SEQ ID NO: 4:

(i) SEQUENCE CHARACTERISTICS:
        (A) LENGTH:       15
        (B) TYPE:         nucleic acid
        (C) STRANDEDNESS: single
        (D) TOPOLOGY:     linear (xi) SEQUENCE DESCRIPTION: SEQ ID NO: 4:

YYYYYYYYY YNYAG                                                    15
```

What is claimed is:

1. A mammalian transformation complex, comprising:
   a lipid carrier, comprising cationic lipid and a non-cationic lipid, wherein the complex is between about 100 nanometers and 10 microns in diameter; and
   a DNA expression cassette comprising a promoter in operable linkage with a polynucleotide encoding a functional cystic fibrosis transmembrane conductance regulator (CFTR), wherein said DNA expression cassette is in a ratio of less than 4:1 micrograms DNA to nanomoles cationic lipid; and
   wherein said complex does not aggregate in vitro.

2. The mammalian transformation complex of claim 1, wherein the non-cationic lipid is a steroid.

3. The mammalian transformation complex of claim 1, wherein the non-cationic lipid is cholesterol.

4. The mammalian transformation complex of claim 1, wherein the cationic lipid and non-cationic lipid are in a molar ratio of about 1:1.

5. The mammalian transformation complex of claim 1, wherein the lipid carrier is an MLV (multilamellar vesicle).

6. The mammalian transformation complex of claim 1, wherein the lipid carrier is an SUV (small unilamellar vesicle).

7. The mammalian transformation complex of claim 1, wherein the promoter is an inducible promoter.

8. The mammalian transformation complex of claim 1 wherein the promoter is from a cystic fibrosis transmembrane conductance regulator gene.

9. The mammalian transformation complex of claim 1, wherein the complex comprises DOPE and a lipid selected from the group consisting of DOTMA, DDAB, DOTAP and L-PE.

10. The mammalian transformation complex of claim 1, wherein the complex comprises cholesterol and a lipid selected from the group consisting of DOTMA, DDAB, DOTAP, E-PC, CEBA, E-DMPC, L-PE, and DOPE.

11. The mammalian transformation complex of claim 1, wherein the complex comprises a lipid selected from the group consisting of cholesterol, DOTMA, DDAB, DOTAP, E-PC, CEBA, E-DMPC, L-PE, and DOPE.

12. The mammalian transformation complex of claim 1, wherein the complex comprises a lipid other than DOTMA.

13. The mammalian transformation complex of claim 1, wherein the complex does not comprise DOTMA.

* * * * *